US008465945B2

(12) United States Patent
Best et al.

(10) Patent No.: US 8,465,945 B2
(45) Date of Patent: Jun. 18, 2013

(54) METHOD FOR PRODUCTION AND USE OF MITE GROUP 1 PROTEINS

(75) Inventors: Elaine A. Best, Fort Collins, CO (US); Martin J. McDermott, Fort Colllins, CO (US)

(73) Assignee: Merck Patent GmbH, Darmstadt (DE)

( * ) Notice: Subject to any disclaimer, the term of this patent is extended or adjusted under 35 U.S.C. 154(b) by 458 days.

(21) Appl. No.: 11/542,659

(22) Filed: Oct. 2, 2006

(65) Prior Publication Data

US 2007/0082369 A1  Apr. 12, 2007

Related U.S. Application Data

(62) Division of application No. 10/110,353, filed as application No. PCT/US00/28204 on Oct. 12, 2000, now abandoned.

(60) Provisional application No. 60/159,841, filed on Oct. 15, 1999.

(51) Int. Cl.
  *C07H 21/02* (2006.01)
  *C07H 21/04* (2006.01)
  *C12N 15/09* (2006.01)
  *C12N 1/00* (2006.01)
  *C12N 15/74* (2006.01)
  *C12P 21/06* (2006.01)

(52) U.S. Cl.
  USPC ... 435/69.1; 435/69.3; 435/255.1; 435/255.4; 435/255.5; 435/255.6; 435/471; 435/483; 435/476; 536/23.1

(58) Field of Classification Search
  None
  See application file for complete search history.

(56) References Cited

U.S. PATENT DOCUMENTS

| | | | |
|---|---|---|---|
| 4,727,019 A | 2/1988 | Valkirs et al. |
| 4,879,231 A | 11/1989 | Stroman et al. |
| 5,415,994 A | 5/1995 | Imrich et al. |
| 5,424,193 A | 6/1995 | Pronovost et al. |
| 5,433,948 A | 7/1995 | Thomas et al. |
| 5,552,142 A | 9/1996 | Thomas et al. |
| 5,646,115 A | 7/1997 | Frank et al. |
| 5,770,202 A | 6/1998 | Thomas et al. |
| 5,773,002 A | 6/1998 | Thomas et al. |
| 5,820,862 A | 10/1998 | Garman et al. |
| 5,840,695 A | 11/1998 | Frank et al. |
| 5,932,470 A | 8/1999 | Frank et al. |
| 5,945,294 A | 8/1999 | Frank et al. |
| 5,958,880 A | 9/1999 | Frank et al. |
| 5,968,526 A | 10/1999 | Garman et al. |
| 5,972,352 A | 10/1999 | Thomas et al. |
| 5,973,132 A | 10/1999 | Thomas et al. |
| 6,060,057 A | 5/2000 | Thomas et al. |
| 6,071,522 A | 6/2000 | Thomas et al. |
| 6,074,846 A | 6/2000 | Ralston et al. |
| 6,077,518 A | 6/2000 | Thomas et al. |
| 6,086,897 A | 7/2000 | Thomas et al. |
| 6,132,734 A | 10/2000 | Thomas et al. |
| 6,147,201 A | 11/2000 | Thomas et al. |
| 6,268,491 B1 | 7/2001 | Garman et al. |
| 6,423,837 B1 | 7/2002 | Thomas et al. |

FOREIGN PATENT DOCUMENTS

| | | |
|---|---|---|
| AU | 717187 | 4/1995 |
| JP | 10-218897 | 8/1998 |
| WO | WO-88/10297 A1 | 12/1988 |
| WO | WO-92/04445 A1 | 3/1992 |
| WO | WO-94/01775 A1 | 1/1994 |
| WO | WO 94/05790 * | 3/1994 |
| WO | WO 94 24281 A | 10/1994 |
| WO | WO-94/29696 A1 | 12/1994 |
| WO | WO-98/12563 A1 | 3/1998 |
| WO | WO-98/45707 A1 | 10/1998 |
| WO | WO 9925823 A2 | 5/1999 |
| WO | WO-99/38974 A1 | 8/1999 |

OTHER PUBLICATIONS

Metzler et al. 'Solution structure of human CTLA-4 and delineation of a CD80/CD86 binding site conserved in CD28.' Nature Structural Biol. 4:527-531, 1997.*
Smith et al. The challenges of genome sequence annotation or "the devil is in the details". Nat. Biotech.15:1222-1223, 1997.*
Brenner S. 'Errors in genome annotation.' Trends in Genetics 15:132-133, 1999.*
Bowie et al. Decipering the Message in Protein Sequences: Tolerance to Amino Acid Substitutions. Science 247:1306-1310, 1990.*
Sowka et al. 'Identification and cloning of Prs a 1, a 32-kDa Endochitinase and major allergen of avocado, and its expression int he yeast *Pichi pastoris*.' J. Biol. Chem. 273(43):28091-28097, 1998.*
Nomenclature for Incompletely Specified Bases in Nucleic Acid Seqences, prepared by G.P. Moss and downloaded May 22, 2006 from world wide web chem. Qmul.ac.uk/iubmb/misc/naseq.html, 11 pages.
Kent Nicholas A et al, "*Molecular characterization of group I allergen Eur m I From house dust mite Euroglyphus maynei*." International Archives of Allergy and Immunology, vol. 99, No. 1, 1992, pp. 150-152

(Continued)

*Primary Examiner* — Nora Rooney
(74) *Attorney, Agent, or Firm* — Perkins Coie LLP

(57) ABSTRACT

The present invention includes a method to produce a recombinant mite Group 1 protein in a methyltrophic yeast or an *Escherichia coli* microorganism. The present invention also relates to a recombinant mite Group 1 protein obtained by such a method, such a recombinant protein being able to selectively bind IgE or cause proliferation of a T cell that proliferate in response to a native mite Group 1 protein. Also included in the present invention is the use of such a recombinant mite Group 1 protein to detect mite allergy or to reduce an allergic response to a mite Group 1 protein. The present invention also includes novel mite Group 1 nucleic acid molecules, proteins, recombinant molecules, and recombinant cells, as well as uses thereof.

14 Claims, No Drawings

OTHER PUBLICATIONS

Best Elaine A et al, "*A recombinant group 1 house dust mite allergen, rDer f 1, with biological activities similar to those of the native allergen*." Protein Expression and Purification, vol. 20, No. 3 Dec. 2000, pp. 462-471.

Arlian L.G., et al. (1993) Allergenicity of the mite, *Blomia tropicalis*. J Allergy Clin Immunol. 91(5):1042-50.

Becker D.M., et al. (1991) High-efficiency transformation of yeast by electroporation. Methods Enzymol. 194:182-7.

Chua K.Y., et al. (1992) High-frequency binding of IgE to the Der p allergen expressed in yeast. J Allergy Clin Immunol. 89(1 Pt 1):95-102.

Chua, et al. (1988) Sequence analysis of cDNA coding for a major house dust mite allergen, Der p 1. Homology with cysteine proteases. J Exp Med. 167(1):175-82.

Illy C., et al. (1997) Role of the occluding loop in cathepsin B activity. J Biol Chem. 272(2):1197-202.

Lombardero M., et al. (1990) Conformational stability of B cell epitopes on group I and group II *Dermatophagoides* spp. allergens. Effect of thermal and chemical denaturation on the binding of murine IgG and human IgE antibodies.J Immunol. 144(4):1353-60.

Shoji, H. et al. (1996) Production of recombinant mite allergen Der fl in insect cells and characterization of products—removal of prosequence is essential to IgE-binding activity. Biosci Biotechnol Biochem. 60(4):621-5.

Shoji H., et al. (1997) Production of recombinant Der fl with the native IgE-binding activity using a baculovirus expression system. Biosci Biotechnol Biochem. 61(10):1668-73.

Thomas W.R. (1996) Recombinant allergens for immunotherapy. Adv Exp Med Biol. 409:85-93.

Thomas W.R., et al. (1998) House-dust-mite allergens. Allergy. 53(9):821-32. 1998, Allergy 53:821-832.

* cited by examiner

METHOD FOR PRODUCTION AND USE OF MITE GROUP 1 PROTEINS

CROSS-REFERENCE TO RELATED APPLICATION

This application is a Divisional of U.S. patent application Ser. No. 10/110,353 filed Sept. 9, 2002, now abandoned, which is a 371 National Stage entry of International Application No. PCT/US2000/028204, filed Oct. 12, 2000, published as WO 2001/029078 with an International Publication Date of Apr. 26, 2001, which claims priority to U.S. Provisional Application No. 60/159,841 filed Oct. 15, 1999.

FIELD OF THE INVENTION

The present invention relates to a method of expressing an active recombinant mite Group 1 protein in a methyltrophic yeast microorganism or in *Escherichia coli*. The present invention also relates to use of such a protein to detect mite allergy or to reduce an allergic response.

BACKGROUND OF THE INVENTION

The cross-linking of mast cell-bound IgE upon binding of IgE to allergens induces Type I allergic diseases such as atopic dermatitis and atopic asthma. Diseases related to allergy and atopy affect a significant percentage of the population, including up to 20% of humans, and are increasing every year. A significant proportion of type I allergic patients are mite allergic. For example, based on skin tests, at least 75% of the estimated 50 million asthmatics in the United States are mite allergic. As such, mite proteins comprise an important allergen in type I allergic disease. The house dust mites *Dermatophagoides farinae* and *Dermatophagoides pteronyssinus* are the most common mites in the United States. These mites produce several classes, or groups, of allergens, one of which is known as Group 1 proteins, which are also found in other mite species. For example, considerable cross-reactivity has been found among *Blomia tropicalis*, *D. farinae* and *Lepidoglyphus destructor* allergens; see, for example, Colloff, 1993, *J Allergy Clin Immunol* 91, 1042-1050. Additionally, Group 1 proteins have been found in *D. pteronyssinus*, *D. farinae*, *Euroglyphus maynei*, and *L. destructor*, see, for example, Thomas et al, 1998, *Allergy* 53, 821-832.

Mite Group 1 proteins share significant homology with a family of cysteine proteases including actinidin, papain, cathepsin H and cathepsin B. These Group 1 proteins are commonly found in the feces of mites and are thought to function as digestive enzymes in the mite intestine. Group 1 proteins from different mites are highly homologous, approximately 25-kilodalton (kD) secretory glycoproteins, that are synthesized by the cell as a pre-pro-protein that is processed to a mature form. *D. farinae*, *D. pteronyssinus*, and *E. maynei* Group 1 proteins, for example, share about 80% identity. In particular, Group 1 proteins from *D. farinae* and *D. pteronyssinus*, also referred to as Der f 1 and Der p 1 proteins, respectively, show extensive cross-reactivity in binding IgE and IgG. In human populations that are mite allergic, approximately 80% to 90% have IgE that is reactive to Group 1 proteins; see Thomas, 1996, *Adv Exp Med Biol* 409, 85-93.

Since Group 1 proteins are important in mite allergy, it is desirable to have sufficient quantities of these proteins for uses related to diagnosing and treating diseases that are related to mite allergy. To obtain the amounts of Group 1 proteins necessary for these purposes, it is desirable to use recombinant expression systems, since the amount of Group 1 proteins in mites is relatively small and the purification process to obtain native Group 1 proteins is a difficult, multi-step process. Nucleic acid molecules encoding Der f 1 and Der p 1 proteins were isolated a number of years (see, for example, U.S. Pat. No. 5,433,948, issued Jul. 18, 1995, by Thomas et al; U.S. Pat. No. 5,552,142, issued Sep. 3, 1996, by Thomas et al; U.S. Pat. No 5,770,202, issued Jun. 23, 1998, by Thomas et al; U.S. Pat. No.5,773,002, issued Jun. 30, 1998, by Thomas et al; PCT Patent Publication No. WO 88/10297, published Dec. 29, 1988, by Thomas et al; PCT Patent Publication No. WO 92/04445, published Mar. 19, 1992, by Thomas et al); and researchers have tried to express Group 1 proteins in recombinant expression systems. Until the present invention, however, there has been only limited success in producing an active, easily purified recombinant mite Group 1 protein. For example, although researchers have tried to produce active, fully functional recombinant Der f 1 and Der p 1 proteins in *E. coli*, insect cells, and *Saccharomyces cerevisiae*, to date, none of these efforts has yielded an easily purified Group 1 protein that binds to IgE in mite-allergic patients in a manner equivalent to a native Group 1 protein.

Using *E. coli*, researchers expressed a recombinant Der p 1 protein as a fusion protein with glutathione S transferase. The resulting recombinant protein was produced in very low yields, at about 200 micrograms soluble protein per liter of culture medium. Furthermore the GST-Der p 1 fusion protein exhibited only about 50% of the IgE reactivity of the native protein; see Chua et al, 1992, *J Allergy Clin Immunol* 89, 95-102. Moreover, this protein was expressed using a cDNA encoding the mature form, not the pro-form. The inventors are not aware of any reports of successful expression in *E. coli* of an active Der p 1 protein encoded by the pro-form.

Using a baculovirus expression system in insect cells, Shoji et al, 1996, *Biosci Biotech Biochem* 60, 621-625, and Shoji et al, 1997, *Biosci Biotech Biochem* 61, 1668-1673, reported production of a recombinant Der f 1 protein with IgE binding activity comparable to the native protein, but their process required an additional post-purification step of either acid or enzymatic treatment to cleave the pro-form to a mature form. This cleavage step was necessary because the Der f 1 pro-form had only 20% of the IgE reactivity of the native protein. To avoid the step of acid proteolysis, Shoji et al. converted a glutamate at the carboxyl-terminus of the "pro" region of the pro-form to a lysine residue. This genetically engineered version of Der f 1 protein could then be cleaved with lysylendopeptidase to the mature form under conditions that did not result in the cleavage of internal lysines. However, this process is disadvantageous, especially at large scale, for producing recombinant proteins. Controlling a relatively non-specific protease cleavage step to cleave at only one specific site out of several possible sites is inherently difficult. In addition, use of a protease adds steps and cost to the purification process.

Using the yeast *S. cerevisiae*, Chua et al, ibid., produced recombinant Der p 1 protein. Although the Der p 1 protein was expressed as the pro-form in this system, the protein was not secreted by *S. cerevisiae*. As such, the resulting insoluble protein was purified using several steps, including solubilization, renaturation and affinity chromatography; such a process resulted in low yields of only about 1 milligram protein per liter of yeast culture. Furthermore, the recovered *S. cerevisiae*-expressed Der p 1 proenzyme exhibited only about 80% of the activity of native Der p 1 protein: Of 11 sera tested that were reactive with the native protein, only 9 were reactive with the *S. cerevisiae* expressed Der p 1 protein.

Thus, there remains a need in the art for an expression system that produces recombinant mite Group 1 proteins that exhibit activity equivalent to that of native mite Group 1 proteins. Preferably such a system would allow for easy and cost-effective recovery of such recombinant proteins.

SUMMARY OF THE INVENTION

This invention relates to the surprising discovery that soluble, fully active mite Group 1 proteins can be expressed by a methyltrophic yeast microorganism. Also surprising is the finding that a methyltrophic yeast microorganism expresses a pro-form of a mite Group 1 protein that is efficiently processed and secreted, resulting in soluble, mature, fully active mite Group 1 protein in the culture medium.

This invention also relates to the unexpected discovery that a pro-form of a mite Group 1 protein allergen can be expressed in *Escherichia coli* and refolded such that the renatured protein has activity that is nearly equivalent to a native Group 1 mite protein. Not only did this pro-form exhibit higher activity than previously reported for an *E. coli*-produced mature form of such a protein, but this is apparently the first report of an active pro-form of a Group 1 mite protein.

The present invention provides a method to produce a recombinant mite Group 1 protein, wherein the protein has a function of selectively binding IgE that binds to a native mite Group 1 protein and/or of causing proliferation of a T cell that proliferates in response to a native mite Group 1 protein, such a method including the steps of (a) culturing a methyltrophic yeast microorganism transformed with a nucleic acid molecule that encodes a mite Group 1 protein, and (b) recovering the expressed protein. Preferably such a protein is secreted into the culture the medium and has an IgE binding activity that is substantially equivalent to that of a native mite Group 1 protein. Preferred methyltrophic yeast microorganisms include those of the genera *Pichia*, *Hansenula*, *Torulopsis*, and *Candida*, with those of the genus *Pichia* being particularly preferred. The present invention also includes a mite Group 1 protein produced by such a method.

The present invention also provides a method to produce a recombinant mite Group 1 protein, wherein the protein has a function of selectively binding IgE that binds to a native mite Group 1 protein and/or of causing proliferation of a T cell that proliferates in response to a native mite Group 1 protein, such a method comprising the steps of (a) culturing an *E. coli* microorganism transformed with a nucleic acid molecule encoding such a mite Group 1 protein, wherein the protein forms an inclusion body in the *E. coli* microorganism, (b) isolating such an inclusion body from such an *E. coli* microorganism, and (c) recovering the mite Group 1 protein from such an inclusion body, wherein the recovered mite Group 1 protein binds to IgE of at least about 70% of serum samples comprising IgE that selectively bind to a native mite Group 1 protein. Such a method preferably includes a refolding step. The present invention also includes a mite Group 1 protein produced by such a method.

Also included in the present invention is a method to detect mite allergy in an animal. Such a method includes the steps of (a) contacting an isolated mite Group 1 protein of the present invention with a putative IgE-containing substance under conditions suitable to form a complex between the mite Group 1 protein and IgE and (b) determining the presence of IgE reactive with the mite Group 1 protein by detecting the complex, wherein presence of reactive IgE is indicative of mite allergy in the animal. The present invention also includes a kit for detection of mite allergy in an animal. Such a kit includes a mite Group 1 protein of the present invention and a means for detecting IgE that selectively binds to a mite Group 1 protein.

One embodiment of the present invention is a composition that includes a mite Group 1 protein of the present invention and an excipient. Also included is a method to use such a composition to reduce an allergic response to a mite Group 1 protein in a mite-allergic animal. Such a method includes the step of administering such a composition to such an animal.

Another embodiment of the present invention includes a methyltrophic yeast microorganism that includes a nucleic acid molecules encoding a mite Group 1 protein operatively linked to a transcription control sequence.

The present invention also includes isolated novel nucleic acid molecules, recombinant molecules, and recombinant microorganisms that comprise at least one of the following nucleic acid sequences: SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, and SEQ ID NO:45. Also included in the present invention is an isolated protein having an amino acid sequence of SEQ ID NO:38 or SEQ ID NO:41, as well as nucleic acid molecules, recombinant molecules, and recombinant microorganisms encoding such protein(s).

DETAILED DESCRIPTION OF THE INVENTION

The present invention provides a method to produce a recombinant mite Group 1 protein that has at least one of the following functions (i.e., activities, properties): (a) selectively binding IgE that binds to a native mite Group 1 protein; and (b) causing proliferation of a T cell that proliferates in response to a native mite Group 1 protein. In one embodiment, the method includes the steps of (a) culturing a methyltrophic yeast microorganism transformed with a nucleic acid molecule that encodes a mite Group 1 protein, and (b) recovering the recombinant protein from the methyltrophic yeast microorganism. In another embodiment, the method includes the steps of (a) culturing an *E. coli* microorganism transformed with a nucleic acid molecule encoding a mite Group 1 protein, wherein the protein forms an inclusion body in the *E. coli* microorganism, (b) isolating such an inclusion body from such an *E. coli* microorganism, and (c) recovering the mite Group 1 protein from such an inclusion body, wherein the recovered mite Group 1 protein binds to IgE of at least about 70% of serum samples comprising IgE that selectively bind to a native mite Group 1 protein. The present invention also includes a recombinant mite Group 1 protein produced by either of these methods. Such a protein is referred to as a recombinant mite Group 1 protein of the present invention, a mite Group 1 protein of the present invention, a Group 1 protein of the present invention, or a protein of the present invention. Such a protein can be used in a variety of ways, such as those disclosed herein. For example, a protein of the present invention can be used to detect mite allergy in an animal, including detection of an animal suffering from mite allergy or of an animal susceptible to mite allergy. As another example, a protein of the present invention can be used to reduce an allergic response against a mite allergen (i.e., reduce mite allergy), including prophylactic or therapeutic use. The present invention also includes kits and compositions that include at least one recombinant mite Group 1 protein of the present invention. The present invention also includes mite Group 1 nucleic acid molecules, recombinant molecules, recombinant microorganisms and proteins, as disclosed herein.

As used herein, a mite refers to a minute arthropod of the order Acarina, which includes a large assemblage of parasitic and free-living organisms. For example, astigmatic mites (Astigmata) are mostly involved in commensal, symbiotic, or ectoparasitic relationships with other animals for at least part of their life cycle. There are at least two major lineages of astigmatic mites: Psoroptidia, which includes all species that are associated with skin, feathers, fur, and hair, such as ectoparasitic feather mites and skin parasites of mammals; and Pyroglyphidae, which includes mite species that are parasites of birds and nest-dwelling commensals, as well as those species found in house dust. Allergen-producing astigmatic mites include *Acarus siro, Aleuroglyphus ovatus, Blomia kulagini, Blomia tropicalis, Chortoglyphus arcuatus, Dermatophagoides farinae, Dermatophagoides microceras, Dermatophagoides pteronyssinus, Euroglyphus maynei, Glycyphagus domesticus, Gohieria fusca, Lepidoglyphus destructor, Psoroptes ovis, Pterolichus obtusus, Sarcoptes scaiei, Tyrophagus longior*, and *Tyrophagus putrescentiae*. The main species of mite found in house dust are *D. farinae* and *D. pteronyssinus*, which together account for 80-90% of the total mite population generally found in houses. Additionally, *B. kulagini, B. tropicalis, E. maynei*, and *T. longior* are also found in houses. As such, any mite is a suitable target for the products and methods of the present invention. Preferred mites to target are of the genera *Blomia, Dermatophagoides, Euroglyphus*, and *Tyrophagus*, with those of the species *B. kulagini, B. tropicalis, D. farinae, D. pteronyssinus, E. maynei*, and *T. longior* being more preferred. Particularly preferred mites to target are those mites of the genus *Dermatophagoides*, with those of the species *D. farinae* and *D. pteronyssinus* being more preferred.

One embodiment of the present invention is a method to produce a recombinant mite Group 1 protein, wherein the recombinant protein has a function of selectively binding IgE that binds to native Group 1 protein, and/or of causing proliferation of a T cell that proliferates in response to a native mite Group 1 protein. It is to be noted that the term "a" or "an" entity refers to one or more of that entity; for example, a protein refers to one or more proteins or at least one protein; as another example, a nucleic acid molecule refers to one or more nucleic acid molecules or at least one nucleic acid molecule. As such, the terms "a" or "an", "one or more", and "at least one" can be used interchangeably herein. It is also to be noted that the terms "comprising", "including", and "having" can be used interchangeably herein. According to the present invention, an isolated, or biologically pure, protein or nucleic acid molecule is a protein or nucleic acid molecule, respectively, that has been removed from its natural milieu. As such, "isolated" and/or "biologically pure" do not necessarily reflect the extent to which the protein or nucleic acid molecule has been purified. An isolated protein or nucleic acid molecule of the present invention can be obtained from its natural source, can be produced using recombinant nucleic acid technology, or can be produced by chemical synthesis.

A mite Group 1 protein refers to a Group 1 protein from (including derived from) a species of mite. A recombinant mite Group 1 protein of the present invention refers to a mite Group 1 protein produced using the techniques of recombinant nucleic acid technology. A suitable recombinant mite Group 1 protein of the present invention is a Group 1 protein from any species of mite that is produced using recombinant nucleic acid techniques. Such species include, but are not limited to, *Acarus siro, Aleuroglyphus ovatus, Blomia kulagini, Blomia tropicalis, Chortoglyphus arcuatus, Dermatophagoides farinae, Dermatophagoides microceras, Dermatophagoides pteronyssinus, Euroglyphus maynei, Glycyphagus domesticus, Gohieria fusca, Lepidoglyphus destructor, Psoroptes ovis, Pterolichus obtusus, Sarcoptes scaiei, Tyrophagus longior*, and *Tyrophagus putrescentiae*. Preferred mite Group 1 proteins of the present invention include those of the genera *Blomia, Dermatophagoides, Euroglyphus, Lepidoglyphus*, and *Tyrophagus*, with those of the species *B. kulagini, B. tropicalis, D. farinae, D. microceras, D. pteronyssinus, E. maynei, L. destructor*, and *T. longior* being more preferred. Particularly preferred mite Group 1 proteins are *Dermatophagoides* and *Euroglyphus maynei* Group 1 proteins, with *D. farinae, D. pteronyssinus*, and *E. maynei* Group 1 proteins being even more preferred.

In one embodiment, mite Group 1 proteins include, but are not limited to, mite proteins that share homology with mite cysteine proteases having molecular weights of about 25 kD, although such molecular weights may vary, for example due to genetic differences between species or post-translation modifications.

As used herein, an isolated mite Group 1 protein may be a full-length protein or any homolog of such a protein. An isolated mite Group 1 protein of the present invention, including a homolog, can be identified in a straight-forward manner by the protein's ability to perform at least one of the following functions: elicit an immune response against, or to, a mite Group 1 protein, bind to an IgE antibody (also referred to herein as IgE) reactive to a native mite Group 1 protein, bind to one or more monoclonal antibodies that are reactive to a native mite Group 1 protein, and/or stimulate proliferation of a T cell that proliferates in response to a native mite Group 1 protein. Examples of protein homologs of the present invention include mite Group 1 proteins of the present invention in which amino acids have been deleted (e.g. a truncated version of the protein, such as a peptide), inserted, inverted, substituted, and/or derivatized (e.g., by glycosylation, phosphorylation, acetylation, myristoylation, prenylation, palmitoylation, amidation, and/or addition of glycerophosphatidyl inositol) such that the protein homolog exhibits one of the aforementioned functions. Homologs of mite Group 1 proteins of the present invention can be the result of natural allelic variation, including natural mutation. Protein homologs of the present invention can also be produced using techniques known in the art including, but not limited to, direct modifications to the protein and/or modification to a gene or nucleic acid molecule encoding the protein using, for example, classic or recombinant DNA techniques to effect random or targeted mutagenesis. Such nucleic acid molecules are referred to herein as nucleic acid molecule homologs. A preferred recombinant mite Group 1 protein of the present invention is a pro-form or a mature form of a mite Group 1 protein.

A recombinant mite Group 1 protein of the present invention is a protein that is encoded by a mite Group 1 nucleic acid molecule of the present invention, also referred to as a nucleic acid molecule of the present invention. Such nucleic acid molecules are described in more detail herein. A recombinant mite protein of the present invention preferably has at least one of the following functions: (a) ability to selectively bind IgE; and (b) ability to cause proliferation of a T cell that proliferates in response to a native mite Group 1 protein. A native mite Group 1 protein refers to a Group 1 protein recovered directly from a species of mite. In one embodiment, a native mite Group 1 protein is purified from a mite extract under conditions that retain the mite Group 1 protein's inherent IgE reactivity. As used herein, a protein's IgE reactivity refers to the ability of that protein to selectively bind IgE that is reactive with a mite Group 1 protein. As used herein, the terms selectively binds IgE and selectively binds to (or with)

IgE refer to the ability of a mite Group 1 protein of the present invention to preferentially bind to IgE specific for Group 1 allergens, without being able to substantially bind to IgE specific for other allergens. IgE that is reactive with a mite Group 1 protein is an IgE antibody that reacts with a mite Group 1 protein in a manner equivalent to an IgE raised in response to a mite Group 1 protein. Methods to purify native mite Group 1 proteins such that they retain their inherent (i.e., natural) IgE reactivity are known to those skilled in the art, examples of which are disclosed herein. Such a native mite Group 1 protein can be used as a "standard" by which to compare a function, or activity, of a mite Group 1 protein obtained by other means, such as by expression of a recombinant form of a mite Group 1 protein of the same species as that from which the native protein is purified.

The ability of a recombinant mite Group 1 protein to selectively bind to IgE can be assayed by methods known in the art, such as, but not limited to, those disclosed herein. Methods to compare that IgE binding activity with the IgE binding activity of a native mite Group 1 protein are also known in the art and include, but are not limited to, those methods disclosed herein. In one embodiment, recombinant and native forms of a mite Group 1 protein are contacted (i.e., reacted) with serum samples from animals that are allergic to mites using, for example, an ELISA format, and a determination is made of what percentage of serum samples reactive with the native protein are also reactive with the recombinant protein. Preferably the testing is conducted using assay conditions in which essentially all of the mite-allergic serum samples give a positive result with the native mite Group 1 protein. An example of how the percentage is determined is as follows: if a recombinant mite Group 1 protein is tested against 10 mite-allergic serum samples, wherein all 10 samples are reactive to a native mite Group 1 protein, and only 7 samples are reactive to the recombinant protein, the reactivity is expressed as 7/10, or 70%. That is, the recombinant mite Group 1 protein selectively binds to IgE of 70% of serum samples comprising IgE that selectively bind to a native mite Group 1 protein. As used herein, a recombinant mite Group 1 protein that has comparable, or substantially equivalent, activity to a native mite Group 1 protein is a recombinant mite Group 1 protein that reacts with essentially all of the serum samples that are reactive with the native Group 1 protein.

In another embodiment, the abilities of recombinant and native forms of a mite Group 1 protein to selectively bind to a monoclonal antibody raised against a native mite Group 1 monoclonal antibody (i.e., an anti-native mite Group 1 monoclonal antibody) or to a panel of such monoclonal antibodies are compared. A recombinant Group 1 protein that has comparable, or substantially equivalent, activity to a native Group 1 protein is a recombinant mite Group 1 protein that reacts with essentially all of the monoclonal antibodies that react with the native mite Group 1 protein. In the addition, the binding affinities of the monoclonal antibodies for the recombinant Group 1 protein should be very similar to the respective binding affinities of the monoclonal antibodies for the native Group 1 protein. The binding affinity can be determined with a simple dose-response curve.

A preferred method to determine the IgE reactivity of a recombinant mite Group 1 protein is to compare the reactivities of recombinant and native forms of a mite Group 1 protein to IgE in serum samples that selectively bind to native mite Group 1 proteins. The phrase, an IgE activity substantially equivalent to that of a native mite Group 1 protein refers to an IgE reactivity that is very comparable, or similar to, the activity of a native mite Group 1 protein. Preferred mite Group 1 proteins of the present invention exhibit IgE reactivities that are at least about 70%, preferably at least about 75%, more preferably at least about 80%, more preferably at least about 85%, more preferably at least about 90%, and more preferably at least about 95% equivalent to a native mite Group 1 protein. A particularly preferred recombinant mite Group 1 protein of the present invention selectively binds to IgE of about 100% of serum samples comprising IgE that selectively bind to a native mite Group 1 protein.

The ability of a recombinant mite Group 1 protein of the present invention to cause proliferation of a T cell that proliferates in response to a native mite Group 1 protein, also referred to herein as T cell reactivity, can be assayed by methods known in the art; see, for example, Janeway, et al., 1996, *Immunobiology*, Second Edition, Garland Publishing Inc., New York, N.Y.; Janeway et al., ibid., is incorporated by reference herein in its entirety. In one embodiment, a recombinant mite Group 1 protein of the present invention preferably contains most or all of the relevant dominant T cell epitopes to stimulate T cell proliferation. In order to determine whether a recombinant mite Group 1 protein contains relevant dominant T cell epitopes, T cell proliferation assays can be performed, by methods known to those skilled in the art, and the ability of that recombinant mite Group 1 protein to stimulate T cell proliferation can be compared to the ability of the corresponding native mite Group 1 protein to stimulate T cell proliferation. A preferred recombinant mite Group 1 protein of the present invention stimulates T cell proliferation as well as, or in a comparable manner to, a native mite Group 1 protein.

A mite Group 1 nucleic acid molecule of the present invention refers to a Group 1 nucleic acid molecule derived from a mite, and as such, can be obtained from its natural source (i.e., directly from a mite, examples of such mites being disclosed herein), or can be produced using, for example, recombinant nucleic acid technology (e.g., polymerase chain reaction (PCR) amplification or cloning) or chemical synthesis. A nucleic acid molecule of the present invention can be DNA, RNA, or a derivative of DNA or RNA. Mite Group 1 nucleic acid molecules include natural forms including allelic variants, complementary DNAs (cDNAs) or RNAs derived from genomic sequences (including those incorporating natural variations), and nucleic acid molecules modified by nucleotide insertions, deletions, substitutions, and/or inversions in a manner such that the modifications do not substantially interfere with the nucleic acid molecule's ability to encode a mite Group 1 protein of the present invention. A modified mite Group 1 nucleic acid homolog can be produced using a number of methods known to those skilled in the art, see, for example, Sambrook et al,1989, *Molecular Cloning: A Laboratory Manual*, Cold Spring Harbor Labs Press; Sambrook et al, ibid. is incorporated by reference herein in its entirety. For example, nucleic acid molecules can be modified using a variety of techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecules of the present invention can be selected by hybridization with a mite Group 1 nucleic acid molecule, as discussed below, and by the ability of such nucleic acid molecules to encode a mite Group 1 protein that selectively binds to IgE and/or causes proliferation of a T cell that proliferates in response to a native mite roup 1 protein. A full-length mite Group 1 protein, i.e., the initial translation product, is a pre-pro-form of the protein containing a pre-segment and a pro-segment as well as the mature protein. The pre-segment, or pre-sequence, also known as the leader sequence or the signal sequence, apparently directs the mite Group 1 protein to be secreted from the cell and is proteolytically cleaved to yield a pro-form of the protein. The pro-segment, or pro-sequence, is then proteolytically cleaved to yield the mature Group 1 protein. A preferred protein to express is the pro-form (which includes the mature sequence as well as the pro sequence, but does not have a signal sequence attached) or the mature form.

Nucleic acid molecules and proteins of the present invention that are of certain species and lengths are denoted as follows: a Der f 1 nucleic acid molecule protein of a certain length is denoted as $nDerf1_\#$, for example, $nDerf1_{963}$ wherein "#" refers to the number of nucleotides in that molecule; in a similar fashion, a Der p 1 nucleic acid molecule of a certain length is denoted as $nDerp1_\#$, a E. maynei Group 1 nucleic acid molecule of a certain length is denoted as $nEurm1_\#$ and so on. Similarly, a Der f 1 protein of the present invention of known length is denoted $PDerf1_\#$, a Der p 1 protein of the present invention of known length is denoted $PDerp1_\#$, a E. maynei Group 1 protein of a certain length is denoted as $PEurm1_\#$ and so on.

A mite Group 1 nucleic acid molecule of the present invention includes a nucleic acid molecule that hybridizes under stringent conditions with a nucleic acid molecule having at least one of the following nucleic acid sequences: SEQ ID NO:3, SEQ ID NO:6, SEQ ID NO:9, SEQ ID NO:12, SEQ ID NO:15, SEQ ID NO:18, SEQ ID NO:21, SEQ ID NO:24, SEQ ID NO:27, SEQ ID NO:30, SEQ ID NO:33, SEQ ID NO:36, SEQ ID NO:39, SEQ ID NO:42, and SEQ ID NO:45.

SEQ ID NO:1 is the nucleic acid sequence of the coding strand of $nDerf1_{963}$, a nucleic acid molecule that contains the coding sequence of the full-length, or pre-pro-form, of a Der f 1 protein. SEQ ID NO:4 is the nucleic acid sequence of the coding strand of $nDerf1_{1909a}$, a nucleic acid molecule that contains the coding sequence of the pro-form of a Der f 1 protein; the coding sequence of this pro-form protein spans from nucleotide 55 to nucleotide 963 of SEQ ID NO:1. SEQ ID NO:7 is the nucleic acid sequence of the coding strand of $nDerf1_{669a}$, a nucleic acid molecule that contains the coding sequence of the mature form of a Der f 1 protein; the coding sequence of the mature form spans from nucleotide 295 to nucleotide 963 of SEQ ID NO:1. Amino acid sequences SEQ ID NO:2, SEQ ID NO:5, and SEQ ID NO:8 represent the amino acid sequences of Der f 1 proteins $PDerf1_{321}$, $PDerf1_{303a}$, and $PDerf1_{223a}$, respectively, which are the translation products of nucleic acid sequences SEQ ID NO:1, SEQ ID NO:4, and SEQ ID NO:7 respectively. Nucleic acid sequences SEQ ID NO:3, SEQ ID NO:6, and SEQ ID NO:9 represent reverse complements of SEQ ID NO:1, SEQ ID NO:4, and SEQ ID NO:7, respectively, and as such represent the non-coding strands of nucleic acid molecules $nDerf1_{963}$, $nDerf1_{909a}$, and $nDerf1_{669a}$, respectively.

SEQ ID NO:10 is the nucleic acid sequence of the coding strand of $nDerp1_{960}$, a nucleic acid molecule that contains the coding sequence of the pre-pro-form of a Der p 1 protein. SEQ ID NO:13 is the nucleic acid sequence of the coding strand of $nDerp1_{906}$, a nucleic acid molecule that contains the coding sequence of the pro-form of a Der p 1 protein; the coding sequence of this pro-form spans from nucleotide 55 to nucleotide 960 of SEQ ID NO:10. SEQ ID NO:16 is the nucleic acid sequence of the coding strand of $nDerp1_{669}$, a nucleic acid molecule that contains the coding sequence of the mature form of a Der p 1 protein; the coding sequence of this mature form spans from nucleotide 292 to nucleotide 960 of SEQ ID NO:10. Amino acid sequences SEQ ID NO:11, SEQ ID NO:14, and SEQ ID NO:17 represent the amino acid sequences of Der p 1 proteins $PDerp1_{320}$, $PDerp1_{302}$, and $PDerp1_{223}$, respectively, which are the translation products of nucleic acid sequences SEQ ID NO:10, SEQ ID NO:13, and SEQ ID NO:16, respectively. Nucleic acid sequences SEQ ID NO:12, SEQ ID NO:15, and SEQ ID NO:18 represent reverse complements of SEQ ID NO:10, SEQ ID NO:13, and SEQ ID NO:16, respectively, and as such, represent the non-coding strands of nucleic acid molecules $nDerp1_{960}$, $nDerp1_{906}$, and $nDerp1_{669}$, respectively.

SEQ ID NO:19 is the nucleic acid sequence of the coding strand of $nEurm1_{963}$, a nucleic acid molecule that contains the coding sequence of the pre-pro-form of a E. maynei Group 1 protein. SEQ ID NO:22 is the nucleic acid sequence of the coding strand of $nEurm1_{909}$, a nucleic acid molecule that contains the coding sequence of the pro-form of a E. maynei Group 1 protein; the coding sequence of this pro-form spans from nucleotide 55 to nucleotide 963 of SEQ ID NO:19. SEQ ID NO:25 is the nucleic acid sequence of the coding strand of $nEurm1_{669}$, a nucleic acid molecule that contains the coding sequence of mature form of a E. maynei Group 1 protein; the coding sequence of this mature form spans from nucleotide 295 to nucleotide 963 of SEQ ID NO:19. Sequences SEQ ID NO:20, SEQ ID NO:23 and SEQ ID NO:26 represent the amino acid sequences of the E. maynei Group 1 proteins $PEurm1_{321}$, $PEurm1_{303}$, and $PEurm1_{223}$, respectively, which are the translation products of SEQ ID NO:19, SEQ ID NO:22, and SEQ ID NO:25, respectively. Nucleic acid sequences SEQ ID NO:21, SEQ ID NO:24, and SEQ ID NO:27 represent reverse complements of SEQ ID NO:19, SEQ ID NO:22, and SEQ ID NO:25, respectively, and as such, represent the non-coding strands of nucleic acid molecules $nEurm1_{963}$, $nEurm1_{909}$, and $nEurm1_{669}$, respectively.

SEQ ID NO:28 is the nucleic acid sequence of the coding strand of $nDerf1_{909b}$ and represents a novel nucleic acid sequence. This nucleic acid sequence is derived from SEQ ID NO:4, but incorporates several codon changes to reflect codon preferences in Pichia. The changes are as follows: a change from CGA to AGA in the codon spanning nucleotide positions 538 to 540 of SEQ ID NO:4; a change from CGA to AGA in the codon spanning nucleotide positions 547 to 549 of SEQ ID NO:4; a change from CGA to AGA in the codon spanning nucleotide positions 553 to 555 of SEQ ID NO:4; and a change from CGA to AGA in the codon spanning nucleotide positions 556 to 558 of SEQ ID NO:4. SEQ ID NO:31 is the nucleic acid sequence of the coding strand of $nDerf1_{669b}$ and also represents a novel nucleic acid sequence. This nucleic acid sequence is derived from SEQ ID NO:7, but incorporates several codon changes, to reflect codon preferences in Pichia. The changes are as follows: changes from CGA to AGA in the codons spanning nucleotide positions (a) 298 to 300, (b) 307 to 309, (c) 313 to 315, and (d) 316-318 of SEQ ID NO:7. SEQ ID NO:29 and SEQ ID NO:32 represent the amino acid sequences of proteins $PDerf1_{303b}$ and $PDerf1_{223b}$, respectively, which are the translation products of nucleic acid sequences SEQ ID NO:28 and SEQ ID NO:31, respectively. SEQ ID NO:30 and SEQ ID NO:33 represent reverse complements of SEQ ID NO:28 and SEQ ID NO:31, respectively.

SEQ ID NO:34 is the nucleic acid sequence of the coding strand of $nDerf1_{909c}$ and represents a novel nucleic acid sequence. This nucleic acid sequence is derived from SEQ ID NO:4, but incorporates several codon changes to reflect codon preferences in E. coli. The first change is from CCA to CCG in the codon spanning nucleotide positions 4 to 6 of SEQ ID NO:4; the second change is from CGA to CGT in the codon spanning nucleotide positions 547 to 549 of SEQ ID NO:4; the third is from CGA to CGT in the codon spanning nucleotide positions 553 to 555 of SEQ ID NO:4; the fourth is from CGA to CGT in the codon spanning nucleotide positions 556 to 558 of SEQ ID NO:4; and the fifth is from TAT to TAC in the codon spanning nucleotide positions 895 to 897 of SEQ ID NO:4 to eliminate a NdeI cloning site within the Der f 1 coding region. SEQ ID NO:43 is the nucleic acid sequence of the coding region of nDerfl$_{669d}$ and also represents a novel nucleic acid sequence. This nucleic acid sequence is derived from SEQ ID NO:7, but incorporates several codon changes to reflect codon preferences in E. coli. The first change is a change from CGA to CGT in the codon spanning nucleotide positions 307 to 309 of SEQ ID NO:7; the second is from CGA to CGT in the codon spanning nucleotide positions 313 to 315 of SEQ ID NO:7; the third is from CGA to CGT in the codon spanning nucleotide positions 316 to 318 of SEQ ID NO:7; and the fourth is from TAT to TAC in the codon spanning nucleotide positions 655 to 657 of SEQ ID NO:7 to eliminate a NdeI cloning site within the Der f 1 coding region. Sequences SEQ ID NO:35 and SEQ ID NO:44 represent the amino acid sequences of proteins PDerfl$_{303c}$ and PDerfl$_{223d}$, respectively, and are the translation products of nucleic acid sequences SEQ ID NO:34 and 43, respectively. SEQ ID NO:36 and SEQ ID NO:45 represent reverse complements of SEQ ID NO:34 and SEQ ED NO:43, respectively.

SEQ ID NO:37 is the nucleic acid sequence of the coding strand of nDerfl$_{909d}$ and represents a novel nucleic acid sequence. This nucleic acid sequence is derived from SEQ ID NO:28, the D. farinae pro-form Group 1 protein with codons altered to reflect Pichia codon preferences described above; however, SEQ ID NO:37 has also been altered to change the codon spanning nucleotide positions 397 to 399 of SEQ ID NO:28 from AAC (encoding asparagine (N)) to CAA (encoding glutamine (Q)). This change results in the encoding of a protein that lacks an N-linked glycosylation site. Thus, translation of SEQ ID NO:37 yields amino acid sequence SEQ ID NO:38 which is representative of protein PDerfl$_{303d}$, which is a novel protein, with the N to Q change at position 133 of the amino acid sequence. SEQ ID NO:39 represents the reverse complement of SEQ ID NO:37.

SEQ ID NO:40 is the nucleic acid sequence of the coding strand of nDerfl$_{669c}$ and represents a novel nucleic acid sequence. This nucleic acid sequence is derived from SEQ ID NO:31, the D. farinae mature form Group 1 protein with codons altered to reflect Pichia codon preferences described above; however, SEQ ID NO:40 has also been altered to change the codon spanning nucleotide positions 157 to 159 of SEQ ID NO:31 from AAC (encoding asparagine (N)) to CAA (encoding glutamine (Q)). This change results in the encoding of a protein that lacks an N-linked glycosylation site. Thus, translation of SEQ ID NO:40 yields amino acid sequence SEQ ID NO:41 which is representative of protein PDerfl$_{223c}$, which is a novel protein, with the N to Q change at position 53 of the amino acid sequence. SEQ ID NO:42 represents the reverse complement of SEQ ID NO:40.

As stated above, a mite Group 1 nucleic acid molecule of the present invention includes a nucleic acid molecule that hybridizes under stringent conditions with a nucleic acid molecule having a specified nucleic acid sequence. Stringent hybridization conditions are determined based on defined physical properties of the gene or other nucleic acid molecule to which the nucleic acid molecule to be tested is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, Molecular Cloning: A Laboratory Manual, Cold Spring Harbor Labs Press, and Meinkoth, et al., 1984, Anal. Biochem. 138, 267-284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C content of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m=81.5° C.+16.6 \log M+0.41(\% G+C)-500/n-0.61(\% \text{ formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d=4(G+C)+2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with greater than a specified % base pair mismatch will hybridize. Stringent hybridization conditions are commonly understood by those skilled in the art to be those experimental conditions that will allow less than or equal to about 30% base pair mismatch (i.e., at least about 70% identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 30% pair mismatch with a nucleic acid molecule of about 150 bp in length or greater, the following conditions could preferably be used. The unknown nucleic acid molecules would be attached to a support membrane, and the 150 bp probe would be labeled, e.g. with a radioactive tag. The hybridization reaction could be carried out in a solution comprising 2× SSC and 0% formamide, at a temperature of about 37° C. (low stringency conditions). Solutions of differing concentrations of SSC can be made by one of skill in the art by diluting a stock solution of 20× SSC (175.3 gram NaCl and about 88.2 gram sodium citrate in 1 liter of water, pH 7) to obtain the desired concentration of SSC. The skilled artisan would calculate the washing conditions required to allow up to 30% base pair mismatch. For example, assuming an average G+C content of the nucleic acid molecule to be hybridized of about 50%, and a wash solution comprising 1× SSC and 0% formamide, the $T_m$ of perfect hybrids would be about 85° C.:

$$81.5° C.+16.6 \log(0.15M)+(0.41\times0.37)-(500/150)-(0.61\times0)=85° C.$$

Thus, to achieve hybridization with nucleic acid molecules having about 30% base pair mismatch, hybridization washes would be carried out at a temperature of less than or equal to 55° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base pair mismatch will not vary significantly from 55° C. It is to be noted that the minimal size of a mite Group 1 nucleic acid molecule of the present invention is a size sufficient to allow the formation of a stable hybrid (i.e., hybridization under stringent hybridization conditions) with the complementary sequence of another nucleic acid molecule. As such, the minimal size of a mite Group 1 nucleic acid molecule of the present invention is from about 12 to about 18 nucleotides in length.

Furthermore, it is known in the art that there are commercially available computer programs for determining the degree of similarity between two nucleic acid or protein sequences. These computer programs include various known methods to determine the percentage identity and the number and length of gaps between hybrid nucleic acid molecules or proteins. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, the Wisconsin Package Version 9.0 sequence analysis software, available from Genetics Computer Group (GCG™), Madison, Wis.; DNAsis™, available from Hitachi Software, San Bruno, Calif.; and MacVector™, available from the Eastman Kodak Company, New Haven, Conn. A preferred method to determine percent identity among amino acid sequences and also among nucleic acid sequences includes using the GAP program with pair-wise comparisons within the GCG™ Wisconsin Package Version 9.0 sequence analysis software, hereinafter referred to as default parameters.

Preferred mite Group 1 proteins of the present invention include recombinant mite Group 1 proteins that are at least about 70%, preferably at least about 75%, more preferably at least about 80%, more preferably at least about 85%, more preferably at least about 90%, and even more preferably at least about 95% identical to amino acid sequences SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, and SEQ ID NO:44, and/or a protein comprising a fragment of any of these amino acid sequences, wherein the fragment has a function of selectively binding to IgE that binds native mite Group 1 protein and/or causing proliferation of a T cell that proliferates in response to a native mite Group 1 protein. A particularly preferred mite Group 1 protein includes at least a portion of at least one of the following amino acid sequences: SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, and/or SEQ ID NO:44. Also preferred is a protein comprising at least a portion of at least one protein encoded by an allelic variant of a nucleic acid molecule encoding a protein having at least one of the following sequences: SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, and/or SEQ ID NO:44. Such portions preferably have at least one of the following functions: selectively binding to IgE that binds native mite Group 1 protein and/or causing proliferation of a T cell that proliferates in response to a native mite Group 1 protein. It is to be noted that the proteins corresponding to SEQ ID NO:2, SEQ ID NO:5, SEQ ID NO:8, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, and/or SEQ ID NO:44 are, respectively, $PDerf1_{321}$, $PDerf1_{303a}$, $PDerf1_{223a}$, $PDerp1_{320}$, $PDerp1_{302}$, $PDerp1_{223}$, $PEurm1_{321}$, $PEurm1_{303}$, $PEurm1_{223}$, $PDerf1_{303b}$, $PDerf1_{223b}$, $PDerf1_{303c}$, $PDerf1_{303d}$, $PDerf1_{223c}$, and/or $PDerf_{223d}$.

Preferred nucleic acid molecules to use in encoding mite Group 1 proteins of the present invention are nucleic acid molecules that are at least about 70%, preferably at least about 75%, more preferably at least about 80%, more preferably at least about 85%, more preferably at least about 90%, more preferably at least about 95%, and even more preferably about 100% identical to nucleic acid sequences SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, and SEQ ID NO:43, and/or a fragment thereof, wherein such a fragment (a) hybridizes to a nucleic acid molecule having the complement of any of the listed nucleic acid sequences and/or (b) encodes a protein that selectively binds to IgE that binds native mite Group 1 protein and/or causes proliferation of a T cell that proliferates in response to a native mite Group 1 protein. Particularly preferred mite Group 1 nucleic acid molecules include at least one of the following nucleic acid sequences: SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, and SEQ ID NO:43, and fragments thereof. Also preferred are naturally occurring variants of such nucleic acid molecules, and fragments thereof. It is to be noted that SEQ ID NO:1, SEQ ID NO:4, SEQ ID NO:7, SEQ ID NO:10, SEQ ID NO:13, SEQ ID NO:16, SEQ ID NO:19, SEQ ID NO:22, SEQ ID NO:25, SEQ ID NO:28, SEQ ID NO:31, SEQ ID NO:34, SEQ ID NO:37, SEQ ID NO:40, and SEQ ID NO:43 are the coding strands of the following respective nucleic acid molecules: $nDerf1_{963}$, $nDerf1_{909a}$, $nDerf1_{669a}$, $nDerp1_{960}$, $nDerp1_{906}$, $nDerp1_{669}$, $nEurm1_{963}$, $nEurm1_{909}$, $nEurm1_{669}$, $nDerf11_{909b}$, $nDerf1_{669b}$, $nDerf1_{909c}$, $nDerf_{909d}$, $nDerf1_{669c}$, and/or $nDerf_{669d}$.

One embodiment of a method to produce a recombinant mite Group 1 protein of the present invention includes the steps of (a) culturing a methyltrophic yeast microorganism transformed with a nucleic acid molecule encoding the recombinant mite Group 1 protein, and (b) recovering the recombinant mite Group 1 protein from the methyltrophic yeast microorganism. A methyltrophic yeast microorganism is a yeast strain capable of using methanol as its sole carbon source. Although any methyltrophic yeast can be used in the methods of the present invention, preferred methyltrophic yeast microorganisms to transform and culture include those of the genera *Pichia, Hansenula, Torulopsis*, and *Candida*, with the genus *Pichia* being particularly preferred. Preferred methyltrophic yeast species include *Pichia pastoris, Pichia acaciae, Pichia anomala, Pichia augusta, Pichia capsulata, Pichia fabianii, Pichia farinosa, Pichia guilliermondii, Pichia methanolica, Pichia norvegensis, Pichia pinus, Pichia stipitis, Hansenula polymorpha*, and *Candida boidinii*. A preferred *Pichia* microorganism is *Pichia pastoris* Another embodiment of a method to produce a recombinant mite Group 1 protein of the present invention includes the steps of (a) culturing an *E. coli* microorganism transformed with a nucleic acid molecule encoding the recombinant mite Group 1 protein under conditions in which the protein forms an inclusion body in the *E. coli* microorganism, (b) isolating the inclusion body from the *E. coli* microorganism, and (c) recovering the recombinant mite Group 1 protein from the inclusion body. Such a recombinant mite Group 1 protein selectively binds to IgE of at least about 70% of IgE-containing serum samples that selectively bind to a native mite Group 1 protein.

Transformation of a nucleic acid molecule of the present invention into a microorganism can be accomplished by any method by which a nucleic acid molecule can be inserted into the cell. Transformation techniques include, but are not limited to, transfection, electroporation, microinjection, lipofection, adsorption, and protoplast fusion. Transformed nucleic acid molecules of the present invention can remain extrachromosomal or can integrate into one or more sites within a chromosome of the transformed (i.e., recombinant) microorganism in such a manner that their ability to be expressed is retained. A transformed microorganism is also referred to herein as a transformed cell, a recombinant microorganism or a recombinant cell.

A microorganism to be transformed can be either an untransformed cell or a cell that is already transformed with at least one nucleic acid molecule (e.g., one or more nucleic acid molecules encoding one or more proteins of the present invention and/or other proteins). A recombinant microorganism of the present invention is preferably produced by transforming a host cell with one or more recombinant molecules comprising one or more nucleic acid molecules of the present invention. Examples of recombinant microorganisms are provided herein.

As used herein, a recombinant molecule comprises a nucleic acid molecule of the present invention operatively linked to a transcription control sequence, preferably contained within an expression vector. The phrase operatively linked refers to joining of a nucleic acid molecule to a transcription control sequence in a manner such that the molecule is able to be expressed when transformed into a yeast or *E. coli* microorganism. As used herein, an expression vector is a DNA or RNA vector, typically either a plasmid or viral genome, that is capable of transforming a cell and of effecting expression of a specified nucleic acid molecule. A preferred recombinant molecule of the present invention contains regulatory sequences such as transcription control sequences, translation control sequences, origins of replication, and other regulatory sequences that are compatible with the recombinant microorganism and that control the expression of nucleic acid molecules of the present invention. In particular, recombinant molecules of the present invention at least include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant microorganisms of the present invention. A variety of such transcription control sequences are known to those skilled in the art; examples included, but are not limited to, tac, lac, trp, trc, oxy-pro, omp/lpp, rrnB, bacteriophage lambda (such as lambda $p_L$ (also referred to herein as lambda PL) and lambda $p_R$ (also referred to herein as lambda PR) and fusions that include such promoters), bacteriophage T7, T7lac, bacteriophage T3, bacteriophage SP6, SP01, alpha-mating factor, *Pichia* alcohol oxidase (AOX), antibiotic resistance gene, as other sequences capable of controlling gene expression in *E. coli* or methyltrophic yeast microorganisms; it is to be noted that this list is not intended to be limiting as many additional transcriptional control sequences are known. A particularly preferred recombinant molecule includes a nucleic acid molecule that encodes a mite Group 1 protein, operatively linked to the alcohol oxidase promoter AOX1. Another particularly preferred recombinant molecule includes a nucleic acid molecule that encodes a mite Group 1 protein operatively linked to the lambda PL promoter or the lambda PR promoter.

Recombinant molecules of the present invention can contain secretory signals (i.e., signal segment nucleic acid sequences) to enable an expressed fusion protein of the present invention to be secreted from the cell that produces the protein. Examples of suitable signal segments include any signal segment capable of directing the secretion of a protein of the present invention. Preferred signal segment sequences include, but are not limited to, mite Group 1 protein natural signal sequences and yeast alpha signal sequences, with the *S. cerevisiae* alpha signal sequence being particularly preferred for expression of a pro-form of a mite Group 1 protein in a methyltrophic yeast microorganism.

Another embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of mite Group 1 nucleic acid molecules of the present invention.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

One embodiment of a mite Group 1 protein of the present invention is a fusion protein. Suitable fusion segments for use with the present invention include, but are not limited to, segments that can: link two or more mite Group 1 proteins of the present invention to form multimers; enhance a protein's stability; facilitate the purification of a mite Group 1 protein; and/or to affect the immune response to a mite Group 1 protein. A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the mite Group 1 protein and can be susceptible to cleavage in order to enable straight-forward recovery of a mite Group 1 protein. Fusion proteins are preferably produced by culturing a recombinant cell transformed with a fusion nucleic acid molecule that encodes a protein including the fusion segment attached to either the carboxyl and/or amino terminal end of a mite Group 1 protein. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of -galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

An important discovery of the present invention are methods identified to produce recombinant mite Group 1 proteins having desirable functions. For example, culturing of a methyltrophic yeast microorganism transformed with a nucleic acid molecule encoding a pro-form of a mite Group 1 protein fused to an alpha factor signal sequence results in the production of a mature mite Group 1 protein exhibiting IgE reactivity comparable to that exhibited by the corresponding native mite Group 1 protein. Such culturing leads not only to expression of the pro-form of the protein but also to processing of the pro-form into the mature form. This result was unexpected in that *P. pastoris* expression of a cDNA encoding pro-cathepsin B, in contrast, yielded the pro-form of the enzyme which needed to be activated in vitro in the presence of acid; see, for example, Illy et al, 1997, *J Biol Chem* 272, 1197-1202, and references cited therein. In another example, culturing of an *E. coli* microorganism transformed with a nucleic acid molecule encoding a pro-form of a mite Group 1 protein results in the production of inclusion bodies comprising the pro-form, which is then recovered by solubilizing and refolding the protein. The recovered pro-form exhibits IgE reactivity that is at least 70% equivalent to that exhibited by the corresponding native mite Group 1 protein.

Effective culturing conditions to produce a recombinant mite Group 1 protein of the present invention include, but are not limited to, effective media, bioreactor, temperature, pH and oxygen conditions that permit protein production. An effective medium refers to any medium in which a cell is cultured to produce a mite Group 1 protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for methyltrophic yeast or *E. coli*. Such culturing conditions are within the expertise of one of ordinary skill in the art, and examples are provided in the Examples section.

Depending on the vector and host system used for production, resultant proteins of the present invention may either remain within the recombinant cell; be secreted into the culturing, or fermentation, medium; or be secreted into a space between two cellular membranes. In accordance with the present invention, recombinant mite Group 1 proteins produced by a methyltrophic yeast microorganism of the present invention are preferably secreted into the culturing medium, and recombinant mite Group 1 proteins produced by *E. coli* form inclusion bodies within the *E. coli* microorganism. As used herein, recovering a protein from a methyltrophic yeast microorganism refers to collecting the medium containing the yeast and the protein and need not imply additional steps of separation or purification. In a preferred embodiment, the protein is in the medium and, hence, can be easily separated from the yeast. Also, as used herein, the phrases isolating an inclusion body from an *E. coli* microorganism or recovering protein from the inclusion bodies do not imply any specified degree of separation or purification.

Proteins of the present invention can be purified using a variety of purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a diagnostic, therapeutic or prophylactic.

A preferred method to purify a mite Group 1 protein from a mite Group 1 transformed-methyltrophic yeast microorganism is to recover the medium in which the mite Group 1 transformed methyltrophic yeast microorganism was cultured, and then to purify the mite Group 1 protein using conventional chromatography techniques. Preferred is a method by which the culturing medium is subjected to ion-exchange chromatography. Preferred ion-exchange resins to use include cationic ion-exchange resins, particularly SP-Sepharose (available from Amersham-Pharmacia Biotech, Piscataway, N.J.) at about pH 4.5.

A preferred method to produce a recombinant mite Group 1 protein in *E. coli* is to culture a transformed *E. coli* microorganism of the present invention under conditions that cause the mite Group 1 protein to form an inclusion body within the microorganism. Such conditions are known in the art, and examples of such conditions are described in the Examples section, below. An inclusion body, as used herein, is a highly aggregated, insoluble form of a mite Group 1 protein present in the *E. coli* microorganism. These inclusion bodies are thought to contain mis-folded (i.e., improperly folded) denatured protein. Mite Group 1 protein inclusion bodies are then recovered by lysing the *E. coli* microorganisms. Methods to recover inclusion bodies and purify and refold *E. coli* expressed proteins are known in the art, see, for example, Deutscher, ed., 1990, *Guide to Protein Purification* Academic Press, San Diego, Calif., which is incorporated by reference herein in its entirety. Methods to lyse *E. coli* are known in the art, and include methods such as enzymatic lysis, mechanical lysis, and liquid shear lysis; see, for example, Deutscher, ibid. A preferred method to lyse transformed *E. coli* is by mechanical means, most preferably with a microfluidizer. Insoluble proteins can be recovered by centrifugation. To solubilize the insoluble proteins, a variety of reagents can be used. Suitable reagents include: guanidine-hydrochloride (HCl), preferably at a pH from about pH 7 to about pH 8 and at a concentration of from about 5 molar (M) to about 8 M; urea, preferably at a concentration of from about 6 M to about 8 M; sodium dodecyl sulfate; alkaline pH (greater than pH 9); and/or acetonitrile/propanol. Preferred methods to solubilize include use of 8 M urea in Tris buffer, pH 9.5, in 100 millimolar (mM) β-mercaptoethanol. Solubilized proteins can be refolded directly or subjected to additional purification step(s). A preferred method is to purify the mite Group 1 protein further before refolding. Any number of different types of resins suitable for protein purification may be used; preferred is an anion-exchange type resin such as, for example, Q-SEPHAROSE™ resin (available from Amersham-Pharmacia Biotech). To refold the solubilized protein directly or after purification, a number of methods are known in the art; see, for example, Deutscher, M. (1990), ibid. The term, refold, as used herein, refers to conditions in which reduced proteins can revert to their correct conformations, including restoring the correct disulfide bridges. Preferred methods to refold include (a) using glutathione to form mixed disulfides and/or (b) using high pH. For method (a), steps involved include: (i) reduction of the protein with a reducing agent, such as dithiothreitol, preferably 6 mM dithiothreitol for at least about 30 minutes; (ii) addition of oxidized glutathione, preferably at a concentration of from about 25 mM to about 100 mM, with about 25 mM being particularly preferred; (iii) dilution of the mixture to a urea concentration of preferably between about 0.5 M and 1 M, with 0.75 M urea being particularly preferred (assuming solubilization is conducted in the presence of urea) using a buffer, preferably 50 mM Tris, pH 9.5, with the addition of from about 5 mM to about 25 mM, preferably 6.5 mM, cysteine or reduced glutathione; (iv) incubation for about 10 to about 20 hours at 4° C.; and (v) dialysis against a buffer to remove urea; preferred buffers are phosphate buffered saline (PBS) at about pH 7.5 or 50 mM Tris-HCl, pH 7.5. For method (b), steps involved include: (i) adjusting pH of the solubilized protein to about pH 10; (ii) reducing the protein by treatment with 100 mM β-mercaptoethanol; and (iii) refolding by dialysis against PBS, pH 7.2 or 50 mM Tris-HCl, pH 7.5.

One embodiment of the present invention is a methyltrophic yeast microorganism comprising a mite Group 1 nucleic acid molecule of the present invention operatively linked to a transcription control sequence. Examples of suitable yeast strains, nucleic acid molecules and transcription control sequences are described herein. A preferred yeast is of the genus *Pichia*, with the species *Pichia pastoris* being even more preferred.

Another embodiment of the present invention is an isolated nucleic acid molecule comprising a nucleic acid sequence selected from the group consisting of SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, and/or SEQ ID NO:45. Also included are recombinant molecules that comprise a nucleic acid molecule selected from the group consisting of SEQ ID NO:28, SEQ ID NO:30, SEQ ID NO:31, SEQ ID NO:33, SEQ ED NO:34, SEQ ID NO:36, SEQ ID NO:37, SEQ ID NO:39, SEQ ID NO:40, SEQ ID NO:42, SEQ ID NO:43, and/or SEQ ID NO:45, operatively linked to a transcription control sequence. Examples of suitable transcription control sequences are described herein. Also included in the present invention is a recombinant microorganism comprising a nucleic acid molecule selected from the group consisting of SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, and SEQ ID NO:45. Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins). Host cells of the present invention either can be endogenously (i.e., naturally) capable of producing mite Group 1 proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Examples of host cells and transcription control sequences to be used in expression of such nucleic acid molecules include, but are not limited to, those disclosed in U.S. patent application Ser. No. 09/292,225, filed Apr. 15, 1999, by McCall el al (U.S. patent application Ser. No. 09,292,225); U.S. patent application Ser. No. 09/292,225, ibid., is incorporated by reference herein in its entirety. Preferred host cells and transcription control sequences include bacterial and yeast cells and control sequences, with *E. coli* and methyltrophic yeast, and particularly those methyltrophic yeast genera and species disclosed herein, being more preferred.

Another embodiment of the present invention is an isolated protein having the amino acid sequence SEQ ID NO:38 and/or SEQ ID NO:41. The present invention also includes nucleic acid molecules encoding such proteins, as well as recombinant molecules and recombinant cells comprising such nucleic acid molecules.

One embodiment of the present invention is a method to detect mite allergy in an animal, which includes the steps of: (a) contacting an isolated mite Group 1 protein produced in accordance with the present invention with a putative IgE-containing substance under conditions suitable to form a complex between the mite group 1 protein and IgE (i.e., a mite Group 1 protein:IgE complex); and (b) determining the presence of IgE reactive with the mite Group 1 protein by detecting the complex, wherein presence of reactive IgE is indicative of mite allergy in the animal. Presence of such a mite Group 1 protein:IgE complex (i.e. a complex between IgE and a mite Group 1 protein of the present invention) indicates that the animal is producing IgE reactive with mite Group 1 protein and, as such, the animal is suffering from mite allergy or is susceptible to mite allergy. Preferred IgE to detect using a mite Group 1 protein include any mammalian IgE, with human IgE, canine IgE, feline IgE, equine IgE, murine IgE and rat IgE being more preferred, with human and canine IgE being particularly preferred.

Animals in which to detect IgE include mammals and birds, with humans, dogs, cats, horses and other pets, work and/or economic food animals being preferred. Particularly preferred animals in which to detect IgE are humans and dogs. As used herein, canine refers to any member of the dog family, including domestic dogs, wild dogs and zoo dogs. Examples of dogs include, but are not limited to, domestic dogs, wild dogs, foxes, wolves, jackals and coyotes. As used herein, feline refers to any member of the cat family, including domestic cats, wild cats and zoo cats. Examples of cats include, but are not limited to, domestic cats, wild cats, lions, tigers, leopards, panthers, cougars, bobcats, lynx, jaguars, cheetahs, and servals. As used herein, equine refers to any member of the horse family, including, but are not limited to, domestic horses, wild horses and zoo horses.

As used herein, the term "contacting" refers to combining or mixing, in this case a putative IgE-containing substance with a mite Group 1 protein. Formation of a complex between a mite Group 1 protein and an IgE refers to the ability of the mite Group 1 protein to selectively bind to the IgE in order to form a stable complex that can be measured (i.e., detected, determined). As used herein, the term selectively binds to an IgE refers to the ability of a mite Group 1 protein of the present invention to preferentially bind to IgE, without being able to substantially bind to other antibody isotypes. Binding between a mite Group 1 protein and an IgE is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, Sambrook et al., ibid. Examples of immunological assays are disclosed in, for example, Price, C. and Newman, D., eds, *Principles and Practice of Immunoassay,* 2nd Edition, (1997) Stockton Press, New York, N.Y., which is incorporated by reference herein in its entirety.

As used herein, the term detecting complex formation refers to determining if any complex is formed, i.e., assaying for the presence (i.e., existence) of a complex. If complexes are formed, the amount of complexes formed can, but need not be, determined. Complex formation, or selective binding, between mite Group 1 protein and any IgE in the substance can be measured (i.e., detected, determined) using a variety of methods standard in the art (see, for example, Sambrook et al. ibid), examples of which are disclosed herein.

As used herein a putative IgE-containing substance is any material in which IgE antibodies may exist. In one embodiment, a putative IgE-containing substance of the present invention includes a biological sample from an animal. A suitable biological sample includes, but is not limited to, a bodily fluid substance or a cellular substance. A bodily fluid refers to any fluid that can be collected (i.e., obtained) from an animal, examples of which include, but are not limited to, blood, serum, plasma, urine, tears, aqueous humor, cerebrospinal fluid (CSF), saliva, lymph, nasal secretions, tracheobronchial aspirates, milk, feces and fluids obtained through bronchial alveolar lavage. Such a IgE-containing substance of the present invention can, but need not be, pretreated to remove at least some of the non-IgE isotypes of immunoglobulin and/or other proteins, such as albumin, present in the fluid. Such removal can include, but is not limited to, contacting the bodily fluid with a material, such as Protein G, to remove IgG antibodies and/or affinity purifying IgE antibodies from other components of the body fluid by exposing the fluid to, for example, Concanavalin A. In another embodiment, a substance includes collected bodily fluid that is pretreated to concentrate immunoglobulin contained in the fluid. For example, immunoglobulin contained in a bodily fluid can be precipitated from other proteins using ammonium sulfate. A preferred IgE-containing substance of the present invention is serum.

A complex can be detected in a variety of ways including, but not limited to use of one or more of the following assays: an enzyme-linked immunoassay, a radioimmunoassay, a fluorescence immunoassay, a chemiluminescent or other luminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, a BioCore™ assay (e.g., using colloidal gold) and an immunoblotting assay (e.g., a western blot). Such assays are well known to those skilled in the art. Assays can be used to give qualitative or quantitative results depending on how they are used. Some assays, such as agglutination, particulate separation, and immunoprecipitation, can be observed visually (e.g., either by eye or by a machines, such as a densitometer or spectrophotometer) without the need for a detectable marker. In other assays, conjugation (i.e., attachment) of a detectable marker to a mite Group 1 protein or to a molecule that selectively binds to the IgE being detected aids in detecting complex formation. Examples of detectable markers include, but are not limited to, a radioactive label, a fluorescent label, a chemiluminescent or other luminescent label, a chromophoric label or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), a luciferase, and biotin-related compounds or avidin-related compounds (e.g., streptavidin or ImmunoPure® NeutrAvidin).

In one embodiment a complex can be formed and detected in solution. In another embodiment, a complex can be formed in which one or more members of the complex are immobilized on (e.g., coated onto) a support substrate. Immobilization techniques are known to those skilled in the art. Suitable support substrate materials include, but are not limited to, plastic, glass, gel, celluloid, paper, PVDF (poly-vinylidene-fluoride), nylon, nitrocellulose, and particulate materials such as latex, polystyrene, nylon, nitrocellulose, agarose and magnetic resin. Suitable shapes for support substrate material include, but are not limited to, a well (e.g., microtiter dish well), a plate, a dipstick, a bead, a lateral flow apparatus, a flow-through apparatus, a membrane, a filter, a tube, a dish, a celluloid-type matrix, a magnetic particle, and other particulates. A particularly preferred support substrate comprises an ELISA plate, a dipstick, a radioimmunoassay plate, agarose beads, plastic beads, latex beads, immunoblot membranes and immunoblot papers. In one embodiment, a support substrate, such as a particulate, can include a detectable marker.

A preferred method to detect IgE is an immunosorbent assay. An immunoabsorbent assay of the present invention comprises a capture molecule and an indicator molecule. A capture molecule of the present invention binds to an IgE in such a manner that the IgE is immobilized to a support substrate. As such, a capture molecule is preferably immobilized to a support substrate of the present invention prior to exposure of the capture molecule to a putative IgE-containing substance. As such, an indicator molecule preferably is not immobilized to the same support substrate as a capture molecule prior to exposure of the capture molecule to a putative IgE-containing substance.

In one embodiment, a mite Group 1 protein of the present invention, also referred to as a mite Group 1 antigen or allergen of the present invention, is used as a capture molecule by being immobilized on a support substrate, such as a microtiter dish well or a dipstick. A biological sample collected from an animal is applied to the support substrate and incubated under-conditions suitable (i.e., sufficient) to allow for antigen:IgE complex formation bound to the support substrate (i.e., IgE in a sample binds to a mite Group 1 protein immobilized on a support substrate). Excess non-bound material (i.e., material from the biological sample that has not bound to the antigen), if any, is removed from the support substrate under conditions that retain antigen:IgE complex binding to the support substrate. Preferred conditions are generally disclosed in Sambrook et al., ibid. A detection molecule is added and incubated to allow formation of a complex between the detection molecule and the antigen:IgE complex. Excess detection molecule is removed, a developing agent is added if required, and the complex is submitted to a detection device for analysis. A preferred detection molecule for this embodiment is an IgE-binding molecule, such as an anti-IgE isotype or idiotype antibody, or other molecule that selectively binds IgE, for example an IgE receptor ($Fc_\epsilon R$) protein or alpha chain protein thereof, examples of which are described in, for example, U.S. Pat. No. 5,945,294, issued Aug. 31, 1999, by Frank et al. (U.S. Pat. No. 5,945,294); U.S. Pat. No. 5,958,880, issued Sep. 28, 1999, by Frank et al. (U.S. Pat. No. 5,958,880); PCT Patent Publication No. WO 98/45707, published Oct. 15, 1998, by Frank et al. (WO 98/45707); PCT Patent Publication No. WO 99/38974, published Aug. 5, 1999, by Weber et al. (WO 99/38974); and U.S. patent application Ser. No. 09/287,380, filed Apr. 6, 1999, by deWeck et al. (U.S. patent application Ser. No. 09/287,380); each of these issued patents, patent applications, and patent publications is incorporated by reference herein in its entirety. A detection molecule is preferably conjugated to a detectable marker such as those disclosed herein. Also included in the present invention is the use of multiple reagents to amplify a signal, such as secondary or tertiary antibodies or other binding molecules.

In one embodiment, an anti-IgE antibody (e.g., isotype or idiotype specific antibody) is used as a capture molecule by being immobilized on a support substrate, such as a microtiter dish well or a dipstick. A biological sample collected from an animal is applied to the support substrate and incubated under conditions suitable to allow for anti-IgE antibody:IgE complex formation bound to the support substrate. Excess non-bound material, if any, is removed from the support substrate under conditions that retain anti-IgE antibody:IgE complex binding to the support substrate. A mite Group 1 protein is added to the support substrate and incubated to allow formation of a complex between the mite Group 1 protein and the anti-IgE antibody:IgE complex. Preferably, the mite Group 1 protein is conjugated to a detectable marker such as those disclosed herein. Excess mite Group 1 protein is removed, a developing agent is added if required, and the sample is submitted to a detection device for analysis. One or more antibody layers can also be used to detect mite Group 1 protein binding.

In one embodiment, an immunosorbent assay of the present invention does not utilize a capture molecule. In this embodiment, a biological sample collected from an animal is applied to a support substrate, such as a microtiter dish well or a dipstick, and incubated under conditions suitable to allow for IgE binding to the support substrate. Any IgE present in the bodily fluid is immobilized on the support substrate. Excess non-bound material, if any, is removed from the support substrate under conditions that retain IgE binding to the support substrate. A mite Group 1 protein is added to the support substrate and incubated to allow formation of a complex between the mite Group 1 protein and the IgE. Preferably, the mite Group 1 protein is conjugated to a detectable marker. Excess mite Group 1 protein is removed, a developing agent is added if required, and the sample is submitted to a detection device for analysis.

Another preferred method to detect IgE is a lateral flow assay, examples of which are disclosed in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; each of these patent publications is incorporated by reference herein in its entirety. In one embodiment, a biological sample is placed in a lateral flow apparatus that includes the following components: (a) a support structure defining a flow path; and (b) a labeling reagent comprising a labeled (e.g., colored) bead conjugated to a mite Group 1 protein of the present invention, the labeling reagent being impregnated within the support structure in a labeling zone; and (c) a capture reagent comprising an IgE-binding molecule, such as an anti-IgE antibody or an IgE receptor protein or alpha chain protein thereof. Preferred mite Group 1 proteins include those disclosed herein. It is to be noted that in another embodiment, the labeling reagent include an IgE-binding molecule and the capture reagent can be a mite Group 1 protein of the present invention. In either embodiment, the capture reagent is located downstream of the labeling reagent within a capture zone fluidly connected to the labeling zone in such a manner that the labeling reagent can flow from the labeling zone into the capture zone. The support structure defines a flow path that is lateral and includes a capture zone. The apparatus can further comprise a sample receiving zone located along the flow path, more preferably upstream of the capture reagent. The flow path in the support structure is created by contacting a portion of the support structure downstream of the capture zone, preferably at the end of the flow path, to an absorbent capable of absorbing excess liquid.

Another preferred method to detect IgE is a flow through assay, examples of which are disclosed in U.S. Pat. No. 4,727,019, issued Feb. 23, 1988, by Valkirs et al, which is incorporated by reference in its entirety. In one embodiment, a biological sample is placed in a flow through apparatus that includes the following components: (a) a porous solid phase having lower and upper surfaces arranged so that the biological sample is applied to the upper surface, the upper surface also including a test area that includes a capture reagent; and (b) an absorbent phase contacting the lower surface of the solid that collects liquid from the biological sample that has permeated the solid phase. The capture reagent can be either a mite Group 1 protein of the present invention or an IgE-binding molecule. After the sample flows through the apparatus, a detection reagent is added to the apparatus such that any captured IgE can be detected. Examples of detection reagents include (a) a mite Group 1 protein of the present invention, which is used when the capture reagent used is an IgE-binding molecule and (b) an IgE-binding molecule, which is used when the capture reagent used is a mite Group 1 protein. Detection is accomplished using means known to those skilled in the art.

The present invention also includes a kit to detect mite allergy in an animal, based on each of the disclosed detection methods. Suitable and preferred mite Group 1 proteins are disclosed herein. One embodiment is a kit to detect IgE specific for mite Group 1 proteins comprising a mite Group 1 protein and a means for detecting an IgE antibody that selectively binds to a mite Group 1 protein. Suitable means of detection include compounds disclosed herein that bind to either the mite Group 1 protein, such as an anti-mite Group 1 protein antibody, or to IgE, such as an antibody that selectively bind to IgE (an anti-IgE antibody) or an IgE receptor protein or alpha chain protein thereof. In one embodiment, a kit also includes one or more additional antigens to determine if an animal is susceptible to or suffers from allergy to such antigen(s). Examples of such allergens include, but are not limited to, those disclosed in U.S. Pat. No. 5,945,294, ibid.; U.S. Pat. No. 5,958,880, ibid; WO 98/45707, ibid; WO 99/38974, ibid.; and U.S. patent application Ser. No. 09/287,380, ibid.

Additional teachings with respect to methods and kits to detect allergy to Group 1 proteins can be found, for example, in U.S. Pat. No. 5,646,115, issued Jul. 8, 1997, by Frank et al. (U.S. Pat. No. 5,646,115); U.S. Pat. No. 5,840,695, issued Nov. 24, 1998, by Frank et al. (U.S. Pat. No. 5,840,695); U.S. Pat. No. 5,932,470, issued Aug. 3, 1999, by Frank et al. (U.S. Pat. No. 5,932,470); U.S. Pat. No. 5,945,294, ibid; U.S. Pat. No. 5,958,880, ibid.; WO 98/45707, ibid.; WO 99/38974, ibid.; and U.S. patent application Ser. No. 09/287,380, ibid. U.S. Pat. No. 5,646,115, ibid., U.S. Pat. No. 5,840,695, ibid., and U.S. Pat. No. 5,932,470 are each incorporated by reference herein in its entirety.

One embodiment of the present invention is a composition that, when administered to an animal in an effective manner, is capable of reducing an allergic response to a mite Group 1 protein in a mite Group 1 protein allergic animal. Such a composition can function as a preventative, or prophylactic, or as a therapeutic, or treatment. Such a composition includes an isolated mite Group 1 protein of the present invention and at least one of the following components: an excipient, an adjuvant, and a carrier that the animal can tolerate. Examples of excipients, adjuvants and carriers are found throughout the art; see, for example, U.S. Pat. No. 5,958,880, ibid. and U.S. Pat. No. 5,840,695, ibid.

In one embodiment, a mite Group 1 protein of the present invention can be genetically engineered or otherwise altered to lessen or completely abolish a mite Group 1 protein's ability to bind to IgE. Such a molecule, referred to herein as a mite Group 1 protein of the present invention with reduced IgE reactivity, can be used to reduce an animal's allergic response to exposure to a mite Group 1 protein.

Suitable protocols by which to administer compositions of the present invention in an effective manner can vary according to individual dose size, number of doses, frequency of dose administration, and mode of administration. Determination of such protocols can be accomplished by those skilled in the art. An effective dose refers to a dose capable of treating an animal against hypersensitivity to mite allergens. Effective doses can vary depending upon, for example, the composition used and the size and type of the recipient animal, i.e. what species. Effective doses to immunomodulate an animal against a mite Group 1 protein include doses administered over time that are capable of alleviating a hypersensitive response by an animal to a mite Group 1 protein. For example, a first tolerizing dose can comprise an amount of a composition of the present invention that causes a minimal hypersensitive response when administered to a hypersensitive animal. A second tolerizing dose can comprise a greater amount of the same composition than the first dose. Effective tolerizing doses can comprise increasing concentrations of the composition necessary to tolerize an animal such that the animal does not have a hypersensitive response to exposure to a mite Group 1 protein. An effective dose to desensitize an animal can comprise a concentration of a composition of the present invention sufficient to block an animal from having a hypersensitive response to exposure to a mite allergen present in the environment of the animal. Effective desensitizing doses can include repeated doses having concentrations of a composition that cause a minimal hypersensitive response when administered to a hypersensitive animal.

A suitable single dose is a dose that is capable of treating an animal against hypersensitivity to a mite Group 1 protein when administered one or more times over a suitable time period. For example, a preferred single dose of a mite Group 1 protein-containing composition is from about 0.5 nanograms (ng) to about 1 gram (g) of the protein per kilogram body weight of the animal. Further treatments with the composition can be administered from about 1 day to 1 year after the original administration. Further treatments with the composition preferably are administered when the animal is no longer protected from hypersensitive responses to mite Group 1 proteins. Particular administration doses and schedules can be developed by one of the skill in the art based upon the parameters discussed above. Modes of administration can include, but are not limited to, subcutaneous, intradermal, intravenous, nasal, oral, transdermal and intramuscular routes.

A composition of the present invention can be used in conjunction with other compounds capable of modifying an animal's hypersensitivity to mite allergens. For example, an animal can be treated with compounds capable of modifying the function of a cell involved in a hypersensitive response, compounds that reduce allergic reactions, such as by systemic agents or anti-inflammatory reagents (e.g. anti-histamines, anti-steroid reagents, anti-inflammatory reagents and reagents that drive immunoglobulin heavy chain class switching from IgE to IgG). Suitable compounds useful for modifying the function of a cell involved in a hypersensitive response include, but are not limited to, antihistamines, cromolyn sodium, theophylline, cyclosporin A, adrenalin, cortisone, compounds capable of regulating cellular signal transduction, compounds capable of regulating adenosine 3',5' cyclic phosphate (cAMP) activity, and compounds that block IgE activity, such as peptides from IgE or IgE specific Fc receptors, antibodies specific for peptides from IgE or IgE-specific Fc receptors, or antibodies capable of blocking binding of IgE to Fc receptors.

A composition of the present invention can also be used in conjunction with other antigens to prevent or treat allergic, infectious, or other diseases. Examples of antigens causing allergy include, but are not limited to those disclosed in U.S. Pat. No. 5,945,294, ibid.; U.S. Pat. No. 5,958,880, ibid; WO 98/45707, ibid.; WO 99/38974, ibid.; and U.S. patent application Ser. No. 09/287,380, ibid.

Additional teachings with respect to compositions and uses thereof to reduce allergy can be found, for example, in U.S. Pat. No. 5,958,880, ibid. and U.S. Pat. No. 5,840,695, ibid.

The following examples are provided for the purposes of illustration and are not intended to limit the scope of the present invention. The following examples include a number of recombinant DNA and protein chemistry techniques known to those skilled in the art; see, for example, Sambrook et al., ibid.

EXAMPLES

Example 1

This Example describes the production of certain novel mite Group 1 nucleic acid molecules and proteins of the present invention. This Example also describes expression of such nucleic acid molecules and proteins by recombinant *Pichia* microorganisms of the present invention.

A. This example describes the production and expression in *Pichia* of a Der f 1 Group 1 cDNA nucleic acid molecule, denoted herein as nDerf1$_{909b}$, the coding strand of which, represented by SEQ ID NO:28, incorporates *Pichia*-preferred codon changes as compared to nDerf1$_{909a}$, having a coding strand nucleic acid sequence of SEQ ID NO:4. Nucleic acid molecule nDerf1$_{909b}$ encodes a pro-form of a Der f 1 Group 1 protein, namely PDerf1$_{303b}$. The following codon changes were made to produce nDerf1$_{909b}$ from nDerf1$_{909a}$: a change from CGA to AGA in the codon spanning nucleotide positions 538 to 540 of SEQ ID NO:4; a change from CGA to AGA in the codon spanning nucleotide positions 547 to 549 of SEQ ID NO:4; a change from CGA to AGA in the codon spanning nucleotide positions 553 to 555 of SEQ ID NO:4; and a change from CGA to AGA in the codon spanning nucleotide positions 556 to 558 of SEQ ID NO:4. Translation of the resultant coding strand having SEQ ID NO:28 yielded SEQ ID NO:29, also represented as PDerf1$_{303b}$. SEQ ID NO:30 represents the reverse complement of SEQ ID NO:28, i.e., the complementary strand of nDerf1$_{909b}$.

Specifically, nucleic acid molecule nDerf1$_{909b}$ was produced as follows. Two sets of two primers each were designed to allow for selective optimization of four closely situated arginine codons and to provide a signal peptide (the *S. cerevisiae* alpha factor) coding sequence for efficient secretion of the expressed protein from *P. pastoris*. The first set of two primers, the first being sense primer 5'CGC GTC CCT CTC GAG AAA AGA GAG GCT AGA CCA GCT TCA ATC AAA 3' (SEQ ID NO:46) and the second being the antisense primer 5'GGG CTT TCC TTT TGC GGC CGC TCA CAT GAT TAC AAC ATA TGG 3' (SEQ ID NO:47), incorporate XhoI and NotI cloning sites (shown in bold) to facilitate cloning into an *E. coli/P. pastoris* shuttle plasmid, pPICZalphaB (available from Invitrogen Corp., Carlsbad, Calif.), such that the Der f 1 nucleic acid molecule would be operatively linked to the *P. pastoris* AOX promoter. Primer SEQ ID NO:46 was constructed to join nucleotides encoding the following amino acid segments: the C-terminal portion of the *S. cerevisiae* alpha peptide (LEU-GLU), the KEX2 cleavage site (LYS-ARG), and a GLU-ALA spacer sequence to the first residue (ARG) of the Der f 1 pro-protein. The second set of primers, the first being sense primer 5' GCA AGA GAA CAA AGA TGC AGA AGA CCA AAT TCG C 3' (SEQ ID NO:48), and the second being 5'GCG AAT TTG GTC TTC TGC ATC TTT GTT CTC TTG C 3' (SEQ ID NO:49), overlap on opposite strands of the nucleotide sequence for SEQ ID NO:4 and change CGA, an infrequently used arginine codon for yeast, to AGA, the most abundant codon for this residue. The changed codons for SEQ ID NO:48 are in bold. The approximately 950-nucleotide PCR product was generated by a three step process. In the first step, primers SEQ ID NO:46 and SEQ ID NO:49 were combined with a *D. farinae* cDNA library prepared as described in U.S. patent application Ser. No. 09,292,225, ibid., to produce an approximately 600-nucleotide fragment. The PCR reaction included the following reactants in a 50 microliter (μl) reaction volume: 2 μl *D. farinae* cDNA library, 1×PFU polymerase buffer (available from Stratagene, LaJolla, Calif.), 0.2 mM each of the four dNTPs and 2.5 Units PFU polymerase (all available from Stratagene), 0.5 micromolar (μM) of the primers having SEQ ID NO:46 and SEQ ID NO:49. Amplification conditions were as follows: 1 cycle of 96° C. for 3 minutes, then 30 cycles of the following: 96° C. for 1 minute, 55° C. for 1 minute, 72° C. for 2 minutes; followed by 1 cycle of 72° C. for 7 minutes. A second PCR reaction, using the aforementioned conditions and primers having SEQ ID NO:48 and SEQ ID NO:47, was performed resulting in an approximately 400-nucleotide product. The two PCR products were gel purified, annealed together to form a template for a third round of PCR using the conditions specified previously. The resulting approximately 900-nucleotide product was gel purified, digested with XhoI and NotI, ligated into similarly digested pPICZalphaB, and transformed into *E. coli* strain DH5alpha to create plasmid pBC128, also referred to herein as recombinant molecule pBC128. The plasmid was linearized at a unique SacI site and introduced into *P. pastoris* strain X33 by electroporation as described by Guarente et al., 1991 *Methods Enzymol* 194, 182-187. Recombinant cells resistant to 1 milligram/milliliter (mg/ml) zeocin, presumed to have multiple integrated copies of the linearized plasmid pBC128, were selected. Integration of the expression cassette into the *P. pastoris* genome was confirmed by PCR. Expression, using techniques known to those skilled in the art, of representative zeocin-resistant recombinant *P. pastoris* microorganisms were evaluated after induction with methanol for two days. One recombinant cell, denoted *P. pastoris* HCY215, was found to express relatively high levels of a protein of the appropriate molecular weight by sodium dodecyl sulfate (SDS) polyacrylamide gel electrophoresis (PAGE) and silver staining, using methods known in the art.

B. This example describes the production and expression in *Pichia* of a Der f 1 Group 1 cDNA nucleic acid molecule, denoted herein as nDerf1$_{669b}$, the coding strand of which, represented by SEQ ID NO:31, incorporates *Pichia*-preferred codon changes as compared to nDerf1$_{669a}$, having a coding strand nucleic acid sequence of SEQ ID NO:7. Nucleic acid molecule nDerf1$_{669b}$ encodes a mature form of a Der f 1 Group 1 protein, namely PDerf1$_{223b}$, represented by SEQ ID NO:32. SEQ ID NO:33 represents the complementary strand of nucleic acid molecule nDerf1$_{669b}$.

An expression plasmid encoding the mature form of Der f 1 with codons altered for optimized expression in *P. pastoris* was produced using recombinant molecule pBC128 (produced as described in Example 1A) as template. pBC128 was submitted to PCR mutagenesis using primers SB11 (sense primer with nucleic acid sequence CGC ATA GTC CCT CTC GAG AAA AGA ACA AGC GCT TGC CGT ATC, SEQ ID NO:54) and the primer with SEQ ID NO:47. Primer SEQ ID NO:54 incorporates a 5-prime XhoI restriction site (shown in bold) and fuses the first codon of nDerf1$_{669b}$ in frame with the nucleic acid sequence encoding the KEX2 cleavage site (LYS-ARG) of pPICZAlphaA. A single round of PCR amplification was performed in a 50-μl reaction volume using conditions as described in Example 1A with 50 ng of plasmid pBC128 (containing nDerfl$_{909b}$, the coding strand of which is represented by SEQ ID NO:28) as template and primers SEQ ID NO:54 and SEQ ID NO:47. The PCR product, denoted herein as plasmid pBC138, or recombinant molecule pBC138, is identical to pBC128 except that pBC138 contains nDerfl$_{669b}$ instead of nDerfl$_{909b}$ and, as such, lacks nucleic acid sequences encoding the 80-residue "pro" peptide of Der f 1. The specific codon changes in nDerfl$_{669b}$ (with a coding strand nucleic acid sequence of SEQ ID NO:31) as compared to nDerfl$_{669a}$ (with a coding strand nucleic acid sequence of SEQ ID NO:7) which encodes a wild-type *D. farinae* mature-form Group 1 protein, are as follows: changes from CGA to AGA in the codons spanning nucleotide positions (a) 298 to 300, (b) 307 to 309, (c) 313 to 315, and (d) 316-318 of SEQ ID NO:7. Recombinant molecule pBC138 was linearized with SacI, electroporated into competent *P. pastoris* strain X33 cells, and a zeocin-resistant recombinant cell, denoted herein as HCY286 was selected as described in Example 1A.

C. This example describes the production and expression in *Pichia* of a Der f 1 Group 1 cDNA nucleic acid molecule, denoted herein as nDerfl$_{909d}$, the coding strand of which, represented by SEQ ID NO:37, incorporates *Pichia*-preferred codon optimization changes as well as a codon change that removes an N-glycosylation site, as compared to nDerfl$_{909a}$, having a coding strand nucleic acid sequence of SEQ ID NO:4. The Der f 1 pro-form protein PDerfl$_{303a}$ (SEQ ID NO:5) contains a single N-glycosylation site (NTS) at residues 133-135 of SEQ ID NO:5. An expression plasmid encoding a non-glycosylated pro-form of Der f 1 with codons altered for optimized expression in *P. pastoris* was produced by inverse mutagenesis using recombinant molecule pBC128 (produced as described in Example 1A) containing nucleic acid molecule nDerfl$_{909b}$ as template. The resulting recombinant molecule contained the mutated nucleic acid molecule nDerfl$_{909d}$, a Der f 1 nucleic acid molecule in which the codon encoding asparagine (AAC) spanning nucleotides 397 to 399 of SEQ ID NO:28 was altered to encode glutamine (CAA) at the same positions in SEQ ID NO:37. Nucleic acid molecule nDerfl$_{909d}$ encodes a pro-form of a Der f 1 Group 1 protein lacking any N-glycosylation sites, namely PDerfl$_{303d}$, represented by SEQ ID NO:38. SEQ ID NO:39 represents the complementary strand of nucleic acid molecule nDerfl$_{909d}$.

The PCR reaction included the following components in a 50-μl reaction volume: 25 ng nDerfl$_{909b}$-containing plasmid pBC128, 1× PFU polymerase buffer, 0.2 mM each of the four dNTPs, 2.5 U PFU polymerase, 0.5 μM primer SEQ ID NO:57 and SEQ ID NO:58. Primers SEQ ID NO:57 (sense primer corresponding to nucleotides (5'GCCGCAACTG AATCAGCTTA TTTGGCCTAC CGTCAAACGT CTTTGG 3') and SEQ ID NO:58 (antisense primer corresponding to nucleotides 5'GACACCAGAG AAAGC- CCAAC ATGAACCACA GCCTCCTTGC ATACG 3') contain 5-prime phosphates and are situated end-to-end on opposite strands of the DNA template. Primer SEQ ID NO:57 changes an asparagine codon (AAC) to glutamine (CAA); the relevant nucleotides are shown in bold in the above primer sequence. The amplification conditions were: 1 cycle of 96° C. for 3 min, 30 cycles of 96° C. for 1 min, 55° C. for 1 min, 72° C. for 9 min, and 1 cycle of 72° C. for 7 min. The amplified product was desalted and self-ligated to form recombinant molecule pBC158, which contains nDerfl$_{909d}$, the coding strand of which is represented by SEQ ID NO:37. Recombinant molecule pBC158 was linearized with SacI, electroporated into competent *P. pastoris* strain X33 cells, and a zeocin-resistant recombinant cell, denoted herein as HCY288 was selected as described in Example 1A. Expression of recombinant cell HCY288 under conditions as described in Example 1A yielded PDerfl$_{303d}$, which when submitted to SDS-PAGE migrated in a manner similar to that of a non-glycosylated protein.

D. This example describes the production and expression in *Pichia* of a Der f 1 Group 1 cDNA nucleic acid molecule, denoted herein as nDerfl$_{669c}$, the coding strand of which, represented by SEQ ID NO:40, incorporates *Pichia*-preferred codon optimization changes as well as a codon change that removes an N-glycosylation site, as compared to nDerfl$_{669a}$, having a coding strand nucleic acid sequence of SEQ ID NO:7. The Der f 1 mature protein PDerfl$_{223a}$. (SEQ ID NO:8) contains a single-glycosylation site (NTS) at residues 53-55 of SEQ ID NO:8. An expression plasmid encoding a non-glycosylated mature form of Der f 1 with codons altered for optimized expression in *P. pastoris* is produced from recombinant molecule pBC158, produced as described in Example 1C, using a strategy as described in Example 1B. That is, pBC158 is submitted to PCR amplification in the presence of primers having SEQ ID NO:47 and SEQ ID NO:54 under conditions as described in Example 1B. The resultant recombinant molecule, denoted herein as pBC168, contains mutated nucleic acid molecule nDerfl$_{669c}$, a Der f 1 nucleic acid molecule in which the codon corresponding to that encoding asparagine (AAC) spanning nucleotides 397 to 399 of SEQ ID NO:28 is altered to encode glutamine (CAA) in SEQ ID NO:40. As such, nucleic acid molecule nDerfl$_{669c}$ encodes a mature form of a Der f 1 Group 1 protein lacking any N-glycosylation sites, namely PDerfl$_{223d}$, represented by SEQ ID NO:41. SEQ ID NO:41 has a Q rather than N at amino acid residue 53. SEQ ID NO:42 represents the complementary strand of nucleic acid molecule nDerfl$_{669c}$.

Recombinant molecule pBC168 is linearized with SacI, electroporated into competent *P. pastoris* strain X33 cells, and a zeocin-resistant recombinant cell selected as described in Example 1A.

Example 2

This Example describes the expression and purification of certain recombinant mite Group 1 proteins of the present invention from supernatant cultures of recombinant *Pichia* microorganisms.

Recombinant *P. pastoris* microorganisms, also denoted herein as strains, were routinely cultured on YPD culture medium (1% yeast extract, 2% peptone, 2% dextrose). His+ transformants were selected on MD culture medium (1.34% yeast nitrogen base, 0.00004% biotin, 2% dextrose). Small-scale inductions of expression of recombinant *P. pastoris* strains containing Derf1 nucleic acid molecules were performed using BMG or BMM culture media which were composed of the following: 100 mM potassium phosphate, pH 6.0, 1.34% yeast nitrogen base, 0.00005% biotin and either 1% glycerol (BMG) or 0.5% methanol (BNM). For each recombinant strain grown and induced, a single colony of that strain was inoculated into 25 ml BMG culture medium in a 250 ml baffled flask covered with a porous silicon rubber stopper to allow maximum aeration. The culture was grown at 28° C. with shaking to an optical density (A600) of about 1.0. The culture was then pelleted for 10 min at 3000×g (times gravity) and resuspended in 250 ml BMM culture medium at an optical density (A600) of about 1.0 in a 2-liter (L) baffled flask with a porous silicon rubber stopper to induce expression of a Der f 1 nucleic acid molecule operatively linked to the AOX promoter. The culture was incubated at 28° C. for 4 days; methanol was added daily to a final concentration of 0.5% volume/volume (v/v). The entire culture volume was concentrated to 20% of original volume by tangential flow filtration (3000 MW cutoff, available from AG Technologies Needham, Mass.) and analyzed by SDS-PAGE.

The supernatant from the culture was recovered and diluted 1:3 (v/v) with 25 mM sodium acetate pH 4.5 (Buffer A) and loaded onto a 1.6×10 mm SP-Sepharose (available from Amersham-Pharmacia Biotech, Piscataway, N.J.) previously equilibrated with 25 mM sodium acetate, pH 4.5. Bound protein was eluted with a linear salt gradient to 100% Buffer B (25 mM sodium acetate, 1 M NaCl, pH 4.5) in 20 to 25 column volumes. Fractions (5.0 ml) were collected and analyzed by SDS-PAGE and reverse phase RPC18 chromatography. Recombinant Der f 1 proteins produced by recombinant P. pastoris microorganisms eluted at 0.1 to 0.15 M NaCl and migrated as a diffuse band with an apparent molecular weight ranging from about 40 to 46 kD. Fractions containing Der f 1 proteins (>90% homogeneous) were pooled and concentrated using a 10-kD molecular weight cut-off (MWCO) centriprep concentrator.

The Der f 1 protein expressed by recombinant cell P. pastoris HCY215 (P. pastoris strain X33 transformed with plasmid pBC128 containing nucleic acid molecule nDerf1$_{909b}$ (coding strand of SEQ ID NO:28) which encodes the pro-form of Der f 1 (amino acid sequence SEQ ID NO:29)), produced as described in Example 1A, was subjected to N-terminal sequence analysis, using methods known in the art. The N-terminal sequence obtained was analyzed and was found to consist of a mixture of two sequences, with the first being AETSACRINS VNVPSELDLR SLR-, denoted SEQ ID NO:55, and the second being TSACRINSVN VPSELDLRSL R-, denoted SEQ ID NO:56. The sequences obtained surprisingly represent the N-terminus of mature form of the Der f protein, which indicates that P. pastoris is able to express the Der f 1 pro-form and cleave it to produce the mature Der f 1 protein. Since two sequences were obtained, with the first sequence having two extra residues on the N-terminus, it appears that P. pastoris cleaves the pro-protein PDerf1$_{303b}$ (SEQ ID NO:29) at two locations: between the asparagine at position 78 and the alanine at position 79 of SEQ ID NO:29; and between the glutamate at position 80 and threonine at position 81 of SEQ ID NO:29, respectively.

Example 3

This Example describes the production of certain novel mite Group 1 nucleic acid molecules of the present invention. This Example also describes expression of such nucleic acid molecules by recombinant E. coli microorganisms of the present invention.

A. This example describes the production and expression in E. coli of a Der f 1 Group 1 cDNA nucleic acid molecule, denoted herein as nDerf1$_{909c}$, the coding strand of which, represented by SEQ ID NO:34, incorporates E. coli-preferred codon changes as compared to nDerf1$_{909a}$, having a coding strand nucleic acid sequence of SEQ ID NO:4. Nucleic acid molecule nDerf1$_{909c}$ encodes a pro-form of a Der f 1 Group 1 protein, namely PDerf1$_{303c}$. The following codon changes were made to produce nDerf1$_{909c}$ from nDerf1$_{909a}$: a change from CCA to CCG in the codon spanning nucleotide positions 4 to 6 of SEQ ID NO:4; a change from CGA to CGT in the codon spanning nucleotide positions 547 to 549 of SEQ ID NO:4; a change from CGA to CGT in the codon spanning nucleotide positions 553 to 555 of SEQ ID NO:4; and a change from CGA to CGT in the codon spanning nucleotide positions 556 to 558 of SEQ ID NO:4. In addition there is a change from TAT to TAC in the codon spanning nucleotide positions 895 to 897 of SEQ ID NO:4 to eliminate a NdeI cloning site within the Der f 1 coding region. Translation of the resultant coding strand having SEQ ID NO:34 yielded SEQ ID NO:35, also represented as PDerf1$_{303c}$. SEQ ID NO:36 represents the reverse complement of SEQ ID NO:34, i.e., the complementary strand of nDerf1$_{909c}$.

A PCR mutagenesis strategy similar to the one described in Example 1A was used to produce nucleic acid molecule nDerf1$_{909c}$. Four primers (SEQ ID NO:50, 51, 52, and 53) were used in a three step PCR process. In the first PCR step, an about 600-nucleotide PCR product was generated in a manner as described in the first step of the PCR process described in Example 1A, except that the primers were as follows: the sense primer SEQ ID NO:50, 5'GGGAGCTCCA TATGCGTCCG GCTTCAATCA AAAACTT 3' and the antisense primer SEQ ID NO:51, 5'GCGAATTTGG ACGACGGCAACGTTGTTCAC 3'. Primer SEQ ID NO:50 incorporates a 5'NdeI restriction site, shown in bold, and changes codon CCA, a low abundance codon in E. coli, to CCG, the most frequently used codon for that residue; this change is underlined. Primer SEQ ID NO:51 changes three rare ARG codons from CGA, which is rarely used in E. coli, to CGT, the most frequently used. In the second PCR step, an about 370-nucleotide PCR product was generated in a manner as described in the second step of the PCR process described in Example 1A, except that the following primers were used: Primer SEQ ID NO:52, with a sequence of 5'CCCTCGCGGA TCCTCACATG ATTACAAC GTATGGAT 3' incorporates a restriction site for BamH1 (shown in bold) and changes a TYR codon from TAT to TAC (underlined) to eliminate an NdeI cloning site within the Der f 1 coding region; Primer SEQ ID NO:53 is a sense primer with the sequence 5'GTGAACAACG TTGCCGTCGT CCAAATTCGC 3'. The approximately 370-nucleotide PCR fragment generated with SEQ ID NO:53 and SEQ ID NO:52, and the approximately 600-nucleotide fragment produced using primers SEQ ID NO:50 and SEQ ID NO:51, were annealed and the product was reamplified with primers SEQ ID NO:50 and SEQ ID NO:53 to produce an approximately 900-nucleotide fragment which was gel purified, digested with NdeI and BamHI and ligated into similarly cleaved plasmid λPRcro/T2ori/RSET-B, produced as described in PCT Patent Publication No. WO 98/12563, published Mar. 26, 1998, by Grieve et al. The resulting recombinant molecule, denoted pλPR-nDerf1$_{909c}$, includes nDerf1$_{909c}$ operatively linked to lambda transcription control sequences in order to enable expression of the pro-form of Der f 1 (i.e., PDerf1$_{303c}$) with an initiating methionine codon for expression in the E. coli. Recombinant molecule pλPR-nDerf1$_{909c}$, was transformed into E. coli HB101 cells to produce recombinant cell HB101: pλPR-nDerf1$_{909c}$, which when cultured as described in Example 4 leads to production of recombinant Der f 1 protein PDerf$_{303c}$.

B. This example describes the production and expression in E. coli of a Der f 1 Group 1 cDNA nucleic acid molecule, denoted herein as nDerf1$_{669d}$, the coding strand of which, represented by SEQ ID NO:43, incorporates Pichia-preferred codon changes as compared to nDerf1$_{669a}$, having a coding strand nucleic acid sequence of SEQ ID NO:7. Nucleic acid molecule nDerf1$_{669d}$ encodes a mature form of a Der f 1 Group 1 protein, namely PDerf1$_{223d}$, represented by SEQ ID NO:44. SEQ ID NO:45 represents the complementary strand of nucleic acid molecule nDerf1$_{669d}$.

Nucleic acid molecule nDerf1$_{669d}$ and recombinant molecule pλPR-nDerf1$_{669d}$ are produced using a strategy similar to that described in Example 1B such that the nucleotides encoding the "pro" region are deleted from nDerf1$_{909c}$ and pλPR-nDerf1$_{909c}$, produced as described in Example 3A. Recombinant molecule pλPR-nDerf1$_{669d}$ is transformed into *E. coli*, HB101 cells to produce recombinant cell HB101: pλPR-nDerf1$_{669d}$, which when cultured as described in Example 4 leads to production of recombinant Der f 1 protein PDerf1$_{223d}$.

Example 4

This Example describes the production and purification of a mite Group 1 protein of the present invention from *E. coli*.

Recombinant Der f 1 protein PDerf1$_{303c}$ was produced and purified as follows. A colony of recombinant cell HB101: pλPR-nDerf1$_{909c}$, produced as described in Example 3A, was grown in a shake flask at 32° C. in LB broth containing 100 μg/ml ampicillin to a cell density corresponding to an optical density (A600) of about 0.8 to about 1.0. Expression of Der f 1 protein PDerf1$_{303c}$ was induced by shifting the temperature to 42° C. and incubating for an additional 2 to 3 hours. Cells grown in shake flasks were harvested after chilling to 4° C. by centrifugation at 8000×g for 30 minutes in a refrigerated centrifuge (such as Avanti J-20, Beckman Instrument Co., Palo Alto, Calif.) Harvested cells (6 g from 2 L of cell culture) were suspended in 60 ml breaking buffer (25 mM Tris-HCl pH7.5) and passed five times through a microfluidizer (chilled on ice) at 120 psi (pounds per square inch) (such as Microfluidizer Model 1108, Microfluidic Co. Newton, Mass.) to produce a burst cell suspension. PMSF (1.0 mM) was added to the burst cell suspension. The cell suspension was homogenized using a polytron homogenizer (30 seconds at full speed) and then centrifuged at 30,000×g for 30 minutes. The pellet from this centrifugation (P1) was suspended in detergent wash buffer (25 mM Tris-HCl pH7.5, 1% Triton X, 1% deoxycholate, all components available from Sigma) at a volume to weight ratio of 10:1, incubated 30 minutes at room temperature, and re-centrifuged at 30,000×g for 30 minutes. The pellet from this centrifugation (P2) was suspended in breaking buffer at a volume to weight ratio of 10:1 and re-centrifuged at 30,000×g for 30 minutes. The pellet obtained (P3) was shown by SDS-PAGE to contain PDerf1$_{303c}$, while the supernatant fractions from the above-mentioned centrifugations did not contain PDerf1$_{303c}$.

The pellet P3 was solubilized by homogenization in 60 ml WIBS solubilization buffer (8M urea, 25 mM Tris-HCl, pH 9.5, 100 mM β-mercaptoethanol, all available from Sigma), incubated for 30 minutes at room temperature, and centrifuged at 30,000×g for 30 minutes. The supernatant from this centrifugation contained the majority of the PDerf1$_{303c}$ protein.

The supernatant was diluted 1:2 (v/v) with Q-Sepharose load buffer (8M urea, 25 mM Tris-HCl, pH7.5); the pH of the diluted supernatant was adjusted to pH 7.5 and loaded at a flow rate of 5 ml/min onto a 10 mL Q Sepharose column (available from Amersham-Pharmacia Biotech). The column was washed with 5 column volumes of Q Sepharose load buffer. Bound protein was eluted with a linear gradient to 100% Q-Sepharose elution buffer (8M urea, 1.0 M NaCl, 25 mM Tris-HCl pH 7.5, all available from Sigma). Fractions containing recombinant Der f 1 protein PDerf1$_{303c}$ were identified by SDS-PAGE.

Fractions collected from Q Sepharose that contained PDerf1$_{303c}$ were pooled and volume adjusted so that the protein concentration was 1 to 3 mg/ml. The pooled protein fractions were reduced by treatment with 6mM DTT (dithiothreitol, available from Sigma) at room temperature for 30 minutes. Following reduction, oxidized glutathione, 25 to 125 mM, was added to induce the formation of mixed disulfides of the cysteine residues of PDerf1$_{303c}$. Refolding was initiated by rapid dilution to 0.5 to 1.0 M urea using 50 mM Tris, pH 9.5, with the addition of 5 to 25 mM of either reduced glutathione or cysteine. This mixture was incubated at 4° C. for 10 to 20 hours with slow mixing. The mixture was then dialyzed against either PBS, pH 7.5 or 50 mM Tris-HCl pH 7.5, then centrifuged at 30,000×g for 30 minutes. The resulting supernatant contained properly refolded PDerf1$_{303c}$. Purified, refolded PDerf1$_{303c}$ from *E. coli* was subjected to N-terminal amino acid sequencing, using methods known in the art. The N-terminal sequence obtained was MRPASIK-TFE EFKKAFNKNY ATV-, represented herein as SEQ ID NO:59. This sequence is identical to that of the N-terminal sequence of pro-Derf1 (SEQ ID NO:4) with the addition of methionine; thus the *E. coli* expressed and refolded Der f 1 protein appears to be the expected PDerf1$_{303c}$.

Example 5

This Example demonstrates the ability of recombinant *Pichia*-expressed and *E. coli*-expressed Der f 1 proteins of the present invention to bind to IgE from a number of mite allergic sera and compares such binding to that obtained using native purified Der f 1 proteins or mite extracts.

Two samples of native purified Der f 1 protein were used. The first, denoted herein as Heska native Derf1, was purified as described in U.S. patent application Ser. No. 09/292,225, ibid. The second, denoted Chapman native Derf1, was purified in the laboratory of Martin Chapman (University of Virginia Health Sciences Center, Charlottesville, Va.) in the manner described in Lombardero, et al, 1990, *J Immunology* 144, 1353-1360. Recombinant Der f 1 proteins expressed by *P. pastoris* transformed with nucleic acid molecule nDerf1$_{909b}$ or nDerf1$_{669b}$, i.e., PDerf1$_{303b}$ or PDerf1$_{223b}$, respectively, were produced as described in Examples 1 and 2. Note that although the protein produced using nDerf1$_{909b}$ is referred to as PDerf1$_{303b}$, that protein is actually a mature form of Der f 1, as processed by *P. pastoris*; see Example 2. Recombinant Der f 1 protein expressed by *E. coli* transformed with nucleic acid molecule nDerf1$_{909c}$, i.e., PDerf1$_{303c}$, was produced as described in Example 4. Whole *D. farinae* and *D. pteronyssinus* mite extracts were prepared using techniques known to those skilled in the art; see, for example, U.S. patent application Ser. No. 09/292,225, ibid.

Native or recombinant Der f 1 proteins in 100 μl CBC buffer (50 mM sodium carbonate, pH 9.6) were coated onto wells (100 ng per well) of Immulon II microtiter plates (available from Dynex Technologies, Chantilly, Va.) by incubation at 4° C., covered, overnight. Excess fluid was removed and wells were blocked with 200 μl Assay Buffer (4% fetal calf serum (available from Summit Laboratories, Fort Collins, Colo.) in phosphate buffered saline (PBS, recipe in Sambrook, ibid.), plus 0.05% Tween-20 (available from Sigma, St. Louis, Mo.)) for one hour at room temperature. Plates were then washed for 4 cycles on an automatic plate washer (Ultrawash, available from Dynatech Laboratories) using PBS with 0.05% Tween-20. The following serum samples, 100 μl per well, diluted 1:20 in Assay Buffer, were incubated overnight at 4° C.: separate serum samples collected from humans or dogs as indicated in Tables 1, 2 and 3; a pool of mite-allergic human sera; and a pool of mite-allergic dog sera. Control wells were treated identically except that no serum was added. Plates were then washed as described above. Biotinylated human IgE receptor alpha chain (Fc$_e$R1α-biotin) (100 μl of 1.3 ng/ml) prepared as described in U.S. Pat. No. 5,945,294, ibid., was added and incubated for one hour at room temperature. After this incubation, plates were washed as described above. Streptavidin-horseradish peroxidase conjugate (0.5 mg/ml, available from KPL Labs, Gaithersburg, Md.) was added at a 1:5000 dilution in Assay Buffer for one hour at room temperature, after which plates were washed as described above. TMB Peroxidase substrate system, 2 part (available from KPL Labs, #0-76-00), added at 100 µl per well, was used according to the manufacturer's directions. The color reaction was allowed to proceed until good color development was reached (about 10-15 min); then the reaction was stopped with 100 µl per well of 1 M phosphoric acid. Bound IgE was determined by measuring absorbance (Optical Density, or OD) at 450 nm (nanometers) using an ELISA plate reader (such as Spectramax", Molecular Devices, Sunnyvale, Calif.). Background OD readings in the control wells were subtracted from all numbers. Results are reported in Tables 1, 2 and 3 as OD multiplied by 1000. OD numbers greater than 100 are considered to be positive for a reaction with IgE. *P. pastoris*-expressed proteins are denoted in the Tables as *Pichia* expressed proteins.

*pastoris*-expressed PDerf303b protein; i.e., the recombinant *P. pastoris*-expressed Der f 1 protein bound to 100% of the samples that bound to native Der f 1 proteins. Additionally, of the 3 mite-allergic dog serum samples reactive to native Der f 1 proteins, all 3 samples were also reactive (i.e., 100% reactivity) to recombinant *P. pastoris*-expressed PDerf$_{303b}$. The results of this assay indicate that the *P. pastoris*-expressed recombinant PDerf$_{303b}$ has the same relative IgE binding activity compared to the native Der f 1 protein, indicating that the soluble *Pichia* expressed molecule is functionally equivalent to the native molecule with respect to ability to bind IgE specific for mite allergy.

Furthermore, the data in Table 1 indicate that of the 9 mite-allergic human serum samples reactive to native Der f 1 proteins, 7 samples were also reactive (i.e., 78% reactivity) to recombinant *E. coli*-expressed PDerf1$_{303c}$ protein. In addition, the *E. coli*-expressed protein bound to 1 of 2 dog serum samples that bound to native Der f 1 proteins. These results indicate that the pro-form of Der f 1 protein, expressed in *E.*

TABLE 1

Assay Number 1. Binding of IgE from mite-allergic human and dog sera to recombinant *Pichia*-expressed Derf1, to recombinant *E. coli*-expressed Derf1, to native purified Derf1 protein, or to whole *D. farinae* or *D. pteronyssinus* extracts.

| Serum | OD, *E. coli* expressed PDerf1$_{303c}$ | OD, Chapman native Derf1 | OD, Heska native Derf1 | OD, *Pichia*-expressed PDerf1$_{303b}$ | OD, Whole *D. farinae* extract | OD, Whole *D. pteronyssinus* extract |
|---|---|---|---|---|---|---|
| human 1916 | 18 | 17 | 51 | 11 | 25 | 66 |
| human 3848 | 2291 | 2336 | 3123 | 1192 | 3871 | 4200 |
| human 3958 | 147 | 1261 | 3368 | 2244 | 3411 | 4134 |
| human 3960 | 1442 | 1024 | 2279 | 646 | 4048 | 4200 |
| human 3961 | 67 | 326 | 1479 | 433 | 490 | 1130 |
| human 3987 | 1416 | 1216 | 3741 | 1377 | 2836 | 3816 |
| human 4289 | 29 | 287 | 777 | 182 | 1318 | 1746 |
| human 4467 | 236 | 615 | 1302 | 694 | 2527 | 2994 |
| human 5207 | 1902 | 2669 | 3051 | 2153 | 3459 | 3933 |
| human pool | 883 | 1531 | 1732 | 1547 | 3128 | 3499 |
| dog pool | 615 | 341 | 750 | 364 | 3487 | 3643 |
| dog-1 | 0 | 6 | 3 | 21 | 6 | 7 |
| dog-2 | 258 | 1408 | 2245 | 1490 | 2453 | 1876 |
| dog-3 | 45 | 3125 | 2839 | 2499 | 2857 | 928 |

The data in Table 1 indicate that serum samples collected from 8 mite-allergic humans and the pooled human sera sample bound to (i.e., showed reactivity with) native Der f 1 proteins; all 9 samples were also reactive to recombinant *P. pastoris*-expressed PDerf303b protein; i.e., the recombinant *coli* and purified as described in Examples 3 and 4 has a biologically active conformation that can bind to at least about 70% of serum samples that bind to native Der f 1 protein.

TABLE 2

Assay Number 2. Binding of IgE from mite-allergic or normal human and dog sera to recombinant *Pichia*-expressed Derf1, to recombinant *E. coli*-expressed Derf1, to native purified Derf1 protein, or to whole *D. farinae* or *D. pteronyssinus* extracts.

| Serum | OD, *E. coli* expressed PDerf1$_{303c}$ | OD, Chapman native Derf1 | OD, Heska Native Derf1 | OD, *Pichia*-expressed PDerf1$_{303b}$ | OD, Whole *D. farinae* extract | OD, Whole *D. pteronyssinus* extract |
|---|---|---|---|---|---|---|
| human 1916 | 21 | 8 | 62 | 15 | 43 | 62 |
| human 3848 | 2378 | 1726 | 2362 | 904 | 3669 | 4200 |
| human 3958 | 247 | 822 | 2235 | 2369 | 3052 | 4033 |
| human 3960 | 944 | 522 | 1308 | 1046 | 3386 | 3732 |
| human 3961 | 46 | 169 | 784 | 709 | 513 | 1109 |
| human 3987 | 1477 | 846 | 2664 | 2457 | 2358 | 3673 |
| human 4289 | 47 | 173 | 589 | 160 | 1205 | 1665 |
| human 4467 | 277 | 353 | 1051 | 660 | 2210 | 3011 |
| human 5207 | 2122 | 2171 | 2746 | 1304 | 3215 | 3856 |
| human pool | 1161 | 1236 | 2599 | 1551 | 2886 | 3721 |

TABLE 2-continued

Assay Number 2. Binding of IgE from mite-allergic or normal human and dog sera to recombinant *Pichia*-expressed Derf1, to recombinant *E. coli*-expressed Derf1, to native purified Derf1 protein, or to whole *D. farinae* or *D. pteronyssinus* extracts.

| Serum | OD, *E. coli* expressed PDerf1$_{303c}$ | OD, Chapman native Derf1 | OD, Heska Native Derf1 | OD, *Pichia*-expressed PDerf1$_{303b}$ | OD, Whole *D. farinae* extract | OD, Whole *D. pteronyssinus* extract |
|---|---|---|---|---|---|---|
| Heska human B | 0 | 0 | 0 | 2 | 24 | 45 |
| Heska human C | 4 | 0 | 0 | 4 | 5 | 5 |
| Heska human D | 0 | 0 | 0 | 0 | 0 | 0 |
| Heska human E | 10 | 2 | 19 | 1 | 42 | 38 |
| Heska human F | 0 | 0 | 0 | 0 | 0 | 0 |
| Heska human G | 0 | 0 | 1 | 0 | 8 | 2 |
| Heska human H | 0 | 0 | 0 | 0 | 142 | 121 |
| Heska human I | 1 | 0 | 1 | 4 | 4 | 4 |
| Heska human J | 0 | 0 | 1 | 0 | 71 | 74 |
| Heska human K | 0 | 0 | 0 | 0 | 0 | 0 |
| Heska human L | 0 | 0 | 0 | 0 | 35 | 32 |
| Heska human M | 0 | 0 | 51 | 0 | 448 | 573 |
| Heska human N | 24 | 373 | 885 | 370 | 521 | 763 |
| Heska human O | 2 | 0 | 0 | 0 | 16 | 27 |
| Heska human P | 0 | 0 | 0 | 0 | 1 | 7 |
| Heska human Q | 0 | 0 | 0 | 0 | 1 | 7 |
| Heska human R | 0 | 0 | 1 | 0 | 94 | 58 |
| dog sera pool A 146 | 489 | 220 | 449 | 199 | 3120 | 3521 |
| dog sera pool KS338 | 68 | 19 | 101 | 27 | 3665 | 4200 |

The results of Table 2 indicate that of the 10 human serum samples with IgE that bound to native Der f 1 proteins, IgE in all 10 samples also bound to recombinant *P. pastoris*-expressed PDerf1$_{303b}$ protein; i.e., the recombinant *P. pastoris*-expressed Der f 1 protein bound to 100% of the samples that bound to native Der f 1 proteins. Additionally, IgE from serum collected from a mite-allergic dog also bound to the recombinant *P. pastoris*-expressed Der f 1 protein. The results of this assay indicate that the *P. pastoris*-expressed recombinant Der f1 protein expressed from nDerf1$_{909b}$ has equivalent IgE binding activity compared to the native Derf1.

Furthermore, the data in Table 2 indicate that of the 10 mite-allergic human serum samples reactive to native Der f 1 proteins, 7 samples were also reactive (i.e., 70% reactivity) to recombinant *E. coli*-expressed PDerf1$_{303c}$ protein. In addition, the *E. coli*-expressed protein bound to the dog serum sample that bound to native Der f 1 proteins. These results indicate that the pro-form of Der f 1 protein, expressed in *E. coli* and purified as described in Examples 3 and 4 has a biologically active conformation that can bind to at least about 70% of serum samples that bind to native Der f 1 protein.

TABLE 3

Binding of IgE from mite-allergic human and dog sera to recombinant *Pichia*-expressed PDerf1$_{303b}$, PDerf1$_{223b}$, and to purified native mature Der f 1 protein.

| Sera | OD, Derf1, Chapman native | OD, *Pichia*-expressed PDerf1$_{303b}$, preparation number A166-26 | OD, *Pichia*-expressed PDerf1$_{223b}$, preparation 1000-7 |
|---|---|---|---|
| 1916 | 14 | 0 | 0 |
| 3848 | 1033 | 457 | 1253 |
| 3958 | 1067 | 2616 | 1224 |
| 3960 | 738 | 1420 | 634 |
| 3961 | 221 | 744 | 301 |
| 3987 | 865 | 2588 | 1078 |
| 429 | 152 | 104 | 63 |
| 4467 | 489 | 780 | 432 |
| 5207 | 1836 | 1887 | 1096 |
| human pool | 1114 | 1226 | 774 |

The data in Table 3 indicate that Der f 1 proteins expressed by recombinant *P. pastoris* microorganisms transformed with nucleic acid molecules encoding the pro-form or mature form of Der f 1 protein (i.e., with nDerf1$_{909b}$ or nDerf1$_{669b}$, respectively), bind to IgE in serum from human patients with essentially the same reactivity as does native Der f 1 protein. As such, the soluble *P. pastoris*-expressed Der f 1 proteins exhibit closely equivalent IgE binding activity as the native Der f 1 protein, indicating that they are expressed in a biologically active conformation.

Example 6

This Example demonstrates the ability of recombinant *P. pastoris* and *E. coli* Der f 1 proteins of the present invention to bind to anti-Der f 1 protein monoclonal antibodies.

Assays were carried out as follows. A microtiter plate as described in Example 5 was coated overnight at 4° C. with 100 ng/well of anti-Der f 1 protein monoclonal antibody 6A8, denoted herein as anti-Der f 1 MAb 6A8, provided by Dr. Martin Chapman. The plate was washed in the manner described above. The following proteins were then added to wells, having been diluted in Assay Buffer in a 2-fold dilution series, from 0.75 to 50 ng/well: Heska native Derf1, *P. pastoris*-expressed PDerfl$_{303b}$, and *E. coli*-expressed PDerfl$_{303c}$. After incubation for 1 hour at room temperature, plates were washed as described in Example 5. Then 100 μl per well of a 1:1000 dilution in Assay Buffer of biotinylated anti-Der f 1 monoclonal antibody 4C1, also denoted anti-Der f 1 MAb 4C1, provided by Dr. Martin Chapman, was added for 1 hour at room temperature. Plates were washed, streptavidin-HRP conjugate was added, and plates were developed as described in Example 5. Results are provided in Table 4.

TABLE 4

Monoclonal Capture ELISA. OD of native Der f 1 protein, *Pichia*-expressed Der f 1 protein, or *E. coli*-expressed Der f 1 protein captured by anti-Der f 1 MAb 6A8 and detected by anti-Der f 1 MAb 4C1.

| ng protein per well | OD, native Derf1 | OD, *E. coli* expressed PDerfl$_{303c}$ | OD, *Pichia*-expressed PDerfl$_{303b}$ |
|---|---|---|---|
| 50 | 2183 | 1983 | 2148 |
| 25 | 2142 | 1770 | 2156 |
| 2.5 | 2291 | 1372 | 2088 |
| 6.25 | 2197 | 890 | 1961 |
| 3.1 | 2219 | 503 | 1544 |
| 1.5 | 2043 | 268 | 916 |
| 0.75 | 1740 | 136 | 405 |

The results from Table 4 indicate that the binding activities of *P. pastoris*-expressed PDerfl$_{303b}$ and *E. coli* expressed PDerfl$_{303c}$, as measured in a monoclonal antibody capture assay with monoclonal antibodies 6A8 and 4C1, are similar to that of the native Der f 1 protein.

Example 7

This Example demonstrates that a recombinant *P. pastoris*-expressed recombinant Der f 1 protein of the present invention has cysteine protease activity.

Native Der f 1 is believed to be a cysteine protease, based on homology to papain; see, for example, Chua et al, 1992, *J Exp Med* 167, 175-182. The Der f 1 protein secreted as a mature form by recombinant cell *P. pastoris* HCY215 (i.e., *P. pastoris* strain X33 transformed with plasmid pBC128 containing nucleic acid molecule nDerfl$_{909b}$ (coding strand of SEQ ID NO:28) which encodes the pro-form of Der f 1 (amino acid sequence SEQ ID NO:29)) was tested for cysteine protease activity in the following manner. Three concentrations of protein were tested for their abilities to cleave an artificial substrate in the presence or absence of a cysteine protease inhibitor. Specifically, three pairs of samples containing 0.56 μg, 1.1 μg, or 5.6 μg of *P. pastoris*-expressed Der f 1 protein, respectively, were incubated for 30 minutes at room temperature in 20 μl of 50 mM Tris-HCl, pH 8. One member of each pair also contained the irreversible cysteine protease inhibitor E-64 at a concentration of 1 μg/ml. After the pre-incubation, 100 μl of 50 μM quenched fluorogenic substrate z-Val-Leu-Arg-AMC (available from Enzyme Systems Products, Livermore, Calif.) was added to all six samples, and the samples were incubated for 2 hours at room temperature. Fluorescence was measured using a Perkin Elmer Luminescence Spectrometer (model #LS50B) at an excitation wavelength of 380nm and an emission wavelength of 460 nm. The results are shown in Table 5.

TABLE 5

Cysteine protease activity of *P. pastoris*-expressed Der f 1 protein (rDer f 1)

| Micrograms rDer f 1 | Emission (w/o E-64) | Emission (w/E-64) | % Inhibition E-64 |
|---|---|---|---|
| 5.6 | 9.671 | 2.369 | 76 |
| 1.1 | 1.693 | 0.765 | 55 |
| 0.56 | 0.861 | 0.302 | 65 |

These results indicate that the recombinant *P. pastoris*-expressed Der f 1 protein exhibits cysteine protease activity that can be inhibited by pre-incubation with the cysteine protease inhibitor E-64. These results, combined with the IgE binding data of Examples 5 and 6, indicate that recombinant Der f 1 protein expressed by *P. pastoris* is secreted in a biologically active conformation.

Example 8

This Example demonstrates that a Der f 1 protein of the present invention lacking an N-glycosylation site selectively binds to IgE in sera collected from mite allergic human patients in a manner similar to a Der f 1 protein having such a site.

A. The following Der f 1 proteins were reacted as described in Example 5 with a pool of serum samples collected from 16 mite-allergic human patients: (a) Chapman native Der f 1, produced as described in Example 5; (b) recombinant Der f 1 protein PDerfl$_{303b}$, produced by recombinant cell *P. pastoris* HCY215 (*P. pastoris* strain X33 transformed with plasmid pBC128 containing nucleic acid molecule nDerfl$_{909b}$ (coding strand of SEQ ID NO:28) which encodes the pro-form of Der f 1 (amino acid sequence SEQ ID NO:29)), produced as described in Example 1A; and (c) recombinant Der f 1 protein PDerfl$_{303d}$, a Der f 1 protein lacking an N-glycosylation site produced by recombinant cell *P. pastoris* HCY288 (*P. pastoris* strain X33 transformed with plasmid pBC158 containing nucleic acid molecule nDerfl$_{909d}$ (coding strand of SEQ ID NO:37) which encodes the pro-form of Der f 1 in which the asparagine at amino acid position 133 is replaced by glutamine (amino acid sequence SEQ ID NO:38)), produced as described in Example 1A. Table 6 shows the results of this assay, conducted at a variety of Der f 1 protein concentrations.

TABLE 6

Binding of IgE from pooled mite-allergic human sera to recombinant *Pichia*-expressed PDerfl$_{303b}$, PDerfl$_{303d}$, and to purified native mature Der f 1 protein.

| ng protein per well | OD, native Der f 1 | OD, *Pichia*-expressed PDerfl$_{303b}$ | OD, *Pichia*-expressed PDerfl$_{303d}$ |
|---|---|---|---|
| 200 | 584 | 484 | 1448 |
| 100 | 581 | 354 | 1097 |
| 50 | 488 | 293 | 779 |
| 25 | 215 | 240 | 591 |
| 12.5 | 116 | 178 | 347 |
| 6.2 | 17 | 53 | 88 |

These results demonstrate that *P. pastoris*-expressed Der f 1 protein does not require an N-glycosylation site to selectively bind IgE in mite-allergic sera at least as well as native Der f 1 protein or *P. pastoris*-expressed Der f 1 protein with such a site. As such, it appears that N-linked glycosylation is not necessary for Der f 1 protein to react with IgE from mite allergic sera B. The Der f 1 proteins described in Example 8B were reacted as described in Example 6 with a pool of serum samples collected from 16 mite-allergic human patients. Table 7 shows the results of this assay, conducted at a variety of Der f 1 protein concentrations.

TABLE 7

Monoclonal Capture ELISA. Binding of IgE from pooled mite-allergic human sera to recombinant *Pichia*-expressed PDerfl$_{303b}$, PDerfl$_{303d}$, and to purified native mature Derf 1 protein.

| ng protein per well | OD, native Der f 1 | OD, *Pichia*-expressed PDerfl$_{303b}$ | OD, *Pichia*-expressed PDerfl$_{303d}$ |
|---|---|---|---|
| 25   | 2249 | 2389 | 3007 |
| 12.5 | 2483 | 2388 | 3037 |
| 6.25 | 2620 | 2463 | 2991 |
| 3.1  | 2597 | 2103 | 2913 |
| 1.55 | 2447 | 1399 | 2626 |
| 0.78 | 2186 | 871  | 1963 |
| 0.39 | 1480 | 434  | 1380 |

These results further demonstrate that *P. pastoris*-expressed Der f 1 protein does not require an N-glycosylation site to selectively bind IgE in mite-allergic sera at least as well as native Der f 1 protein or *P. pastoris*-expressed Der f 1 protein with such a site. As such, it appears that N-linked glycosylation is not necessary for Der f 1 protein to react with IgE from mite allergic sera.

Example 9

This example describes the production of nucleic acid molecules encoding Der p 1 proteins for expression in *E. coli*.
A. Nucleic Acid Molecules Encoding the Pro Form of Der p1.

A three step PCR, using four oligonucleotides, was used to amplify a DNA fragment containing pro Der p 1 for cloning into expression plasmid pLambda Cro (produced as described in PCT Patent publication No. WO98/12563, hereinafter pLambdaCro). This process is analogous to that described for pro Der f 1 in Example 3, p. 63, to produce nDerfl$_{909c}$.

Two separate PCR amplification reactions were performed: one used forward and reverse primers EB160 with nucleic acid sequence 5'-AGGAGACATATGCGTCCATC-CTCGATCAAAACTTTTG, designated herein as SEQ ID NO:60, and EB163, with nucleic acid sequence 5'-TTGTG-CATTTGGACGACGGCATGATTGTTCTC, designated herein as SEQ ID NO:61, and 2×10$^7$ plaque forming units (PFU) of a *D. pteronyssinus* cDNA library prepared from whole body mites in Lambda Zap (Stratagene, La Jolla, Calif.).

The other amplification reaction used forward and reverse primers EB161, with nucleic acid sequence 5'-TCACCCTG-GATCCCTACAGGATGACAACGTATGGATATTC, designated herein as SEQ ID NO:62, and EB162, with nucleic acid sequence 5'-GAGAACAATCATGCCGTCGTCCAAATG-CACAA, designated herein as SEQ ID NO:63 and 2×10$^7$ PFU *D. pteronyssinus* cDNA library. Conditions for amplifying and purifying the ~0.6 and ~0.4 kb fragments were as described in Example 3. The ~0.6 and ~0.4 kb fragments were annealed together and reamplified in vitro using primers EB160 and EB161, which incorporate NdeI (EB160) and BamH1 (EB161) restriction sites. The resulting ~0.9 kb fragment was purified, digested with Nde1 and BamH1 and subcloned into similarly digested pLambdaCro to produce plasmid pBC194. The pro Der p 1 coding sequence of pBC194 has 909 bases, and is designated herein as SEQ ID NO:64, and the reverse complement is designated as SEQ ID NO:66. The codon optimized arginine residues are encoded by positions 553 through 558 of SEQ ID NO:64. The predicted amino acid sequence is SEQ ID NO:65.
B. Nucleic Acid Molecules Encoding the Mature Der p 1

The mature form of Derp 1 was amplified from pBC194 DNA using Pfu polymerase and the following conditions: 1× manufacturers Pfu buffer, 0.2 mM each dNTP, 0.4 uM each a) forward primer, KB20, with nucleic acid sequence 5'-AAAAAAAAACATATGACTAACGCCTG-CAGTATCAATGGAAATG, designated herein as SEQ ID NO:67, and b) reverse primer KB21, with nucleic acid sequence 5'-AAAAAAAAACTCGAGCTACAGGATGA-CAACGTATGGATATTC, designated herein as SEQ ID NO:68, 26 ng pBC194, and 2.5 U Pfu polymerase, in a 50 ul reaction volume. Amplification conditions were as follows: 1 cycle of 95 C for 2 min, 30 cycles of [95 C for 1 min, 55 C for 1 min, 70 C for 1 min], one cycle of 70 C for 10 min.

The resulting fragment was purified, digested with Nde1 and Xho 1, and subcloned into similarly digested pLambdaCro to produce plasmid pBC204. The mature Der p 1 coding sequence of pBC204 has 669 bases, and is designated herein as SEQ ID NO:69, and the reverse complement is designated as SEQ ID NO:71. The predicted amino acid sequence is SEQ ID NO:70.

Example 10

This example describes the production of nucleic acid molecules encoding Der p1 proteins for expression in *P. pichia*.
A. Nucleic Acid Molecules Encoding Pro Der p 1

Four oligonucleotide primers were used to assemble an ~900 bp fragment containing a version of pro Der p 1. with selected arginine residues optimized for yeast codon bias. Primers EB132 and EB131 change arginine residues specified by either CGA or CGT to AGA, the preferred codon in yeast (*S. cerevisiae*). Forward primer EB130, with nucleic acid sequence 5'-GTGGCTCTCGAGAAGAGAGAG-GCTCGTCCATCTTCCATCAAAACT, designated herein as SEQ ID NO:72, and reverse primer EB131, with nucleic acid sequence 5'-CCGAATCTTTGTGCATTTGGTCTTCT-GCATGATTGTTCTCGTGC, designated herein as SEQ ID NO:73, were used in combination with template DNA from a Lambda Zap cDNA library and appropriate salts, enzymes, etc. (as described in Example 1, p. 56) to produce an ~0.6 kb DNA fragment. Forward primer EB132, with nucleic acid sequence 5'-GCACGAGAACAATCATGCAGAAGAC-CAAATGCACAAAGATTCGG, designated herein as SEQ ID NO:74, and reverse primer EB133, with nucleic acid sequence 5'-GCTCTTGCGGCCGCTTACAAAATGA-CAACGTATGGATA, designated herein as SEQ ID NO:75, were used to amplify an approximately 0.4 kb DNA fragment. The resulting 0.6 and 0.4 kb PCR fragments were annealed and reamplified using primers EB130 and EB133 to produce an ~0.9 kb DNA fragment that was subcloned as a Xho 1-Not 1 fragment into similarly digested pPICZalpha B. The resulting plasmid was designated pBC169.

The Pro Der p 1 coding sequence of pBC169 has 906 bases, and is designated herein as SEQ ID NO:76, and the reverse complement is designated as SEQ ID NO:78. The predicted amino acid sequence is designated SEQ ID NO:77.
B. Nucleic Acid Molecules Encoding Mature Der p 1

An expression plasmid for secreting the mature form of Der p 1 from *Pichia* was constructed using forward primer EB154, with nucleic acid sequence 5'-GGGGTATCTCTC-GAGAAGAGAACTAACGCCTGCAGTATCAATG, designated herein as SEQ ID NO:79, and reverse primer EB155, with nucleic acid sequence 5'-AAGCTGGCGGCCGCTTA-CAAAATGACAACGTATGGATATTC, designated herein as SEQ ID NO:80, and plasmid pBC169 as template DNA. Conditions for amplification and cloning were as described for the analogous plasmid for expressing mature Der f 1 in Pichia (See Example 1B, p. 57-58). The resulting molecule was digested with Xho 1 and Not 1, and inserted into similarly digested pPICZαA to form pBC185. The mature Der p 1 coding sequences of pBC185 has 666 nucleotides and is designated herein as SEQ ID NO:81, and the reverse complement is designated herein as SEQ ID NO:83. The expected protein product of mature Der p 1 has 222 amino acids, and is designated herein as SEQ ID NO:82.

Example 11

This example describes the production of an N-Glycosylation site mutant of pro Der p 1 for expression in Pichia.

Residues 52 to 54 of mature Der p 1 (SEQ ID NO:82) contain a putative N-linked glycosylation site: NQS. A cloning strategy analogous to one the described for pro Der f 1 (N53Q) (Example 1C, p. 58) was used to mutate residue serine 54 (TCA) of the mature Der p 1 (SEQ ID NO:81) to glycine (GGT). Forward and reverse primers for mutagenic PCR were EB 146, with nucleic acid sequence 5'-AAATAAGCTGATTCAGTTGCGGCAACACCAGAG, designated herein as SEQ ID NO:84, and EB147, with nucleic acid sequence (5'-GGCTTACCGTAATCAAG-GTTTGGATCTTGCTG, designated herein as SEQ ID NO:85, respectively. The DNA template for mutagenic PCR was plasmid pBC169. The amplified fragment was digested with Xho1 and Not1 and inserted into similarly digested pPICZαA. The plasmid with the mutated sequence (pro Der p 1S54G) was designated pBC175. The pro Der p1 S54G encoding sequence is 906 nucleotides and has the sequence designated herein as SEQ ID NO:86, and the reverse complement is designated as SEQ ID NO:88. The predicted amino acid sequence is SEQ ID NO:87, and has a glycine at residue 54, rather than the serine present at that position in SEQ ID NO:82.

Example 12

This Example describes the production of a variant of a mite Group 1 protein of the present invention in which the pro-peptide is expected to be unable to self-process.

The in vitro protease activity of rDer f 1, combined with the observation that Pichia strains engineered to produce pro-Der f 1 secrete mature Der f 1, suggests that the pro-peptide undergoes self-processing.

A version of pro Der f 1 with a residue change at C35 of SEQ ID NO:32, the predicted active site cysteine, was produced (pBC182).

Plasmid pBC182 was constructed by mutagensis of plasmid pBC128 (pro Der f 1). Primers for inverse PCR were EB152, with nucleic acid sequence 5'P-GCTGTGGT-TCATCTTGGGCTTTCTCTGGTGTT, designated herein as SEQ ID NO:89, and EB153, with nucleic acid sequence 5'P-CTCCTTGCATACGGATTGGAGTGACAGTTCGC, designated herein as SEQ ID NO:90. Template DNA was pBC128. Conditions for amplification and cloning were as described in Example 1C (page 58). The amplified fragment was digested with Xho 1 and Not 1, and inserted into similarly digested pPICZAlphaB to form pBC 182. The pro Der f1 C35S coding sequence of pBC182 has 909 nucleotides, and is designated herein as SEQ ID NO:91, and the reverse complement is designated as SEQ ID NO:93. The cys to ser change introduced by primer EB152 is at position 35 of the protein sequence, which is designated herein as SEQ ID NO:92.

The resulting rDer f 1 is expected to be secreted from Pichia as the pro-enzyme form if the processing event is self-catalyzed. The analogous variant of Der p 1 is made at position C34 of SEQ ID NO:82. In the above example, the active site cysteine was changed to serine. In another embodiment of the invention, the coding sequences may be mutated to substitute either valine or alanine at that position.

Another possible residue to target is H171 of Der f 1 of SEQ ID NO:32 and H170 of Der p 1 of SEQ ID NO:82. The Cys and His residues are postulated to form an active site thiolate-imidazolium ion pair. Disruption of this pair could impair the proteolytic function of the protein and the mutant is therefore expected to be impaired in self-processing. The histidines may be changed to another amino acid, preferably alanine.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to produce a recombinant protein comprising a recombinant mite Group 1 protein, comprising the steps of:
   (a) culturing a methyltrophic yeast microorganism transformed with a nucleic acid molecule encoding said recombinant mite Group 1 protein; and
   (b) recovering said recombinant mite Group 1 protein from said methyltrophic yeast microorganism;
   wherein
   said recombinant mite Group 1 protein is a *Dermatophagoides pteronyssinus*, recombinant mite Group 1 protein (Der p 1) and
   said nucleic acid molecule consists of the nucleic acid sequence of SEQ ID NO:10, and wherein said nucleic acid molecule is optionally fused to a signal sequence.

2. The method of claim 1, wherein said methyltrophic yeast microorganism is of a genus selected from the group consisting of a *Pichia* microorganism, a *Hansenula* microorganism, a *Torulopsis* microorganism, and a *Candida* microorganism.

3. The method of claim 1, wherein said methyltrophic yeast microorganism is of a species selected from the group consisting of *Pichia pastoris, Pichia acaciae, Pichia anomala, Pichia augusta, Pichia capsulata, Pichia fabianii, Pichia farinosa, Pichia guilliermondii, Pichia methanolica, Pichia norvegensis, Pichia pinus, Pichia stipitis*, and *Hansenula polymorpha*.

4. The method of claim 1, wherein said methyltrophic yeast microorganism is *Pichia pastoris*.

5. The method of claim 1, wherein said nucleic acid molecule encodes a recombinant mite Group 1 protein selected from the group consisting of a pro-form of a recombinant mite Group 1 protein and a mature form of a recombinant mite Group 1 protein.

6. The method of claim 1, wherein said nucleic acid molecule encodes a recombinant mite Group 1 protein fused to a *S. cerevisiae* alpha factor signal sequence.

7. The method of claim 1, wherein said recombinant mite Group 1 protein is
   a recombinant mite Group 1 protein consisting of the amino acid sequence of SEQ ID NO:11.

8. The method of claim 1, wherein said recombinant mite Group 1 protein is selected from the group consisting of a pro-form of said recombinant mite Group 1 protein and a mature form of said recombinant mite Group I protein.

9. The method of claim 1, wherein said recombinant mite Group 1 protein is secreted by said methyltrophic yeast microorganism.

10. A methyltrophic yeast microorganism comprising a nucleic acid molecule encoding a mite Group 1 protein wherein, said nucleic acid molecule consists of the nucleic acid sequence of SEQ ID NO:10, and said recombinant mite Group 1 protein is a *Dermatophagoides pteronyssinus*, recombinant mite Group 1 protein (Der p 1), said nucleic acid molecule being operatively linked to a transcription control sequence and wherein sad nucleic acid molecule is optionally fused to a signal sequence.

11. The methyltrophic yeast microorganism of claim 10, wherein said recombinant mite Group 1 protein is
   a recombinant mite Group 1 protein consisting of the amino acid sequence of SEQ ID NO:11.

12. The methyltrophic yeast microorganism of claim 10, wherein said methyltrophic yeast microorganism is of a genus selected from the group consisting of a *Pichia* microorganism, a *Hansenula* microorganism, a *Torulopsis* microorganism, and, a *Candida* microorganism.

13. The methyltrophic yeast microorganism of claim 12, wherein aid *Pichia* microorganism is *P. pastoris*.

14. The methyltrophic yeast microorganism of claim 13, wherein said nucleic acid molecule encodes a recombinant mite Group 1 protein fused to a *S. cerevisiae* alpha factor signal sequence.

* * * * *

SEQUENCE LISTING

<160> NUMBER OF SEQ ID NOS: 93

<210> SEQ ID NO 1
<211> LENGTH: 963
<212> TYPE: DNA
<213> ORGANISM: Dermatophagoides farinae
<220> FEATURE:
<221> NAME/KEY: CDS
<222> LOCATION: (1)..(963)

<400> SEQUENCE: 1

```
atg aaa ttc gtt ttg gcc att gcc tct ttg ttg gta ttg agc act gtt     48
Met Lys Phe Val Leu Ala Ile Ala Ser Leu Leu Val Leu Ser Thr Val
 1               5                  10                  15 tat gct cgt cca gct tca atc aaa act ttt gaa gaa ttc aaa aaa gcc     96
Tyr Ala Arg Pro Ala Ser Ile Lys Thr Phe Glu Glu Phe Lys Lys Ala
            20                  25                  30
```

-continued

| | | |
|---|---|---|
| ttc aac aaa aac tat gcc acc gtt gaa gag gaa gaa gtt gcc cgt aaa<br>Phe Asn Lys Asn Tyr Ala Thr Val Glu Glu Glu Glu Val Ala Arg Lys<br>35                    40                    45 | 144 |
| aac ttt ttg gaa tca ttg aaa tat gtt gaa gct aac aaa ggt gcc atc<br>Asn Phe Leu Glu Ser Leu Lys Tyr Val Glu Ala Asn Lys Gly Ala Ile<br>50                    55                    60 | 192 |
| aac cat ttg tcc gat ttg tca ttg gat gaa ttc aaa aac cgt tat ttg<br>Asn His Leu Ser Asp Leu Ser Leu Asp Glu Phe Lys Asn Arg Tyr Leu<br>65                    70                    75                    80 | 240 |
| atg agt gct gaa gct ttt gaa caa ctc aaa act caa ttc gat ttg aat<br>Met Ser Ala Glu Ala Phe Glu Gln Leu Lys Thr Gln Phe Asp Leu Asn<br>                    85                    90                    95 | 288 |
| gcc gaa aca agc gct tgc cgt atc aat tcg gtt aac gtt cca tcg gaa<br>Ala Glu Thr Ser Ala Cys Arg Ile Asn Ser Val Asn Val Pro Ser Glu<br>                  100                  105                  110 | 336 |
| ttg gat tta cga tca ctg cga act gtc act cca atc cgt atg caa gga<br>Leu Asp Leu Arg Ser Leu Arg Thr Val Thr Pro Ile Arg Met Gln Gly<br>                  115                  120                  125 | 384 |
| ggc tgt ggt tca tgt tgg gct ttc tct ggt gtt gcc gca act gaa tca<br>Gly Cys Gly Ser Cys Trp Ala Phe Ser Gly Val Ala Ala Thr Glu Ser<br>130                    135                  140 | 432 |
| gct tat ttg gcc tac cgt aac acg tct ttg gat ctt tct gaa cag gaa<br>Ala Tyr Leu Ala Tyr Arg Asn Thr Ser Leu Asp Leu Ser Glu Gln Glu<br>145                    150                  155                  160 | 480 |
| ctc gtc gat tgc gca tct caa cac gga tgt cac ggc gat aca ata cca<br>Leu Val Asp Cys Ala Ser Gln His Gly Cys His Gly Asp Thr Ile Pro<br>                  165                  170                  175 | 528 |
| aga ggc atc gaa tac atc caa caa aat ggt gtc gtt gaa gaa aga agc<br>Arg Gly Ile Glu Tyr Ile Gln Gln Asn Gly Val Val Glu Glu Arg Ser<br>                  180                  185                  190 | 576 |
| tat cca tac gtt gca cga gaa caa cga tgc cga cga cca aat tcg caa<br>Tyr Pro Tyr Val Ala Arg Glu Gln Arg Cys Arg Arg Pro Asn Ser Gln<br>                  195                  200                  205 | 624 |
| cat tac ggt atc tca aac tac tgc caa att tat cca cca gat gtg aaa<br>His Tyr Gly Ile Ser Asn Tyr Cys Gln Ile Tyr Pro Pro Asp Val Lys<br>210                    215                  220 | 672 |
| caa atc cgt gaa gct ttg act caa aca cac aca gct att gcc gtc att<br>Gln Ile Arg Glu Ala Leu Thr Gln Thr His Thr Ala Ile Ala Val Ile<br>225                    230                  235                  240 | 720 |
| att ggc atc aaa gat ttg aga gct ttc caa cat tat gat gga cga aca<br>Ile Gly Ile Lys Asp Leu Arg Ala Phe Gln His Tyr Asp Gly Arg Thr<br>                  245                  250                  255 | 768 |
| atc att caa cat gac aat ggt tat caa cca aac tat cat gcc gtc aac<br>Ile Ile Gln His Asp Asn Gly Tyr Gln Pro Asn Tyr His Ala Val Asn<br>                  260                  265                  270 | 816 |
| att gtc ggt tac gga agt aca caa ggc gac gat tat tgg atc gta cga<br>Ile Val Gly Tyr Gly Ser Thr Gln Gly Asp Asp Tyr Trp Ile Val Arg<br>                  275                  280                  285 | 864 |
| aac agt tgg gat act acc tgg gga gat agc gga tac gga tat ttc caa<br>Asn Ser Trp Asp Thr Thr Trp Gly Asp Ser Gly Tyr Gly Tyr Phe Gln<br>290                    295                  300 | 912 |
| gcc gga aac aac ctc atg atg atc gaa caa tat cca tat gtt gta atc<br>Ala Gly Asn Asn Leu Met Met Ile Glu Gln Tyr Pro Tyr Val Val Ile<br>305                    310                  315                  320 | 960 |
| atg<br>Met | 963 |

<210> SEQ ID NO 2
<211> LENGTH: 321
<212> TYPE: PRT

<213> ORGANISM: Dermatophagoides farinae

<400> SEQUENCE: 2

```
Met Lys Phe Val Leu Ala Ile Ala Ser Leu Leu Val Leu Ser Thr Val
 1               5                  10                  15

Tyr Ala Arg Pro Ala Ser Ile Lys Thr Phe Glu Glu Phe Lys Lys Ala
             20                  25                  30

Phe Asn Lys Asn Tyr Ala Thr Val Glu Glu Glu Val Ala Arg Lys
         35                  40                  45

Asn Phe Leu Glu Ser Leu Lys Tyr Val Glu Ala Asn Lys Gly Ala Ile
     50                  55                  60

Asn His Leu Ser Asp Leu Ser Leu Asp Glu Phe Lys Asn Arg Tyr Leu
 65                  70                  75                  80

Met Ser Ala Glu Ala Phe Glu Gln Leu Lys Thr Gln Phe Asp Leu Asn
                 85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
    130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Arg Cys Arg Arg Pro Asn Ser Gln
        195                 200                 205

His Tyr Gly Ile Ser Asn Tyr Cys Gln Ile Tyr Pro Pro Asp Val Lys
    210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270

Ile Val Gly Tyr Gly Ser Thr Gln Gly Asp Asp Tyr Trp Ile Val Arg
        275                 280                 285

Asn Ser Trp Asp Thr Thr Trp Gly Asp Ser Gly Tyr Gly Tyr Phe Gln
    290                 295                 300

Ala Gly Asn Asn Leu Met Met Ile Glu Gln Tyr Pro Tyr Val Val Ile
305                 310                 315                 320

Met
```

<210> SEQ ID NO 3
<211> LENGTH: 963
<212> TYPE: DNA
<213> ORGANISM: Dermatophagoides farinae

<400> SEQUENCE: 3

```
catgattaca acatatggat attgttcgat catcatgagg ttgtttccgg cttggaaata      60
tccgtatccg ctatctcccc aggtagtatc ccaactgttt cgtacgatcc aataatcgtc     120
gccttgtgta cttccgtaac cgacaatgtt gacggcatga tagtttggtt gataaccatt     180
```

```
gtcatgttga atgattgttc gtccatcata atgttggaaa gctctcaaat ctttgatgcc      240
aataatgacg gcaatagctg tgtgtgtttg agtcaaagct tcacggattt gtttcacatc      300
tggtggataa atttggcagt agtttgagat accgtaatgt tgcgaatttg gtcgtcggca      360
tcgttgttct cgtgcaacgt atggatagct tctttcttca acgacaccat tttgttggat      420
gtattcgatg cctcttggta ttgtatcgcc gtgacatccg tgttgagatg cgcaatcgac      480
gagttcctgt tcagaaagat ccaaagacgt gttacggtag gccaaataag ctgattcagt      540
tgcggcaaca ccagagaaag cccaacatga accacagcct ccttgcatac ggattggagt      600
gacagttcgc agtgatcgta aatccaattc cgatggaacg ttaaccgaat tgatacggca      660
agcgcttgtt tcggcattca aatcgaattg agttttgagt tgttcaaaag cttcagcact      720
catcaaataa cggtttttga attcatccaa tgacaaatcg acaaatggt tgatggcacc      780 tttgttagct tcaacatatt tcaatgattc caaaaagttt ttacgggcaa cttcttcctc      840
ttcaacggtg gcatagtttt tgttgaaggc ttttttgaat tcttcaaaag ttttgattga      900
agctggacga gcataaacag tgctcaatac caacaaagag gcaatggcca aaacgaattt      960
cat                                                                    963
```

```
<210> SEQ ID NO 4
<211> LENGTH: 909
<212> TYPE: DNA
<213> ORGANISM: Dermatophagoides farinae
<220> FEATURE:
<221> NAME/KEY: CDS
<222> LOCATION: (1)..(909)

<400> SEQUENCE: 4 cgt cca gct tca atc aaa act ttt gaa gaa ttc aaa aaa gcc ttc aac       48
Arg Pro Ala Ser Ile Lys Thr Phe Glu Glu Phe Lys Lys Ala Phe Asn
 1               5                  10                  15 aaa aac tat gcc acc gtt gaa gag gaa gaa gtt gcc cgt aaa aac ttt       96
Lys Asn Tyr Ala Thr Val Glu Glu Glu Glu Val Ala Arg Lys Asn Phe
             20                  25                  30 ttg gaa tca ttg aaa tat gtt gaa gct aac aaa ggt gcc atc aac cat      144
Leu Glu Ser Leu Lys Tyr Val Glu Ala Asn Lys Gly Ala Ile Asn His
         35                  40                  45 ttg tcc gat ttg tca ttg gat gaa ttc aaa aac cgt tat ttg atg agt      192
Leu Ser Asp Leu Ser Leu Asp Glu Phe Lys Asn Arg Tyr Leu Met Ser
     50                  55                  60 gct gaa gct ttt gaa caa ctc aaa act caa ttc gat ttg aat gcc gaa      240
Ala Glu Ala Phe Glu Gln Leu Lys Thr Gln Phe Asp Leu Asn Ala Glu
 65                  70                  75                  80 aca agc gct tgc cgt atc aat tcg gtt aac gtt cca tcg gaa ttg gat      288
Thr Ser Ala Cys Arg Ile Asn Ser Val Asn Val Pro Ser Glu Leu Asp
                 85                  90                  95 tta cga tca ctg cga act gtc act cca atc cgt atg caa gga ggc tgt      336
Leu Arg Ser Leu Arg Thr Val Thr Pro Ile Arg Met Gln Gly Gly Cys
            100                 105                 110 ggt tca tgt tgg gct ttc tct ggt gtt gcc gca act gaa tca gct tat      384
Gly Ser Cys Trp Ala Phe Ser Gly Val Ala Ala Thr Glu Ser Ala Tyr
        115                 120                 125 ttg gcc tac cgt aac acg tct ttg gat ctt tct gaa cag gaa ctc gtc      432
Leu Ala Tyr Arg Asn Thr Ser Leu Asp Leu Ser Glu Gln Glu Leu Val
    130                 135                 140 gat tgc gca tct caa cac gga tgt cac ggc gat aca ata cca aga ggc      480
Asp Cys Ala Ser Gln His Gly Cys His Gly Asp Thr Ile Pro Arg Gly
145                 150                 155                 160 atc gaa tac atc caa caa aat ggt gtc gtt gaa gaa aga agc tat cca      528
```

```
Ile Glu Tyr Ile Gln Gln Asn Gly Val Val Glu Glu Arg Ser Tyr Pro
                165                 170                 175 tac gtt gca cga gaa caa cga tgc cga cga cca aat tcg caa cat tac       576
Tyr Val Ala Arg Glu Gln Arg Cys Arg Arg Pro Asn Ser Gln His Tyr
            180                 185                 190 ggt atc tca aac tac tgc caa att tat cca cca gat gtg aaa caa atc       624
Gly Ile Ser Asn Tyr Cys Gln Ile Tyr Pro Pro Asp Val Lys Gln Ile
        195                 200                 205 cgt gaa gct ttg act caa aca cac aca gct att gcc gtc att att ggc       672
Arg Glu Ala Leu Thr Gln Thr His Thr Ala Ile Ala Val Ile Ile Gly
    210                 215                 220 atc aaa gat ttg aga gct ttc caa cat tat gat gga cga aca atc att       720
Ile Lys Asp Leu Arg Ala Phe Gln His Tyr Asp Gly Arg Thr Ile Ile
225                 230                 235                 240 caa cat gac aat ggt tat caa cca aac tat cat gcc gtc aac att gtc       768
Gln His Asp Asn Gly Tyr Gln Pro Asn Tyr His Ala Val Asn Ile Val
                245                 250                 255 ggt tac gga agt aca caa ggc gac gat tat tgg atc gta cga aac agt       816
Gly Tyr Gly Ser Thr Gln Gly Asp Asp Tyr Trp Ile Val Arg Asn Ser
            260                 265                 270 tgg gat act acc tgg gga gat agc gga tac gga tat ttc caa gcc gga       864
Trp Asp Thr Thr Trp Gly Asp Ser Gly Tyr Gly Tyr Phe Gln Ala Gly
        275                 280                 285 aac aac ctc atg atg atc gaa caa tat cca tat gtt gta atc atg           909
Asn Asn Leu Met Met Ile Glu Gln Tyr Pro Tyr Val Val Ile Met
    290                 295                 300

<210> SEQ ID NO 5
<211> LENGTH: 303
<212> TYPE: PRT
<213> ORGANISM: Dermatophagoides farinae

<400> SEQUENCE: 5

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
    50                  55                  60

Ala Glu Ala Phe Glu Gln Leu Lys Thr Gln Phe Asp Leu Asn Ala Glu
65                  70                  75                  80

Thr Ser Ala Cys Arg Ile Asn Ser Val Asn Val Pro Ser Glu Leu Asp
                85                  90                  95

Leu Arg Ser Leu Arg Thr Val Thr Pro Ile Arg Met Gln Gly Gly Cys
            100                 105                 110

Gly Ser Cys Trp Ala Phe Ser Gly Val Ala Ala Thr Glu Ser Ala Tyr
        115                 120                 125

Leu Ala Tyr Arg Asn Thr Ser Leu Asp Leu Ser Glu Gln Glu Leu Val
    130                 135                 140

Asp Cys Ala Ser Gln His Gly Cys His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Arg Cys Arg Arg Pro Asn Ser Gln His Tyr
            180                 185                 190

Gly Ile Ser Asn Tyr Cys Gln Ile Tyr Pro Pro Asp Val Lys Gln Ile
```

```
                     195                 200                 205
Arg Glu Ala Leu Thr Gln Thr His Thr Ala Ile Ala Val Ile Ile Gly
        210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                    245                 250                 255

Gly Tyr Gly Ser Thr Gln Gly Asp Asp Tyr Trp Ile Val Arg Asn Ser
            260                 265                 270

Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
290                 295                 300

<210> SEQ ID NO 6
<211> LENGTH: 909
<212> TYPE: DNA
<213> ORGANISM: Dermatophagoides farinae

<400> SEQUENCE: 6
catgattaca acatatggat attgttcgat catcatgagg ttgtttccgg cttggaaata      60
tccgtatccg ctatctcccc aggtagtatc ccaactgttt cgtacgatcc aataatcgtc     120
gccttgtgta cttccgtaac cgacaatgtt gacggcatga tagtttggtt gataaccatt     180
gtcatgttga atgattgttc gtccatcata atgttggaaa gctctcaaat ctttgatgcc     240
aataatgacg gcaatagctg tgtgtgtttg agtcaaagct tcacggattt gtttcacatc     300
tggtggataa atttggcagt agtttgagat accgtaatgt tgcgaatttg gtcgtcggca     360
tcgttgttct cgtgcaacgt atggatagct tctttcttca acgacaccat tttgttggat     420
gtattcgatg cctcttggta ttgtatcgcc gtgacatccg tgttgagatg cgcaatcgac     480
gagttcctgt tcagaaagat ccaaagacgt gttacgtag gccaaataag ctgattcagt      540
tgcggcaaca ccagagaaag cccaacatga accacagcct ccttgcatac ggattggagt     600
gacagttcgc agtgatcgta aatccaattc cgatggaacg ttaaccgaat tgatacggca     660
agcgcttgtt tcggcattca aatcgaattg agttttgagt tgttcaaaag cttcagcact     720
catcaaataa cggtttttga attcatccaa tgacaaatcg acaaatggt tgatggcacc      780 tttgttagct tcaacatatt tcaatgattc caaaaagttt ttacgggcaa cttcttcctc     840
ttcaacggtg gcatagtttt tgttgaaggc tttttttgaat tcttcaaaag ttttgattga    900
agctggacg                                                             909

<210> SEQ ID NO 7
<211> LENGTH: 669
<212> TYPE: DNA
<213> ORGANISM: Dermatophagoides farinae
<220> FEATURE:
<221> NAME/KEY: CDS
<222> LOCATION: (1)..(669)

<400> SEQUENCE: 7 aca agc gct tgc cgt atc aat tcg gtt aac gtt cca tcg gaa ttg gat        48
Thr Ser Ala Cys Arg Ile Asn Ser Val Asn Val Pro Ser Glu Leu Asp
1               5                   10                  15 tta cga tca ctg cga act gtc act cca atc cgt atg caa gga ggc tgt        96
Leu Arg Ser Leu Arg Thr Val Thr Pro Ile Arg Met Gln Gly Gly Cys
            20                  25                  30 ggt tca tgt tgg gct ttc tct ggt gtt gcc gca act gaa tca gct tat       144
```

```
Gly Ser Cys Trp Ala Phe Ser Gly Val Ala Ala Thr Glu Ser Ala Tyr
             35                  40                  45 ttg gcc tac cgt aac acg tct ttg gat ctt tct gaa cag gaa ctc gtc    192
Leu Ala Tyr Arg Asn Thr Ser Leu Asp Leu Ser Glu Gln Glu Leu Val
     50                  55                  60 gat tgc gca tct caa cac gga tgt cac ggc gat aca ata cca aga ggc    240
Asp Cys Ala Ser Gln His Gly Cys His Gly Asp Thr Ile Pro Arg Gly
 65                  70                  75                  80 atc gaa tac atc caa caa aat ggt gtc gtt gaa gaa aga agc tat cca    288
Ile Glu Tyr Ile Gln Gln Asn Gly Val Val Glu Glu Arg Ser Tyr Pro
                 85                  90                  95 tac gtt gca cga gaa caa cga tgc cga cga cca aat tcg caa cat tac    336
Tyr Val Ala Arg Glu Gln Arg Cys Arg Arg Pro Asn Ser Gln His Tyr
            100                 105                 110 ggt atc tca aac tac tgc caa att tat cca cca gat gtg aaa caa atc    384
Gly Ile Ser Asn Tyr Cys Gln Ile Tyr Pro Pro Asp Val Lys Gln Ile
        115                 120                 125 cgt gaa gct ttg act caa aca cac aca gct att gcc gtc att att ggc    432
Arg Glu Ala Leu Thr Gln Thr His Thr Ala Ile Ala Val Ile Ile Gly
    130                 135                 140 atc aaa gat ttg aga gct ttc caa cat tat gat gga cga aca atc att    480
Ile Lys Asp Leu Arg Ala Phe Gln His Tyr Asp Gly Arg Thr Ile Ile
145                 150                 155                 160 caa cat gac aat ggt tat caa cca aac tat cat gcc gtc aac att gtc    528
Gln His Asp Asn Gly Tyr Gln Pro Asn Tyr His Ala Val Asn Ile Val
                165                 170                 175 ggt tac gga agt aca caa ggc gac gat tat tgg atc gta cga aac agt    576
Gly Tyr Gly Ser Thr Gln Gly Asp Asp Tyr Trp Ile Val Arg Asn Ser
            180                 185                 190 tgg gat act acc tgg gga gat agc gga tac gga tat ttc caa gcc gga    624
Trp Asp Thr Thr Trp Gly Asp Ser Gly Tyr Gly Tyr Phe Gln Ala Gly
        195                 200                 205 aac aac ctc atg atg atc gaa caa tat cca tat gtt gta atc atg        669
Asn Asn Leu Met Met Ile Glu Gln Tyr Pro Tyr Val Val Ile Met
    210                 215                 220

<210> SEQ ID NO 8
<211> LENGTH: 223
<212> TYPE: PRT
<213> ORGANISM: Dermatophagoides farinae

<400> SEQUENCE: 8

Thr Ser Ala Cys Arg Ile Asn Ser Val Asn Val Pro Ser Glu Leu Asp
 1               5                  10                  15

Leu Arg Ser Leu Arg Thr Val Thr Pro Ile Arg Met Gln Gly Gly Cys
                 20                  25                  30

Gly Ser Cys Trp Ala Phe Ser Gly Val Ala Ala Thr Glu Ser Ala Tyr
             35                  40                  45

Leu Ala Tyr Arg Asn Thr Ser Leu Asp Leu Ser Glu Gln Glu Leu Val
     50                  55                  60

Asp Cys Ala Ser Gln His Gly Cys His Gly Asp Thr Ile Pro Arg Gly
 65                  70                  75                  80

Ile Glu Tyr Ile Gln Gln Asn Gly Val Val Glu Glu Arg Ser Tyr Pro
                 85                  90                  95

Tyr Val Ala Arg Glu Gln Arg Cys Arg Arg Pro Asn Ser Gln His Tyr
            100                 105                 110

Gly Ile Ser Asn Tyr Cys Gln Ile Tyr Pro Pro Asp Val Lys Gln Ile
        115                 120                 125

Arg Glu Ala Leu Thr Gln Thr His Thr Ala Ile Ala Val Ile Ile Gly
```

```
                130                 135                 140
Ile Lys Asp Leu Arg Ala Phe Gln His Tyr Asp Gly Arg Thr Ile Ile
145                 150                 155                 160

Gln His Asp Asn Gly Tyr Gln Pro Asn Tyr His Ala Val Asn Ile Val
                165                 170                 175

Gly Tyr Gly Ser Thr Gln Gly Asp Asp Tyr Trp Ile Val Arg Asn Ser
            180                 185                 190

Trp Asp Thr Thr Trp Gly Asp Ser Gly Tyr Gly Tyr Phe Gln Ala Gly
        195                 200                 205

Asn Asn Leu Met Met Ile Glu Gln Tyr Pro Tyr Val Val Ile Met
    210                 215                 220
```

<210> SEQ ID NO 9
<211> LENGTH: 669
<212> TYPE: DNA
<213> ORGANISM: Dermatophagoides farinae

<400> SEQUENCE: 9

```
catgattaca acatatggat attgttcgat catcatgagg ttgtttccgg cttggaaata      60
tccgtatccg ctatctcccc aggtagtatc ccaactgttt cgtacgatcc aataatcgtc     120
gccttgtgta cttccgtaac cgacaatgtt gacggcatga tagtttggtt gataaccatt     180
gtcatgttga atgattgttc gtccatcata atgttggaaa gctctcaaat ctttgatgcc     240
aataatgacg gcaatagctg tgtgtgtttg agtcaaagct tcacggattt gtttcacatc     300
tggtggataa atttggcagt agtttgagat accgtaatgt tgcgaatttg gtcgtcggca     360
tcgttgttct cgtgcaacgt atggatagct tctttcttca acgacaccat tttgttggat     420
gtattcgatg cctcttggta ttgtatcgcc gtgacatccg tgttgagatg cgcaatcgac     480
gagttcctgt tcagaaagat ccaaagacgt gttacggtag ccaaataag ctgattcagt      540
tgcggcaaca ccagagaaag cccaacatga accacagcct ccttgcatac ggattggagt     600
gacagttcgc agtgatcgta aatccaattc cgatggaacg ttaaccgaat tgatacggca     660
agcgcttgt                                                              669
```

<210> SEQ ID NO 10
<211> LENGTH: 960
<212> TYPE: DNA
<213> ORGANISM: Dermatophagoides pteronyssinus
<220> FEATURE:
<221> NAME/KEY: CDS
<222> LOCATION: (1)..(960)

<400> SEQUENCE: 10

```
atg aaa att gtt ttg gcc atc gcc tca ttg ttg gca ttg agc gct gtt         48
Met Lys Ile Val Leu Ala Ile Ala Ser Leu Leu Ala Leu Ser Ala Val
1               5                   10                  15 tat gct cgt cca tca tcg atc aaa act ttt gaa gaa tac aaa aaa gcc         96
Tyr Ala Arg Pro Ser Ser Ile Lys Thr Phe Glu Glu Tyr Lys Lys Ala
                20                  25                  30 ttc aac aaa agt tat gct acc ttc gaa gat gaa gaa gct gcc cgt aaa        144
Phe Asn Lys Ser Tyr Ala Thr Phe Glu Asp Glu Glu Ala Ala Arg Lys
            35                  40                  45 aac ttt ttg gaa tca gta aaa tat gtt caa tca aat gga ggt gcc atc        192
Asn Phe Leu Glu Ser Val Lys Tyr Val Gln Ser Asn Gly Gly Ala Ile
        50                  55                  60 aac cat ttg tcc gat ttg tcg ttg gat gaa ttc aaa aac cga ttt ttg        240
Asn His Leu Ser Asp Leu Ser Leu Asp Glu Phe Lys Asn Arg Phe Leu
65                  70                  75                  80
```

```
atg agt gca gaa gct ttt gaa cac ctc aaa act caa ttc gat ttg aat      288
Met Ser Ala Glu Ala Phe Glu His Leu Lys Thr Gln Phe Asp Leu Asn
            85                  90                  95 gct gaa act aac gcc tgc agt atc aat gga aat gct cca gct gaa atc      336
Ala Glu Thr Asn Ala Cys Ser Ile Asn Gly Asn Ala Pro Ala Glu Ile
        100                 105                 110 gat ttg cga caa atg cga act gtc act ccc att cgt atg caa gga ggc      384
Asp Leu Arg Gln Met Arg Thr Val Thr Pro Ile Arg Met Gln Gly Gly
    115                 120                 125 tgt ggt tca tgt tgg gct ttc tct ggt gtt gcc gca act gaa tca gct      432
Cys Gly Ser Cys Trp Ala Phe Ser Gly Val Ala Ala Thr Glu Ser Ala
130                 135                 140 tat ttg gct tac cgt aat caa tca ttg gat ctt gct gaa caa gaa tta      480
Tyr Leu Ala Tyr Arg Asn Gln Ser Leu Asp Leu Ala Glu Gln Glu Leu
145                 150                 155                 160 gtc gat tgt gct tcc caa cac ggt tgt cat ggt gat acc att cca cgt      528
Val Asp Cys Ala Ser Gln His Gly Cys His Gly Asp Thr Ile Pro Arg
                165                 170                 175 ggt att gaa tac atc caa cat aat ggt gtc gtc caa gaa agc tac tat      576
Gly Ile Glu Tyr Ile Gln His Asn Gly Val Val Gln Glu Ser Tyr Tyr
            180                 185                 190 cga tac gtt gca cga gaa caa tca tgc cga cga cca aat gca caa cgt      624
Arg Tyr Val Ala Arg Glu Gln Ser Cys Arg Arg Pro Asn Ala Gln Arg
        195                 200                 205 ttc ggt atc tca aac tat tgc caa att tac cca cca aat gta aac aaa      672
Phe Gly Ile Ser Asn Tyr Cys Gln Ile Tyr Pro Pro Asn Val Asn Lys
    210                 215                 220 att cgt gaa gct ttg gct caa acc cac agc gct att gcc gtc att att      720
Ile Arg Glu Ala Leu Ala Gln Thr His Ser Ala Ile Ala Val Ile Ile
225                 230                 235                 240 ggc atc aaa gat tta gac gca ttc cgt cat tat gat ggc cga aca atc      768
Gly Ile Lys Asp Leu Asp Ala Phe Arg His Tyr Asp Gly Arg Thr Ile
                245                 250                 255 att caa cgc gat aat ggt tac caa cca aac tat cac gct gtc aac att      816
Ile Gln Arg Asp Asn Gly Tyr Gln Pro Asn Tyr His Ala Val Asn Ile
            260                 265                 270 gtt ggt tac agt aac gca caa ggt gtc gat tat tgg atc gta cga aac      864
Val Gly Tyr Ser Asn Ala Gln Gly Val Asp Tyr Trp Ile Val Arg Asn
        275                 280                 285 agt tgg gat acc aat tgg ggt gat aat ggt tac ggt tat ttt gct gcc      912
Ser Trp Asp Thr Asn Trp Gly Asp Asn Gly Tyr Gly Tyr Phe Ala Ala
    290                 295                 300 aac atc gat ttg atg atg att gaa gaa tat cca tat gtt gtc att ctc      960
Asn Ile Asp Leu Met Met Ile Glu Glu Tyr Pro Tyr Val Val Ile Leu
305                 310                 315                 320

<210> SEQ ID NO 11
<211> LENGTH: 320
<212> TYPE: PRT
<213> ORGANISM: Dermatophagoides pteronyssinus

<400> SEQUENCE: 11

Met Lys Ile Val Leu Ala Ile Ala Ser Leu Leu Ala Leu Ser Ala Val
 1               5                  10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60
```

```
Asn His Leu Ser Asp Leu Ser Leu Asp Glu Phe Lys Asn Arg Phe Leu
 65                  70                  75                  80

Met Ser Ala Glu Ala Phe Glu His Leu Lys Thr Gln Phe Asp Leu Asn
                 85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
        115                 120                 125

Cys Gly Ser Cys Trp Ala Phe Ser Gly Val Ala Ala Thr Glu Ser Ala
130                 135                 140

Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190

Arg Tyr Val Ala Arg Glu Gln Ser Cys Arg Arg Pro Asn Ala Gln Arg
        195                 200                 205

Phe Gly Ile Ser Asn Tyr Cys Gln Ile Tyr Pro Pro Asn Val Asn Lys
210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
            260                 265                 270

Val Gly Tyr Ser Asn Ala Gln Gly Val Asp Tyr Trp Ile Val Arg Asn
        275                 280                 285

Ser Trp Asp Thr Asn Trp Gly Asp Asn Gly Tyr Gly Tyr Phe Ala Ala
290                 295                 300

Asn Ile Asp Leu Met Met Ile Glu Glu Tyr Pro Tyr Val Val Ile Leu
305                 310                 315                 320

<210> SEQ ID NO 12
<211> LENGTH: 960
<212> TYPE: DNA
<213> ORGANISM: Dermatophagoides pteronyssinus

<400> SEQUENCE: 12
gagaatgaca acatatggat attcttcaat catcatcaaa tcgatgttgg cagcaaaata      60
accgtaacca ttatcacccc aattggtatc ccaactgttt cgtacgatcc aataatcgac     120
accttgtgcg ttactgtaac caacaatgtt gacagcgtga tagtttggtt ggtaaccatt     180
atcgcgttga atgattgttc ggccatcata atgacggaat gcgtctaaat ctttgatgcc     240
aataatgacg gcaatagcgc tgtgggtttg agccaaagct tcacgaattt tgtttacatt     300
tggtgggtaa atttggcaat agtttgagat accgaaacgt tgtgcatttg gtcgtcggca     360
tgattgttct cgtgcaacgt atcgatagta gctttcttgg acgacaccat tatgttggat     420
gtattcaata ccacgtggaa tggtatcacc atgacaaccg tgttgggaag cacaatcgac     480
taattcttgt tcagcaagat ccaatgattg ttacggtaa gccaataag ctgattcagt      540 tgcggcaaca ccagagaaag cccaacatga accacagcct ccttgcatac gaatgggagt     600
gacagttcgc atttgtcgca aatcgatttc agctggagca tttccattga tactgcaggc     660
gttagtttca gcattcaaat cgaattgagt tttgaggtgt tcaaaagctt ctgcactcat     720
```

```
caaaaatcgg tttttgaatt catccaacga caaatcggac aaatggttga tggcacctcc      780
atttgattga acatatttta ctgattccaa aaagttttta cgggcagctt cttcatcttc      840
gaaggtagca aacttttgt tgaaggcttt tttgtattct tcaaaagttt tgatcgatga       900
tggacgagca taaacagcgc tcaatgccaa caatgaggcg atggccaaaa caattttcat      960
```

<210> SEQ ID NO 13
<211> LENGTH: 906
<212> TYPE: DNA
<213> ORGANISM: Dermatophagoides pteronyssinus
<220> FEATURE:
<221> NAME/KEY: CDS
<222> LOCATION: (1)..(906)

<400> SEQUENCE: 13

```
cgt cca tca tcg atc aaa act ttt gaa gaa tac aaa aaa gcc ttc aac       48
Arg Pro Ser Ser Ile Lys Thr Phe Glu Glu Tyr Lys Lys Ala Phe Asn
 1               5                  10                  15 aaa agt tat gct acc ttc gaa gat gaa gaa gct gcc cgt aaa aac ttt       96
Lys Ser Tyr Ala Thr Phe Glu Asp Glu Glu Ala Ala Arg Lys Asn Phe
             20                  25                  30 ttg gaa tca gta aaa tat gtt caa tca aat gga ggt gcc atc aac cat      144
Leu Glu Ser Val Lys Tyr Val Gln Ser Asn Gly Gly Ala Ile Asn His
         35                  40                  45 ttg tcc gat ttg tcg ttg gat gaa ttc aaa aac cga ttt ttg atg agt      192
Leu Ser Asp Leu Ser Leu Asp Glu Phe Lys Asn Arg Phe Leu Met Ser
     50                  55                  60 gca gaa gct ttt gaa cac ctc aaa act caa ttc gat ttg aat gct gaa      240
Ala Glu Ala Phe Glu His Leu Lys Thr Gln Phe Asp Leu Asn Ala Glu
 65                  70                  75                  80 act aac gcc tgc agt atc aat gga aat gct cca gct gaa atc gat ttg      288
Thr Asn Ala Cys Ser Ile Asn Gly Asn Ala Pro Ala Glu Ile Asp Leu
                 85                  90                  95 cga caa atg cga act gtc act ccc att cgt atg caa gga ggc tgt ggt      336
Arg Gln Met Arg Thr Val Thr Pro Ile Arg Met Gln Gly Gly Cys Gly
            100                 105                 110 tca tgt tgg gct ttc tct ggt gtt gcc gca act gaa tca gct tat ttg      384
Ser Cys Trp Ala Phe Ser Gly Val Ala Ala Thr Glu Ser Ala Tyr Leu
        115                 120                 125 gct tac cgt aat caa tca ttg gat ctt gct gaa caa gaa tta gtc gat      432
Ala Tyr Arg Asn Gln Ser Leu Asp Leu Ala Glu Gln Glu Leu Val Asp
    130                 135                 140 tgt gct tcc caa cac ggt tgt cat ggt gat acc att cca cgt ggt att      480
Cys Ala Ser Gln His Gly Cys His Gly Asp Thr Ile Pro Arg Gly Ile
145                 150                 155                 160 gaa tac atc caa cat aat ggt gtc gtc caa gaa agc tac tat cga tac      528
Glu Tyr Ile Gln His Asn Gly Val Val Gln Glu Ser Tyr Tyr Arg Tyr
                165                 170                 175 gtt gca cga gaa caa tca tgc cga cga cca aat gca caa cgt ttc ggt      576
Val Ala Arg Glu Gln Ser Cys Arg Arg Pro Asn Ala Gln Arg Phe Gly
            180                 185                 190 atc tca aac tat tgc caa att tac cca cca aat gta aac aaa att cgt      624
Ile Ser Asn Tyr Cys Gln Ile Tyr Pro Pro Asn Val Asn Lys Ile Arg
        195                 200                 205 gaa gct ttg gct caa acc cac agc gct att gcc gtt att att ggc atc      672
Glu Ala Leu Ala Gln Thr His Ser Ala Ile Ala Val Ile Ile Gly Ile
    210                 215                 220 aaa gat tta gac gca ttc cgt cat tat gat ggc cga aca atc att caa      720
Lys Asp Leu Asp Ala Phe Arg His Tyr Asp Gly Arg Thr Ile Ile Gln
225                 230                 235                 240 cgc gat aat ggt tac caa cca aac tat cac gct gtc aac att gtt ggt      768
Arg Asp Asn Gly Tyr Gln Pro Asn Tyr His Ala Val Asn Ile Val Gly
```

```
Arg Asp Asn Gly Tyr Gln Pro Asn Tyr His Ala Val Asn Ile Val Gly
                245                 250                 255 tac agt aac gca caa ggt gtc gat tat tgg atc gta cga aac agt tgg      816
Tyr Ser Asn Ala Gln Gly Val Asp Tyr Trp Ile Val Arg Asn Ser Trp
            260                 265                 270 gat acc aat tgg ggt gat aat ggt tac ggt tat ttt gct gcc aac atc      864
Asp Thr Asn Trp Gly Asp Asn Gly Tyr Gly Tyr Phe Ala Ala Asn Ile
        275                 280                 285 gat ttg atg atg att gaa gaa tat cca tat gtt gtc att ctc              906
Asp Leu Met Met Ile Glu Glu Tyr Pro Tyr Val Val Ile Leu
    290                 295                 300

<210> SEQ ID NO 14
<211> LENGTH: 302
<212> TYPE: PRT
<213> ORGANISM: Dermatophagoides pteronyssinus

<400> SEQUENCE: 14

Arg Pro Ser Ser Ile Lys Thr Phe Glu Glu Tyr Lys Lys Ala Phe Asn
  1               5                  10                  15

Lys Ser Tyr Ala Thr Phe Glu Asp Glu Ala Ala Arg Lys Asn Phe
             20                  25                  30

Leu Glu Ser Val Lys Tyr Val Gln Ser Asn Gly Gly Ala Ile Asn His
         35                  40                  45

Leu Ser Asp Leu Ser Leu Asp Glu Phe Lys Asn Arg Phe Leu Met Ser
 50                  55                  60

Ala Glu Ala Phe Glu His Leu Lys Thr Gln Phe Asp Leu Asn Ala Glu
 65                  70                  75                  80

Thr Asn Ala Cys Ser Ile Asn Gly Asn Ala Pro Ala Glu Ile Asp Leu
                 85                  90                  95

Arg Gln Met Arg Thr Val Thr Pro Ile Arg Met Gln Gly Gly Cys Gly
            100                 105                 110

Ser Cys Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
130                 135                 140

Cys Ala Ser Gln His Gly Cys His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Cys Arg Arg Pro Asn Ala Gln Arg Phe Gly
            180                 185                 190

Ile Ser Asn Tyr Cys Gln Ile Tyr Pro Pro Asn Val Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300
```

-continued

```
<210> SEQ ID NO 15
<211> LENGTH: 906
<212> TYPE: DNA
<213> ORGANISM: Dermatophagoides pteronyssinus

<400> SEQUENCE: 15
gagaatgaca acatatggat attcttcaat catcatcaaa tcgatgttgg cagcaaaata      60
accgtaacca ttatcacccc aattggtatc ccaactgttt cgtacgatcc aataatcgac     120
accttgtgcg ttactgtaac caacaatgtt gacagcgtga tagtttggtt ggtaaccatt     180
atcgcgttga atgattgttc ggccatcata atgacggaat cgtctaaat ctttgatgcc      240 aataatgacg gcaatagcgc tgtgggtttg agccaaagct tcacgaattt tgtttacatt     300
tggtgggtaa atttggcaat agtttgagat accgaaacgt tgtgcatttg gtcgtcggca     360
tgattgttct cgtgcaacgt atcgatagta gctttcttgg acgacaccat tatgttggat     420
gtattcaata ccacgtggaa tggtatcacc atgacaaccg tgttgggaag cacaatcgac     480
taattcttgt tcagcaagat ccaatgattg attacggtaa gccaaataag ctgattcagt     540
tgcggcaaca ccagagaaag cccaacatga accacagcct ccttgcatac gaatgggagt     600
gacagttcgc atttgtcgca aatcgatttc agctggagca tttccattga tactgcaggc     660
gttagtttca gcattcaaat cgaattgagt tttgaggtgt tcaaaagctt ctgcactcat     720
caaaaatcgg ttttgaatt catccaacga caaatcggac aaatggttga tggcacctcc      780
atttgattga acatatttta ctgattccaa aagttttta cgggcagctt cttcatcttc      840
gaaggtagca taacttttgt tgaaggcttt tttgtattct tcaaaagttt tgatcgatga     900
tggacg                                                                906

<210> SEQ ID NO 16
<211> LENGTH: 669
<212> TYPE: DNA
<213> ORGANISM: Dermatophagoides pteronyssinus
<220> FEATURE:
<221> NAME/KEY: CDS
<222> LOCATION: (1)..(669)

<400> SEQUENCE: 16 gaa act aac gcc tgc agt atc aat gga aat gct cca gct gaa atc gat      48
Glu Thr Asn Ala Cys Ser Ile Asn Gly Asn Ala Pro Ala Glu Ile Asp
  1               5                  10                  15 ttg cga caa atg cga act gtc act ccc att cgt atg caa gga ggc tgt       96
Leu Arg Gln Met Arg Thr Val Thr Pro Ile Arg Met Gln Gly Gly Cys
             20                  25                  30 ggt tca tgt tgg gct ttc tct ggt gtt gcc gca act gaa tca gct tat     144
Gly Ser Cys Trp Ala Phe Ser Gly Val Ala Ala Thr Glu Ser Ala Tyr
         35                  40                  45 ttg gct tac cgt aat caa tca ttg gat ctt gct gaa caa gaa tta gtc     192
Leu Ala Tyr Arg Asn Gln Ser Leu Asp Leu Ala Glu Gln Glu Leu Val
     50                  55                  60 gat tgt gct tcc caa cac ggt tgt cat ggt gat acc att cca cgt ggt     240
Asp Cys Ala Ser Gln His Gly Cys His Gly Asp Thr Ile Pro Arg Gly
 65                  70                  75                  80 att gaa tac atc caa cat aat ggt gtc gtc caa gaa agc tac tat cga     288
Ile Glu Tyr Ile Gln His Asn Gly Val Val Gln Glu Ser Tyr Tyr Arg
                 85                  90                  95 tac gtt gca cga gaa caa tca tgc cga cga cca aat gca caa cgt ttc     336
Tyr Val Ala Arg Glu Gln Ser Cys Arg Arg Pro Asn Ala Gln Arg Phe
            100                 105                 110 ggt atc tca aac tat tgc caa att tac cca cca aat gta aac aaa att     384
```

|   |   |   |   |   |   |   |   |   |   |   |   |   |   |   |     |
|---|---|---|---|---|---|---|---|---|---|---|---|---|---|---|-----|
| Gly | Ile | Ser | Asn | Tyr | Cys | Gln | Ile | Tyr | Pro | Pro | Asn | Val | Asn | Lys | Ile |
|     |     |     | 115 |     |     |     | 120 |     |     |     | 125 |     |     |     |     |

```
cgt gaa gct ttg gct caa acc cac agc gct att gcc gtc att att ggc       432
Arg Glu Ala Leu Ala Gln Thr His Ser Ala Ile Ala Val Ile Ile Gly
    130                 135                 140 atc aaa gat tta gac gca ttc cgt cat tat gat ggc cga aca atc att       480
Ile Lys Asp Leu Asp Ala Phe Arg His Tyr Asp Gly Arg Thr Ile Ile
145                 150                 155                 160 caa cgc gat aat ggt tac caa cca aac tat cac gct gtc aac att gtt       528
Gln Arg Asp Asn Gly Tyr Gln Pro Asn Tyr His Ala Val Asn Ile Val
                165                 170                 175 ggt tac agt aac gca caa ggt gtc gat tat tgg atc gta cga aac agt       576
Gly Tyr Ser Asn Ala Gln Gly Val Asp Tyr Trp Ile Val Arg Asn Ser
            180                 185                 190 tgg gat acc aat tgg ggt gat aat ggt tac ggt tat ttt gct gcc aac       624
Trp Asp Thr Asn Trp Gly Asp Asn Gly Tyr Gly Tyr Phe Ala Ala Asn
        195                 200                 205 atc gat ttg atg atg att gaa gaa tat cca tat gtt gtc att ctc           669
Ile Asp Leu Met Met Ile Glu Glu Tyr Pro Tyr Val Val Ile Leu
    210                 215                 220
```

<210> SEQ ID NO 17
<211> LENGTH: 223
<212> TYPE: PRT
<213> ORGANISM: Dermatophagoides pteronyssinus

<400> SEQUENCE: 17

Glu Thr Asn Ala Cys Ser Ile Asn Gly Asn Ala Pro Ala Glu Ile Asp
 1               5                  10                  15

Leu Arg Gln Met Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
        35                  40                  45

Leu Ala Tyr Arg Asn Gln Ser Leu Asp Leu Ala Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln His Asn Gly Val Val Gln Glu Ser Tyr Tyr Arg
                85                  90                  95

Tyr Val Ala Arg Glu Gln Ser Cys Arg Arg Pro Asn Ala Gln Arg Phe
            100                 105                 110

Gly Ile Ser Asn Tyr Cys Gln Ile Tyr Pro Pro Asn Val Asn Lys Ile
        115                 120                 125

Arg Glu Ala Leu Ala Gln Thr His Ser Ala Ile Ala Val Ile Ile Gly
    130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
                165                 170                 175

Gly Tyr Ser Asn Ala Gln Gly Val Asp Tyr Trp Ile Val Arg Asn Ser
            180                 185                 190

Trp Asp Thr Asn Trp Gly Asp Asn Gly Tyr Gly Tyr Phe Ala Ala Asn
        195                 200                 205

Ile Asp Leu Met Met Ile Glu Glu Tyr Pro Tyr Val Val Ile Leu
    210                 215                 220

<210> SEQ ID NO 18
<211> LENGTH: 669

-continued

<210> SEQ ID NO 18
<211> LENGTH: 669
<212> TYPE: DNA
<213> ORGANISM: Dermatophagoides pteronyssinus

<400> SEQUENCE: 18

```
gagaatgaca acatatggat attcttcaat catcatcaaa tcgatgttgg cagcaaaata      60
accgtaacca ttatcacccc aattggtatc ccaactgttt cgtacgatcc aataatcgac     120
accttgtgcg ttactgtaac caacaatgtt gacagcgtga tagtttggtt ggtaaccatt     180
atcgcgttga atgattgttc ggccatcata atgacggaat gcgtctaaat ctttgatgcc     240
aataatgacg gcaatagcgc tgtgggtttg agccaaagct tcacgaattt tgtttacatt     300
tggtgggtaa atttggcaat agtttgagat accgaaacgt tgtgcatttg gtcgtcggca     360
tgattgttct cgtgcaacgt atcgatagta gctttcttgg acgacaccat tatgttggat     420
gtattcaata ccacgtggaa tggtatcacc atgcaaccg tgttgggaag cacaatcgac      480
taattcttgt tcagcaagat ccaatgattg attacggtaa gccaaataag ctgattcagt     540
tgcggcaaca ccagagaaag cccaacatga accacagcct ccttgcatac gaatgggagt     600
gacagttcgc atttgtcgca aatcgatttc agctggagca tttccattga tactgcaggc     660
gttagtttc                                                             669
```

<210> SEQ ID NO 19
<211> LENGTH: 963
<212> TYPE: DNA
<213> ORGANISM: Euroglyphus maynei
<220> FEATURE:
<221> NAME/KEY: CDS
<222> LOCATION: (1)..(963)

<400> SEQUENCE: 19

```
atg aaa atc att ttg gcc atc gcc tca ttg ttg gta ttg agc gct gtt       48
Met Lys Ile Ile Leu Ala Ile Ala Ser Leu Leu Val Leu Ser Ala Val
  1               5                  10                  15 tat gct cgt cca gct tcg atc aaa act ttt gaa gaa ttc aaa aaa gcc       96
Tyr Ala Arg Pro Ala Ser Ile Lys Thr Phe Glu Glu Phe Lys Lys Ala
             20                  25                  30 ttc aac aaa acc tat gct acc cct gaa aag gaa gaa gtt gcc cgt aaa      144
Phe Asn Lys Thr Tyr Ala Thr Pro Glu Lys Glu Glu Val Ala Arg Lys
         35                  40                  45 aac ttt ttg gaa tca ttg aaa tat gtg gaa tca aac aaa ggt gcc atc      192
Asn Phe Leu Glu Ser Leu Lys Tyr Val Glu Ser Asn Lys Gly Ala Ile
     50                  55                  60 aac cat ttg tcc gat ttg tca ttg gat gaa ttc aaa aac caa ttt ttg      240
Asn His Leu Ser Asp Leu Ser Leu Asp Glu Phe Lys Asn Gln Phe Leu
 65                  70                  75                  80 atg aat gct aat gct ttt gaa caa ctc aaa act caa ttc gat ttg aat      288
Met Asn Ala Asn Ala Phe Glu Gln Leu Lys Thr Gln Phe Asp Leu Asn
                 85                  90                  95 gct gaa act tat gct tgc agt att aac tca gtg agt tta cca tcg gaa      336
Ala Glu Thr Tyr Ala Cys Ser Ile Asn Ser Val Ser Leu Pro Ser Glu
            100                 105                 110 ctt gat tta cgt tca ctg cga act gta act cca atc cgt atg caa gga      384
Leu Asp Leu Arg Ser Leu Arg Thr Val Thr Pro Ile Arg Met Gln Gly
        115                 120                 125 ggc tgt ggt tca tgc tgg gct ttc tct ggt gtt gcc tca act gag tca      432
Gly Cys Gly Ser Cys Trp Ala Phe Ser Gly Val Ala Ser Thr Glu Ser
    130                 135                 140 gct tat ttg gcc tac cgc aac atg tct ttg gat ctt gct gaa caa gaa      480
Ala Tyr Leu Ala Tyr Arg Asn Met Ser Leu Asp Leu Ala Glu Gln Glu
145                 150                 155                 160
```

```
tta gtc gat tgt gct tca caa aac ggt tgc cat ggt gat aca att cca      528
Leu Val Asp Cys Ala Ser Gln Asn Gly Cys His Gly Asp Thr Ile Pro
            165                 170                 175 cgc gga att gaa tac atc caa caa aat ggt gtc gtc caa gaa cac tac      576
Arg Gly Ile Glu Tyr Ile Gln Gln Asn Gly Val Val Gln Glu His Tyr
        180                 185                 190 tat cca tac gtt gca cga gaa caa tca tgc cat cga cca aat gca caa      624
Tyr Pro Tyr Val Ala Arg Glu Gln Ser Cys His Arg Pro Asn Ala Gln
    195                 200                 205 cgt tac ggt ctc aag aac tat tgc caa att tcg cca cca gac tcg aac      672
Arg Tyr Gly Leu Lys Asn Tyr Cys Gln Ile Ser Pro Pro Asp Ser Asn
210                 215                 220 aaa atc cgt caa gct ttg act caa aca cat aca gcc gtt gcc gtc att      720
Lys Ile Arg Gln Ala Leu Thr Gln Thr His Thr Ala Val Ala Val Ile
225                 230                 235                 240 att ggc atc aaa gat ttg aac gct ttc cga cat tat gat gga cga aca      768
Ile Gly Ile Lys Asp Leu Asn Ala Phe Arg His Tyr Asp Gly Arg Thr
            245                 250                 255 atc atg caa cac gac aat ggt tat caa cca aac tat cat gcc gtc aac      816
Ile Met Gln His Asp Asn Gly Tyr Gln Pro Asn Tyr His Ala Val Asn
        260                 265                 270 att gtt ggt tac ggt aat aca caa ggt gtt gat tat tgg atc gta cga      864
Ile Val Gly Tyr Gly Asn Thr Gln Gly Val Asp Tyr Trp Ile Val Arg
    275                 280                 285 aac agt tgg gat acc act tgg ggt gat aat ggc tat ggt tat ttc gct      912
Asn Ser Trp Asp Thr Thr Trp Gly Asp Asn Gly Tyr Gly Tyr Phe Ala
290                 295                 300 gcc aac atc aat ttg atg atg atc gaa caa tat cca tat gta gtc atg      960
Ala Asn Ile Asn Leu Met Met Ile Glu Gln Tyr Pro Tyr Val Val Met
305                 310                 315                 320 ctt                                                                   963
Leu

<210> SEQ ID NO 20
<211> LENGTH: 321
<212> TYPE: PRT
<213> ORGANISM: Euroglyphus maynei

<400> SEQUENCE: 20

Met Lys Ile Ile Leu Ala Ile Ala Ser Leu Leu Val Leu Ser Ala Val
1               5                   10                  15

Tyr Ala Arg Pro Ala Ser Ile Lys Thr Phe Glu Glu Phe Lys Lys Ala
            20                  25                  30

Phe Asn Lys Thr Tyr Ala Thr Pro Glu Lys Glu Val Ala Arg Lys
        35                  40                  45

Asn Phe Leu Glu Ser Leu Lys Tyr Val Glu Ser Asn Lys Gly Ala Ile
    50                  55                  60

Asn His Leu Ser Asp Leu Ser Leu Asp Glu Phe Lys Asn Gln Phe Leu
65                  70                  75                  80

Met Asn Ala Asn Ala Phe Glu Gln Leu Lys Thr Gln Phe Asp Leu Asn
                85                  90                  95

Ala Glu Thr Tyr Ala Cys Ser Ile Asn Ser Val Ser Leu Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ser Thr Glu Ser
    130                 135                 140

Ala Tyr Leu Ala Tyr Arg Asn Met Ser Leu Asp Leu Ala Glu Gln Glu
145                 150                 155                 160
```

```
Leu Val Asp Cys Ala Ser Gln Asn Gly Cys His Gly Asp Thr Ile Pro
                165                 170                 175

Arg Gly Ile Glu Tyr Ile Gln Gln Asn Gly Val Val Gln Glu His Tyr
            180                 185                 190

Tyr Pro Tyr Val Ala Arg Glu Gln Ser Cys His Arg Pro Asn Ala Gln
        195                 200                 205

Arg Tyr Gly Leu Lys Asn Tyr Cys Gln Ile Ser Pro Pro Asp Ser Asn
    210                 215                 220

Lys Ile Arg Gln Ala Leu Thr Gln Thr His Thr Ala Val Ala Val Ile
225                 230                 235                 240

Ile Gly Ile Lys Asp Leu Asn Ala Phe Arg His Tyr Asp Gly Arg Thr
                245                 250                 255

Ile Met Gln His Asp Asn Gly Tyr Gln Pro Asn Tyr His Ala Val Asn
            260                 265                 270

Ile Val Gly Tyr Gly Asn Thr Gln Gly Val Asp Tyr Trp Ile Val Arg
        275                 280                 285

Asn Ser Trp Asp Thr Thr Trp Gly Asp Asn Gly Tyr Gly Tyr Phe Ala
    290                 295                 300

Ala Asn Ile Asn Leu Met Met Ile Glu Gln Tyr Pro Tyr Val Val Met
305                 310                 315                 320

Leu

<210> SEQ ID NO 21
<211> LENGTH: 963
<212> TYPE: DNA
<213> ORGANISM: Euroglyphus maynei

<400> SEQUENCE: 21
aagcatgact acatatggat attgttcgat catcatcaaa ttgatgttgg cagcgaaata    60
accatagcca ttatcacccc aagtggtatc ccaactgttt cgtacgatcc aataatcaac   120
accttgtgta ttaccgtaac caacaatgtt gacggcatga tagtttggtt gataaccatt   180
gtcgtgttgc atgattgttc gtccatcata atgtcggaaa gcgttcaaat ctttgatgcc   240
aataatgacg gcaacggctg tatgtgtttg agtcaaagct tgacggattt tgttcgagtc   300
tggtggcgaa atttggcaat agttcttgag accgtaacgt tgtgcatttg gtcgatggca   360
tgattgttct cgtgcaacgt atggatagta gtgttcttgg acgacaccat tttgttggat   420
gtattcaatt ccgcgtggaa ttgtatcacc atggcaaccg ttttgtgaag cacaatcgac   480
taattcttgt tcagcaagat ccaaagacat gttgcggtag gccaaataag ctgactcagt   540
tgaggcaaca ccagagaaag cccagcatga accacagcct ccttgcatac ggattggagt   600
tacagttcgc agtgaacgta aatcaagttc cgatggtaaa ctcactgagt taatactgca   660
agcataagtt tcagcattca aatcgaattg agttttgagt tgttcaaaag cattagcatt   720
catcaaaaat tggttttttga attcatccaa tgacaaatcg acaaatggt tgatggcacc    780
tttgtttgat tccacatatt tcaatgattc caaaaagttt ttacgggcaa cttcttcctt   840
ttcaggggta gcataggttt tgttgaaggc ttttttgaat tcttcaaaag ttttgatcga   900
agctggacga gcataaacag cgctcaatac caacaatgag gcgatggcca aaatgatttt   960
cat                                                                 963

<210> SEQ ID NO 22
<211> LENGTH: 909
<212> TYPE: DNA
<213> ORGANISM: Euroglyphus maynei
```

<220> FEATURE:
<221> NAME/KEY: CDS
<222> LOCATION: (1)..(909)

<400> SEQUENCE: 22

| | | | | | | | | | | | | | | | | |
|---|---|---|---|---|---|---|---|---|---|---|---|---|---|---|---|---|
| cgt | cca | gct | tcg | atc | aaa | act | ttt | gaa | gaa | ttc | aaa | aaa | gcc | ttc | aac | 48 |
| Arg | Pro | Ala | Ser | Ile | Lys | Thr | Phe | Glu | Glu | Phe | Lys | Lys | Ala | Phe | Asn | |
| 1 | | | | 5 | | | | | 10 | | | | | 15 | | |
| aaa | acc | tat | gct | acc | cct | gaa | aag | gaa | gaa | gtt | gcc | cgt | aaa | aac | ttt | 96 |
| Lys | Thr | Tyr | Ala | Thr | Pro | Glu | Lys | Glu | Glu | Val | Ala | Arg | Lys | Asn | Phe | |
| | | | 20 | | | | | 25 | | | | | 30 | | | |
| ttg | gaa | tca | ttg | aaa | tat | gtg | gaa | tca | aac | aaa | ggt | gcc | atc | aac | cat | 144 |
| Leu | Glu | Ser | Leu | Lys | Tyr | Val | Glu | Ser | Asn | Lys | Gly | Ala | Ile | Asn | His | |
| | 35 | | | | | 40 | | | | | 45 | | | | | |
| ttg | tcc | gat | ttg | tca | ttg | gat | gaa | ttc | aaa | aac | caa | ttt | ttg | atg | aat | 192 |
| Leu | Ser | Asp | Leu | Ser | Leu | Asp | Glu | Phe | Lys | Asn | Gln | Phe | Leu | Met | Asn | |
| 50 | | | | | 55 | | | | | 60 | | | | | | |
| gct | aat | gct | ttt | gaa | caa | ctc | aaa | act | caa | ttc | gat | ttg | aat | gct | gaa | 240 |
| Ala | Asn | Ala | Phe | Glu | Gln | Leu | Lys | Thr | Gln | Phe | Asp | Leu | Asn | Ala | Glu | |
| 65 | | | | 70 | | | | | 75 | | | | | 80 | | |
| act | tat | gct | tgc | agt | att | aac | tca | gtg | agt | tta | cca | tcg | gaa | ctt | gat | 288 |
| Thr | Tyr | Ala | Cys | Ser | Ile | Asn | Ser | Val | Ser | Leu | Pro | Ser | Glu | Leu | Asp | |
| | | | 85 | | | | | 90 | | | | | 95 | | | |
| tta | cgt | tca | ctg | cga | act | gta | act | cca | atc | cgt | atg | caa | gga | ggc | tgt | 336 |
| Leu | Arg | Ser | Leu | Arg | Thr | Val | Thr | Pro | Ile | Arg | Met | Gln | Gly | Gly | Cys | |
| | | 100 | | | | | 105 | | | | | 110 | | | | |
| ggt | tca | tgc | tgg | gct | ttc | tct | ggt | gtt | gcc | tca | act | gag | tca | gct | tat | 384 |
| Gly | Ser | Cys | Trp | Ala | Phe | Ser | Gly | Val | Ala | Ser | Thr | Glu | Ser | Ala | Tyr | |
| | 115 | | | | | 120 | | | | | 125 | | | | | |
| ttg | gcc | tac | cgc | aac | atg | tct | ttg | gat | ctt | gct | gaa | caa | gaa | tta | gtc | 432 |
| Leu | Ala | Tyr | Arg | Asn | Met | Ser | Leu | Asp | Leu | Ala | Glu | Gln | Glu | Leu | Val | |
| 130 | | | | | 135 | | | | | 140 | | | | | | |
| gat | tgt | gct | tca | caa | aac | ggt | gcc | cat | ggt | gat | aca | att | cca | cgc | gga | 480 |
| Asp | Cys | Ala | Ser | Gln | Asn | Gly | Cys | His | Gly | Asp | Thr | Ile | Pro | Arg | Gly | |
| 145 | | | | 150 | | | | | 155 | | | | | 160 | | |
| att | gaa | tac | atc | caa | caa | aat | ggt | gtc | gtc | caa | gaa | cac | tac | tat | cca | 528 |
| Ile | Glu | Tyr | Ile | Gln | Gln | Asn | Gly | Val | Val | Gln | Glu | His | Tyr | Tyr | Pro | |
| | | | 165 | | | | | 170 | | | | | 175 | | | |
| tac | gtt | gca | cga | gaa | caa | tca | tgc | cat | cga | cca | aat | gca | caa | cgt | tac | 576 |
| Tyr | Val | Ala | Arg | Glu | Gln | Ser | Cys | His | Arg | Pro | Asn | Ala | Gln | Arg | Tyr | |
| | | 180 | | | | | 185 | | | | | 190 | | | | |
| ggt | ctc | aag | aac | tat | tgc | caa | att | tcg | cca | cca | gac | tcg | aac | aaa | atc | 624 |
| Gly | Leu | Lys | Asn | Tyr | Cys | Gln | Ile | Ser | Pro | Pro | Asp | Ser | Asn | Lys | Ile | |
| | 195 | | | | | 200 | | | | | 205 | | | | | |
| cgt | caa | gct | ttg | act | caa | aca | cat | aca | gcc | gtt | gcc | gtc | att | att | ggc | 672 |
| Arg | Gln | Ala | Leu | Thr | Gln | Thr | His | Thr | Ala | Val | Ala | Val | Ile | Ile | Gly | |
| 210 | | | | | 215 | | | | | 220 | | | | | | |
| atc | aaa | gat | ttg | aac | gct | ttc | cga | cat | tat | gat | gga | cga | aca | atc | atg | 720 |
| Ile | Lys | Asp | Leu | Asn | Ala | Phe | Arg | His | Tyr | Asp | Gly | Arg | Thr | Ile | Met | |
| 225 | | | | 230 | | | | | 235 | | | | | 240 | | |
| caa | cac | gac | aat | ggt | tat | caa | cca | aac | tat | cat | gcc | gtc | aac | att | gtt | 768 |
| Gln | His | Asp | Asn | Gly | Tyr | Gln | Pro | Asn | Tyr | His | Ala | Val | Asn | Ile | Val | |
| | | | 245 | | | | | 250 | | | | | 255 | | | |
| ggt | tac | ggt | aat | aca | caa | ggt | gtt | gat | tat | tgg | atc | gta | cga | aac | agt | 816 |
| Gly | Tyr | Gly | Asn | Thr | Gln | Gly | Val | Asp | Tyr | Trp | Ile | Val | Arg | Asn | Ser | |
| | | 260 | | | | | 265 | | | | | 270 | | | | |
| tgg | gat | acc | act | tgg | ggt | gat | aat | ggc | tat | ggt | tat | ttc | gct | gcc | aac | 864 |
| Trp | Asp | Thr | Thr | Trp | Gly | Asp | Asn | Gly | Tyr | Gly | Tyr | Phe | Ala | Ala | Asn | |
| | 275 | | | | | 280 | | | | | 285 | | | | | |
| atc | aat | ttg | atg | atg | atc | gaa | caa | tat | cca | tat | gta | gtc | atg | ctt | | 909 |
| Ile | Asn | Leu | Met | Met | Ile | Glu | Gln | Tyr | Pro | Tyr | Val | Val | Met | Leu | | |

<210> SEQ ID NO 23
<211> LENGTH: 303
<212> TYPE: PRT
<213> ORGANISM: Euroglyphus maynei

<400> SEQUENCE: 23

```
Arg Pro Ala Ser Ile Lys Thr Phe Glu Glu Phe Lys Lys Ala Phe Asn
  1               5                  10                  15
Lys Thr Tyr Ala Thr Pro Glu Lys Glu Glu Val Ala Arg Lys Asn Phe
             20                  25                  30
Leu Glu Ser Leu Lys Tyr Val Glu Ser Asn Lys Gly Ala Ile Asn His
         35                  40                  45
Leu Ser Asp Leu Ser Leu Asp Glu Phe Lys Asn Gln Phe Leu Met Asn
     50                  55                  60
Ala Asn Ala Phe Glu Gln Leu Lys Thr Gln Phe Asp Leu Asn Ala Glu
 65                  70                  75                  80
Thr Tyr Ala Cys Ser Ile Asn Ser Val Ser Leu Pro Ser Glu Leu Asp
                 85                  90                  95
Leu Arg Ser Leu Arg Thr Val Thr Pro Ile Arg Met Gln Gly Gly Cys
            100                 105                 110
Gly Ser Cys Trp Ala Phe Ser Gly Val Ala Ser Thr Glu Ser Ala Tyr
        115                 120                 125
Leu Ala Tyr Arg Asn Met Ser Leu Asp Leu Ala Glu Gln Glu Leu Val
    130                 135                 140
Asp Cys Ala Ser Gln Asn Gly Cys His Gly Asp Thr Ile Pro Arg Gly
145                 150                 155                 160
Ile Glu Tyr Ile Gln Gln Asn Gly Val Val Gln Glu His Tyr Tyr Pro
                165                 170                 175
Tyr Val Ala Arg Glu Gln Ser Cys His Arg Pro Asn Ala Gln Arg Tyr
            180                 185                 190
Gly Leu Lys Asn Tyr Cys Gln Ile Ser Pro Pro Asp Ser Asn Lys Ile
        195                 200                 205
Arg Gln Ala Leu Thr Gln Thr His Thr Ala Val Ala Val Ile Ile Gly
    210                 215                 220
Ile Lys Asp Leu Asn Ala Phe Arg His Tyr Asp Gly Arg Thr Ile Met
225                 230                 235                 240
Gln His Asp Asn Gly Tyr Gln Pro Asn Tyr His Ala Val Asn Ile Val
                245                 250                 255
Gly Tyr Gly Asn Thr Gln Gly Val Asp Tyr Trp Ile Val Arg Asn Ser
            260                 265                 270
Trp Asp Thr Thr Trp Gly Asp Asn Gly Tyr Gly Tyr Phe Ala Ala Asn
        275                 280                 285
Ile Asn Leu Met Met Ile Glu Gln Tyr Pro Tyr Val Val Met Leu
    290                 295                 300
```

<210> SEQ ID NO 24
<211> LENGTH: 909
<212> TYPE: DNA
<213> ORGANISM: Euroglyphus maynei

<400> SEQUENCE: 24
aagcatgact acatatggat attgttcgat catcatcaaa ttgatgttgg cagcgaaata      60
accatagcca ttatcacccc aagtggtatc ccaactgttt cgtacgatcc aataatcaac     120
accttgtgta ttaccgtaac caacaatgtt gacggcatga tagtttggtt gataaccatt     180

```
gtcgtgttgc atgattgttc gtccatcata atgtcggaaa gcgttcaaat ctttgatgcc    240
aataatgacg gcaacggctg tatgtgtttg agtcaaagct tgacggattt tgttcgagtc    300
tggtggcgaa atttgcaat agttcttgag accgtaacgt tgtgcatttg gtcgatggca     360
tgattgttct cgtgcaacgt atggatagta gtgttcttgg acgacaccat tttgttggat    420
gtattcaatt ccgcgtggaa ttgtatcacc atggcaaccg ttttgtgaag cacaatcgac    480
taattcttgt tcagcaagat ccaaagacat gttgcggtag gccaaataag ctgactcagt    540
tgaggcaaca ccagagaaag cccagcatga accacagcct ccttgcatac ggattggagt    600
tacagttcgc agtgaacgta aatcaagttc cgatggtaaa ctcactgagt taatactgca    660
agcataagtt tcagcattca aatcgaattg agttttgagt tgttcaaaag cattagcatt    720
catcaaaaat tggttttga attcatccaa tgacaaatcg dacaaatggt tgatggcacc     780
tttgtttgat tccacatatt tcaatgattc caaaaagttt ttacgggcaa cttcttcctt    840 ttcagggta gcataggttt tgttgaaggc ttttttgaat tcttcaaaag ttttgatcga     900
agctggacg                                                            909
```

```
<210> SEQ ID NO 25
<211> LENGTH: 669
<212> TYPE: DNA
<213> ORGANISM: Euroglyphus maynei
<220> FEATURE:
<221> NAME/KEY: CDS
<222> LOCATION: (1)..(669)

<400> SEQUENCE: 25
```

```
act tat gct tgc agt att aac tca gtg agt tta cca tcg gaa ctt gat     48
Thr Tyr Ala Cys Ser Ile Asn Ser Val Ser Leu Pro Ser Glu Leu Asp
 1               5                  10                  15 tta cgt tca ctg cga act gta act cca atc cgt atg caa gga ggc tgt     96
Leu Arg Ser Leu Arg Thr Val Thr Pro Ile Arg Met Gln Gly Gly Cys
             20                  25                  30 ggt tca tgc tgg gct ttc tct ggt gtt gcc tca act gag tca gct tat    144
Gly Ser Cys Trp Ala Phe Ser Gly Val Ala Ser Thr Glu Ser Ala Tyr
         35                  40                  45 ttg gcc tac cgc aac atg tct ttg gat ctt gct gaa caa gaa tta gtc    192
Leu Ala Tyr Arg Asn Met Ser Leu Asp Leu Ala Glu Gln Glu Leu Val
     50                  55                  60 gat tgt gct tca caa aac ggt tgc cat ggt gat aca att cca cgc gga    240
Asp Cys Ala Ser Gln Asn Gly Cys His Gly Asp Thr Ile Pro Arg Gly
 65                  70                  75                  80 att gaa tac atc caa caa aat ggt gtc gtc caa gaa cac tac tat cca    288
Ile Glu Tyr Ile Gln Gln Asn Gly Val Val Gln Glu His Tyr Tyr Pro
                 85                  90                  95 tac gtt gca cga gaa caa tca tgc cat cga cca aat gca caa cgt tac    336
Tyr Val Ala Arg Glu Gln Ser Cys His Arg Pro Asn Ala Gln Arg Tyr
            100                 105                 110 ggt ctc aag aac tat tgc caa att tcg cca cca gac tcg aac aaa atc    384
Gly Leu Lys Asn Tyr Cys Gln Ile Ser Pro Pro Asp Ser Asn Lys Ile
        115                 120                 125 cgt caa gct ttg act caa aca cat aca gcc gtt gcc gtc att att ggc    432
Arg Gln Ala Leu Thr Gln Thr His Thr Ala Val Ala Val Ile Ile Gly
    130                 135                 140 atc aaa gat ttg aac gct ttc cga cat tat gat gga cga aca atc atg    480
Ile Lys Asp Leu Asn Ala Phe Arg His Tyr Asp Gly Arg Thr Ile Met
145                 150                 155                 160 caa cac gac aat ggt tat caa cca aac tat cat gcc gtc aac att gtt    528
Gln His Asp Asn Gly Tyr Gln Pro Asn Tyr His Ala Val Asn Ile Val
```

```
                           165                 170                 175
ggt  tac  ggt  aat  aca  caa  ggt  gtt  gat  tat  tgg  atc  gta  cga  aac  agt    576
Gly  Tyr  Gly  Asn  Thr  Gln  Gly  Val  Asp  Tyr  Trp  Ile  Val  Arg  Asn  Ser
              180                           185                       190 tgg  gat  acc  act  tgg  ggt  gat  aat  ggc  tat  ggt  tat  ttc  gct  gcc  aac    624
Trp  Asp  Thr  Thr  Trp  Gly  Asp  Asn  Gly  Tyr  Gly  Tyr  Phe  Ala  Ala  Asn
         195                           200                       205 atc  aat  ttg  atg  atg  atc  gaa  caa  tat  cca  tat  gta  gtc  atg  ctt         669
Ile  Asn  Leu  Met  Met  Ile  Glu  Gln  Tyr  Pro  Tyr  Val  Val  Met  Leu
         210                           215                       220

<210> SEQ ID NO 26
<211> LENGTH: 223
<212> TYPE: PRT
<213> ORGANISM: Euroglyphus maynei

<400> SEQUENCE: 26

Thr Tyr Ala Cys Ser Ile Asn Ser Val Ser Leu Pro Ser Glu Leu Asp
 1               5                  10                  15

Leu Arg Ser Leu Arg Thr Val Thr Pro Ile Arg Met Gln Gly Gly Cys
             20                  25                  30

Gly Ser Cys Trp Ala Phe Ser Gly Val Ala Ser Thr Glu Ser Ala Tyr
         35                  40                  45

Leu Ala Tyr Arg Asn Met Ser Leu Asp Leu Ala Glu Gln Glu Leu Val
     50                  55                  60

Asp Cys Ala Ser Gln Asn Gly Cys His Gly Asp Thr Ile Pro Arg Gly
 65                  70                  75                  80

Ile Glu Tyr Ile Gln Gln Asn Gly Val Gln His Tyr Tyr Pro
                 85                  90                  95

Tyr Val Ala Arg Glu Gln Ser Cys His Arg Pro Asn Ala Gln Arg Tyr
             100                 105                 110

Gly Leu Lys Asn Tyr Cys Gln Ile Ser Pro Pro Asp Ser Asn Lys Ile
         115                 120                 125

Arg Gln Ala Leu Thr Gln Thr His Thr Ala Val Ala Val Ile Ile Gly
     130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
            180                 185                 190

Trp Asp Thr Thr Trp Gly Asp Asn Gly Tyr Gly Tyr Phe Ala Ala Asn
        195                 200                 205

Ile Asn Leu Met Met Ile Glu Gln Tyr Pro Tyr Val Val Met Leu
        210                 215                 220

<210> SEQ ID NO 27
<211> LENGTH: 669
<212> TYPE: DNA
<213> ORGANISM: Euroglyphus maynei

<400> SEQUENCE: 27
aagcatgact acatatggat attgttcgat catcatcaaa ttgatgttgg cagcgaaata      60
accatagcca ttatcacccc aagtggtatc ccaactgttt cgtacgatcc aataatcaac     120
accttgtgta ttaccgtaac caacaatgtt gacggcatga tagtttggtt gataaccatt     180
gtcgtgttgc atgattgttc gtccatcata atgtcggaaa gcgttcaaat ctttgatgcc     240
```

-continued

```
aataatgacg gcaacggctg tatgtgtttg agtcaaagct tgacggattt tgttcgagtc    300
tggtggcgaa atttggcaat agttcttgag accgtaacgt tgtgcatttg gtcgatggca    360
tgattgttct cgtgcaacgt atggatagta gtgttcttgg acgacaccat tttgttggat    420
gtattcaatt ccgcgtggaa ttgtatcacc atggcaaccg ttttgtgaag cacaatcgac    480
taattcttgt tcagcaagat ccaaagacat gttgcggtag gccaaataag ctgactcagt    540
tgaggcaaca ccagagaaag cccagcatga accacagcct ccttgcatac ggattggagt    600
tacagttcgc agtgaacgta aatcaagttc cgatggtaaa ctcactgagt taatactgca    660
agcataagt                                                            669

<210> SEQ ID NO 28
<211> LENGTH: 909
<212> TYPE: DNA
<213> ORGANISM: Dermatophagoides farinae
<220> FEATURE:
<221> NAME/KEY: CDS
<222> LOCATION: (1)..(909)

<400> SEQUENCE: 28 aga cca gct tca atc aaa act ttt gaa gaa ttc aaa aaa gcc ttc aac     48
Arg Pro Ala Ser Ile Lys Thr Phe Glu Glu Phe Lys Lys Ala Phe Asn
 1               5                  10                  15 aaa aac tat gcc acc gtt gaa gag gaa gaa gtt gcc cgt aaa aac ttt     96
Lys Asn Tyr Ala Thr Val Glu Glu Glu Glu Val Ala Arg Lys Asn Phe
             20                  25                  30 ttg gaa tca ttg aaa tat gtt gaa gct aac aaa ggt gcc atc aac cat    144
Leu Glu Ser Leu Lys Tyr Val Glu Ala Asn Lys Gly Ala Ile Asn His
         35                  40                  45 ttg tcc gat ttg tca ttg gat gaa ttc aaa aac cgt tat ttg atg agt    192
Leu Ser Asp Leu Ser Leu Asp Glu Phe Lys Asn Arg Tyr Leu Met Ser
     50                  55                  60 gct gaa gct ttt gaa caa ctc aaa act caa ttc gat ttg aat gcc gaa    240
Ala Glu Ala Phe Glu Gln Leu Lys Thr Gln Phe Asp Leu Asn Ala Glu
 65                  70                  75                  80 aca agc gct tgc cgt atc aat tcg gtt aac gtt cca tcg gaa ttg gat    288
Thr Ser Ala Cys Arg Ile Asn Ser Val Asn Val Pro Ser Glu Leu Asp
                 85                  90                  95 tta cga tca ctg cga act gtc act cca atc cgt atg caa gga ggc tgt    336
Leu Arg Ser Leu Arg Thr Val Thr Pro Ile Arg Met Gln Gly Gly Cys
            100                 105                 110 ggt tca tgt tgg gct ttc tct ggt gtt gcc gca act gaa tca gct tat    384
Gly Ser Cys Trp Ala Phe Ser Gly Val Ala Ala Thr Glu Ser Ala Tyr
        115                 120                 125 ttg gcc tac cgt aac acg tct ttg gat ctt tct gaa cag gaa ctc gtc    432
Leu Ala Tyr Arg Asn Thr Ser Leu Asp Leu Ser Glu Gln Glu Leu Val
    130                 135                 140 gat tgc gca tct caa cac gga tgt cac ggc gat aca ata cca aga ggc    480
Asp Cys Ala Ser Gln His Gly Cys His Gly Asp Thr Ile Pro Arg Gly
145                 150                 155                 160 atc gaa tac atc caa caa aat ggt gtc gtt gaa gaa aga agc tat cca    528
Ile Glu Tyr Ile Gln Gln Asn Gly Val Val Glu Glu Arg Ser Tyr Pro
                165                 170                 175 tac gtt gca aga gaa caa aga tgc aga aga cca aat tcg caa cat tac    576
Tyr Val Ala Arg Glu Gln Arg Cys Arg Arg Pro Asn Ser Gln His Tyr
            180                 185                 190 ggt atc tca aac tac tgc caa att tat cca cca gat gtg aaa caa atc    624
Gly Ile Ser Asn Tyr Cys Gln Ile Tyr Pro Pro Asp Val Lys Gln Ile
        195                 200                 205 cgt gaa gct ttg act caa aca cac aca gct att gcc gtc att att ggc    672
Arg Glu Ala Leu Thr Gln Thr His Thr Ala Ile Ala Val Ile Ile Gly
```

```
                Arg Glu Ala Leu Thr Gln Thr His Thr Ala Ile Ala Val Ile Ile Gly
                    210                 215                 220 atc aaa gat ttg aga gct ttc caa cat tat gat gga cga aca atc att            720
Ile Lys Asp Leu Arg Ala Phe Gln His Tyr Asp Gly Arg Thr Ile Ile
225                 230                 235                 240 caa cat gac aat ggt tat caa cca aac tat cat gcc gtc aac att gtc            768
Gln His Asp Asn Gly Tyr Gln Pro Asn Tyr His Ala Val Asn Ile Val
                245                 250                 255 ggt tac gga agt aca caa ggc gac gat tat tgg atc gta cga aac agt            816
Gly Tyr Gly Ser Thr Gln Gly Asp Asp Tyr Trp Ile Val Arg Asn Ser
                260                 265                 270 tgg gat act acc tgg gga gat agc gga tac gga tat ttc caa gcc gga            864
Trp Asp Thr Thr Trp Gly Asp Ser Gly Tyr Gly Tyr Phe Gln Ala Gly
            275                 280                 285 aac aac ctc atg atg atc gaa caa tat cca tat gtt gta atc atg                909
Asn Asn Leu Met Met Ile Glu Gln Tyr Pro Tyr Val Val Ile Met
        290                 295                 300

<210> SEQ ID NO 29
<211> LENGTH: 303
<212> TYPE: PRT
<213> ORGANISM: Dermatophagoides farinae

<400> SEQUENCE: 29

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
    50                  55                  60

Ala Glu Ala Phe Glu Gln Leu Lys Thr Gln Phe Asp Leu Asn Ala Glu
65                  70                  75                  80

Thr Ser Ala Cys Arg Ile Asn Ser Val Asn Val Pro Ser Glu Leu Asp
                85                  90                  95

Leu Arg Ser Leu Arg Thr Val Thr Pro Ile Arg Met Gln Gly Gly Cys
            100                 105                 110

Gly Ser Cys Trp Ala Phe Ser Gly Val Ala Ala Thr Glu Ser Ala Tyr
        115                 120                 125

Leu Ala Tyr Arg Asn Thr Ser Leu Asp Leu Ser Glu Gln Glu Leu Val
    130                 135                 140

Asp Cys Ala Ser Gln His Gly Cys His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Arg Cys Arg Arg Pro Asn Ser Gln His Tyr
            180                 185                 190

Gly Ile Ser Asn Tyr Cys Gln Ile Tyr Pro Pro Asp Val Lys Gln Ile
        195                 200                 205

Arg Glu Ala Leu Thr Gln Thr His Thr Ala Ile Ala Val Ile Ile Gly
    210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Asp Asp Tyr Trp Ile Val Arg Asn Ser
```

```
              260                 265                 270
Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
        290                 295                 300

<210> SEQ ID NO 30
<211> LENGTH: 909
<212> TYPE: DNA
<213> ORGANISM: Dermatophagoides farinae

<400> SEQUENCE: 30
catgattaca acatatggat attgttcgat catcatgagg ttgtttccgg cttggaaata    60
tccgtatccg ctatctcccc aggtagtatc ccaactgttt cgtacgatcc aataatcgtc   120
gccttgtgta cttccgtaac cgacaatgtt gacggcatga tagtttggtt gataaccatt   180
gtcatgttga atgattgttc gtccatcata atgttggaaa gctctcaaat ctttgatgcc   240
aataatgacg gcaatagctg tgtgtgtttg agtcaaagct tcacggattt gtttcacatc   300
tggtggataa atttggcagt agtttgagat accgtaatgt tgcgaatttg gtcttctgca   360
tctttgttct cttgcaacgt atggatagct tctttcttca acgacaccat tttgttggat   420
gtattcgatg cctcttggta ttgtatcgcc gtgacatccg tgttgagatg cgcaatcgac   480
gagttcctgt tcagaaagat ccaaagacgt gttacggtag gccaaataag ctgattcagt   540
tgcggcaaca ccagagaaag cccaacatga accacagcct ccttgcatac ggattggagt   600
gacagttcgc agtgatcgta aatccaattc cgatggaacg ttaaccgaat tgatacggca   660
agcgcttgtt tcggcattca atcgaattg agttttgagt tgttcaaaag cttcagcact   720
catcaaataa cggttttga attcatccaa tgacaaatcg acaaatggt tgatggcacc    780 tttgttagct tcaacatatt tcaatgattc caaaaagttt ttacgggcaa cttcttcctc   840
ttcaacggtg gcatagtttt tgttgaaggc ttttttgaat tcttcaaaag ttttgattga   900
agctggtct                                                             909

<210> SEQ ID NO 31
<211> LENGTH: 669
<212> TYPE: DNA
<213> ORGANISM: Dermatophagoides farinae
<220> FEATURE:
<221> NAME/KEY: CDS
<222> LOCATION: (1)..(669)

<400> SEQUENCE: 31 aca agc gct tgc cgt atc aat tcg gtt aac gtt cca tcg gaa ttg gat    48
Thr Ser Ala Cys Arg Ile Asn Ser Val Asn Val Pro Ser Glu Leu Asp
  1               5                  10                  15 tta cga tca ctg cga act gtc act cca atc cgt atg caa gga ggc tgt    96
Leu Arg Ser Leu Arg Thr Val Thr Pro Ile Arg Met Gln Gly Gly Cys
             20                  25                  30 ggt tca tgt tgg gct ttc tct ggt gtc gcc gca act gaa tca gct tat   144
Gly Ser Cys Trp Ala Phe Ser Gly Val Ala Ala Thr Glu Ser Ala Tyr
         35                  40                  45 ttg gcc tac cgt aac acg tct ttg gat ctt tct gaa cag gaa ctc gtc   192
Leu Ala Tyr Arg Asn Thr Ser Leu Asp Leu Ser Glu Gln Glu Leu Val
     50                  55                  60 gat tgc gca tct caa cac gga tgt cac ggc gat aca ata cca aga ggc   240
Asp Cys Ala Ser Gln His Gly Cys His Gly Asp Thr Ile Pro Arg Gly
 65                  70                  75                  80 atc gaa tac atc caa caa aat ggt gtc gtt gaa gaa aga agc tat cca   288
```

```
Ile Glu Tyr Ile Gln Gln Asn Gly Val Val Glu Glu Arg Ser Tyr Pro
             85                  90                  95 tac gtt gca aga gaa caa aga tgc aga aga cca aat tcg caa cat tac      336
Tyr Val Ala Arg Glu Gln Arg Cys Arg Arg Pro Asn Ser Gln His Tyr
                100                 105                 110 ggt atc tca aac tac tgc caa att tat cca cca gat gtg aaa caa atc      384
Gly Ile Ser Asn Tyr Cys Gln Ile Tyr Pro Pro Asp Val Lys Gln Ile
            115                 120                 125 cgt gaa gct ttg act caa aca cac aca gct att gcc gtc att att ggc      432
Arg Glu Ala Leu Thr Gln Thr His Thr Ala Ile Ala Val Ile Ile Gly
        130                 135                 140 att aaa gat ttg aga gct ttt caa cat tat gat gga cga aca atc att      480
Ile Lys Asp Leu Arg Ala Phe Gln His Tyr Asp Gly Arg Thr Ile Ile
145                 150                 155                 160 caa cat gac aat ggt tat caa cca aac tat cat gcc gtc aac att gtc      528
Gln His Asp Asn Gly Tyr Gln Pro Asn Tyr His Ala Val Asn Ile Val
                165                 170                 175 ggt tac gga agt aca caa ggc gtc gat tat tgg atc gta cga aac agt      576
Gly Tyr Gly Ser Thr Gln Gly Val Asp Tyr Trp Ile Val Arg Asn Ser
            180                 185                 190 tgg gat act acc tgg ggt gat agc gga tac gga tat ttc caa gcc gga      624
Trp Asp Thr Thr Trp Gly Asp Ser Gly Tyr Gly Tyr Phe Gln Ala Gly
        195                 200                 205 aac aac ctc atg atg atc gaa caa tat cca tat gtt gta atc atg          669
Asn Asn Leu Met Met Ile Glu Gln Tyr Pro Tyr Val Val Ile Met
    210                 215                 220

<210> SEQ ID NO 32
<211> LENGTH: 223
<212> TYPE: PRT
<213> ORGANISM: Dermatophagoides farinae

<400> SEQUENCE: 32

Thr Ser Ala Cys Arg Ile Asn Ser Val Asn Val Pro Ser Glu Leu Asp
 1               5                  10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
        35                  40                  45

Leu Ala Tyr Arg Asn Thr Ser Leu Asp Leu Ser Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln Gln Asn Gly Val Val Glu Glu Arg Ser Tyr Pro
                85                  90                  95

Tyr Val Ala Arg Glu Gln Arg Cys Arg Arg Pro Asn Ser Gln His Tyr
            100                 105                 110

Gly Ile Ser Asn Tyr Cys Gln Ile Tyr Pro Pro Asp Val Lys Gln Ile
        115                 120                 125

Arg Glu Ala Leu Thr Gln Thr His Thr Ala Ile Ala Val Ile Ile Gly
    130                 135                 140

Ile Lys Asp Leu Arg Ala Phe Gln His Tyr Asp Gly Arg Thr Ile Ile
145                 150                 155                 160

Gln His Asp Asn Gly Tyr Gln Pro Asn Tyr His Ala Val Asn Ile Val
                165                 170                 175

Gly Tyr Gly Ser Thr Gln Gly Val Asp Tyr Trp Ile Val Arg Asn Ser
            180                 185                 190

Trp Asp Thr Thr Trp Gly Asp Ser Gly Tyr Gly Tyr Phe Gln Ala Gly
```

```
                195                 200                 205
Asn Asn Leu Met Met Ile Glu Gln Tyr Pro Tyr Val Val Ile Met
    210                 215                 220

<210> SEQ ID NO 33
<211> LENGTH: 669
<212> TYPE: DNA
<213> ORGANISM: Dermatophagoides farinae

<400> SEQUENCE: 33
catgattaca acatatggat attgttcgat catcatgagg ttgtttccgg cttggaaata      60
tccgtatccg ctatcacccc aggtagtatc ccaactgttt cgtacgatcc aataatcgac     120
gccttgtgta cttccgtaac cgacaatgtt gacggcatga tagtttggtt gataaccatt     180
gtcatgttga atgattgttc gtccatcata atgttgaaaa gctctcaaat ctttaatgcc     240
aataatgacg gcaatagctg tgtgtgtttg agtcaaagct tcacggattt gtttcacatc     300
tggtggataa atttggcagt agtttgagat accgtaatgt tgcgaatttg gtcttctgca     360
tctttgttct cttgcaacgt atggatagct tctttcttca acgacaccat tttgttggat     420
gtattcgatg cctcttggta ttgtatcgcc gtgcatccg tgttgagatg cgcaatcgac       480
gagttcctgt tcagaaagat ccaaagacgt gttacggtag ccaaataag ctgattcagt       540 tgcggcgaca ccagagaaag cccaacatga accacagcct ccttgcatac ggattggagt     600
gacagttcgc agtgatcgta aatccaattc cgatggaacg ttaaccgaat tgatacggca     660
agcgcttgt                                                              669

<210> SEQ ID NO 34
<211> LENGTH: 909
<212> TYPE: DNA
<213> ORGANISM: Dermatophagoides farinae
<220> FEATURE:
<221> NAME/KEY: CDS
<222> LOCATION: (1)..(909)

<400> SEQUENCE: 34 cgt ccg gct tca atc aaa act ttt gaa gaa ttc aaa aaa gcc ttc aac        48
Arg Pro Ala Ser Ile Lys Thr Phe Glu Glu Phe Lys Lys Ala Phe Asn
 1               5                  10                  15 aaa aac tat gcc acc gtt gaa gag gaa gaa gtt gcc cgt aaa aac ttt        96
Lys Asn Tyr Ala Thr Val Glu Glu Glu Glu Val Ala Arg Lys Asn Phe
            20                  25                  30 ttg gaa tca ttg aaa tat gtt gaa gct aac aaa ggt gcc atc aac cat       144
Leu Glu Ser Leu Lys Tyr Val Glu Ala Asn Lys Gly Ala Ile Asn His
        35                  40                  45 ttg tcc gat ttg tca ttg gat gaa ttc aaa aac cgt tat ttg atg agt       192
Leu Ser Asp Leu Ser Leu Asp Glu Phe Lys Asn Arg Tyr Leu Met Ser
    50                  55                  60 gct gaa gct ttt gaa caa ctc aaa act caa ttc gat ttg aat gcc gaa       240
Ala Glu Ala Phe Glu Gln Leu Lys Thr Gln Phe Asp Leu Asn Ala Glu
65                  70                  75                  80 aca agc gct tgt cgt atc aat tcg gtt aac gtt cca tcg gaa ttg gat       288
Thr Ser Ala Cys Arg Ile Asn Ser Val Asn Val Pro Ser Glu Leu Asp
                85                  90                  95 tta cga tca ctg cga act gtc act cca atc cgt atg caa gga ggc tgt       336
Leu Arg Ser Leu Arg Thr Val Thr Pro Ile Arg Met Gln Gly Gly Cys
            100                 105                 110 ggt tca tgt tgg gct ttc tct ggt gtc gcc gca act gaa tca gct tat       384
Gly Ser Cys Trp Ala Phe Ser Gly Val Ala Ala Thr Glu Ser Ala Tyr
        115                 120                 125
```

```
ttg gcc tac cgt aac acg tct ttg gat ctt tct gaa cag gaa ctc gtc      432
Leu Ala Tyr Arg Asn Thr Ser Leu Asp Leu Ser Glu Gln Glu Leu Val
    130                 135                 140 gat tgc gca tct caa cac gga tgt cac ggc gat aca ata cca aga ggc      480
Asp Cys Ala Ser Gln His Gly Cys His Gly Asp Thr Ile Pro Arg Gly
145                 150                 155                 160 atc gaa tac atc caa caa aat ggt gtc gtt gaa gaa aga agc tat cca      528
Ile Glu Tyr Ile Gln Gln Asn Gly Val Val Glu Glu Arg Ser Tyr Pro
                165                 170                 175 tac gtt gca cgt gaa caa cgt tgc cgt cgt cca aat tcg caa cat tac      576
Tyr Val Ala Arg Glu Gln Arg Cys Arg Arg Pro Asn Ser Gln His Tyr
            180                 185                 190 ggt atc tca aac tac tgc caa att tat cca cca gat gtg aaa caa atc      624
Gly Ile Ser Asn Tyr Cys Gln Ile Tyr Pro Pro Asp Val Lys Gln Ile
        195                 200                 205 cgt gaa gct ttg act caa aca cac aca gct att gcc gtc att att ggc      672
Arg Glu Ala Leu Thr Gln Thr His Thr Ala Ile Ala Val Ile Ile Gly
    210                 215                 220 att aaa gat ttg aga gct ttt caa cat tat gat gga cga aca atc att      720
Ile Lys Asp Leu Arg Ala Phe Gln His Tyr Asp Gly Arg Thr Ile Ile
225                 230                 235                 240 caa cat gac aat ggt tat caa cca aac tat cat gcc gtc aac att gtc      768
Gln His Asp Asn Gly Tyr Gln Pro Asn Tyr His Ala Val Asn Ile Val
                245                 250                 255 ggt tac gga agt aca caa ggc gtc gat tat tgg atc gtg cga aac agt      816
Gly Tyr Gly Ser Thr Gln Gly Val Asp Tyr Trp Ile Val Arg Asn Ser
            260                 265                 270 tgg gat act acc tgg ggt gat agc gga tac gga tat ttc caa gcc gga      864
Trp Asp Thr Thr Trp Gly Asp Ser Gly Tyr Gly Tyr Phe Gln Ala Gly
        275                 280                 285 aac aac ctc atg atg atc gaa caa tat cca tac gtt gta atc atg           909
Asn Asn Leu Met Met Ile Glu Gln Tyr Pro Tyr Val Val Ile Met
    290                 295                 300
```

<210> SEQ ID NO 35
<211> LENGTH: 303
<212> TYPE: PRT
<213> ORGANISM: Dermatophagoides farinae

<400> SEQUENCE: 35

```
Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
    50                  55                  60

Ala Glu Ala Phe Glu Gln Leu Lys Thr Gln Phe Asp Leu Asn Ala Glu
65                  70                  75                  80

Thr Ser Ala Cys Arg Ile Asn Ser Val Asn Val Pro Ser Glu Leu Asp
                85                  90                  95

Leu Arg Ser Leu Arg Thr Val Thr Pro Ile Arg Met Gln Gly Gly Cys
            100                 105                 110

Gly Ser Cys Trp Ala Phe Ser Gly Val Ala Ala Thr Glu Ser Ala Tyr
        115                 120                 125

Leu Ala Tyr Arg Asn Thr Ser Leu Asp Leu Ser Glu Gln Glu Leu Val
    130                 135                 140

Asp Cys Ala Ser Gln His Gly Cys His Gly Asp Thr Ile Pro Arg Gly
```

```
                145                 150                 155                 160
Ile Glu Tyr Ile Gln Gln Asn Gly Val Val Glu Arg Ser Tyr Pro
                165                 170                 175
Tyr Val Ala Arg Glu Gln Arg Cys Arg Arg Pro Asn Ser Gln His Tyr
            180                 185                 190
Gly Ile Ser Asn Tyr Cys Gln Ile Tyr Pro Pro Asp Val Lys Gln Ile
                195                 200                 205
Arg Glu Ala Leu Thr Gln Thr His Thr Ala Ile Ala Val Ile Ile Gly
        210                 215                 220
Ile Lys Asp Leu Arg Ala Phe Gln His Tyr Asp Gly Arg Thr Ile Ile
225                 230                 235                 240
Gln His Asp Asn Gly Tyr Gln Pro Asn Tyr His Ala Val Asn Ile Val
                245                 250                 255
Gly Tyr Gly Ser Thr Gln Gly Val Asp Tyr Trp Ile Val Arg Asn Ser
            260                 265                 270
Trp Asp Thr Thr Trp Gly Asp Ser Gly Tyr Gly Tyr Phe Gln Ala Gly
            275                 280                 285
Asn Asn Leu Met Met Ile Glu Gln Tyr Pro Tyr Val Val Ile Met
            290                 295                 300

<210> SEQ ID NO 36
<211> LENGTH: 909
<212> TYPE: DNA
<213> ORGANISM: Dermatophagoides farinae

<400> SEQUENCE: 36
catgattaca acgtatggat attgttcgat catcatgagg ttgtttccgg cttggaaata      60
tccgtatccg ctatcacccc aggtagtatc ccaactgttt cgcacgatcc aataatcgac     120
gccttgtgta cttccgtaac cgacaatgtt gacggcatga tagtttggtt gataaccatt     180
gtcatgttga atgattgttc gtccatcata atgttgaaaa gctctcaaat ctttaatgcc     240
aataatgacg gcaatagctg tgtgtgtttg agtcaaagct tcacggattt gtttcacatc     300
tggtggataa atttggcagt agtttgagat accgtaatgt tgcgaatttg acgacggca      360
acgttgttca cgtgcaacgt atggatagct tctttcttca acgacaccat tttgttggat     420
gtattcgatg cctcttggta ttgtatcgcc gtgacatccg tgttgagatg cgcaatcgac     480
gagttcctgt tcagaaagat ccaaagacgt gttacggtag gccaaataag ctgattcagt     540
tgcggcgaca ccagagaaag cccaacatga accacagcct ccttgcatac ggattggagt     600
gacagttcgc agtgatcgta aatccaattc cgatggaacg ttaaccgaat tgatacgaca     660
agcgcttgtt tcggcattca aatcgaattg agttttgagt tgttcaaaag cttcagcact     720
catcaaataa cggttttttga attcatccaa tgacaaatcg acaaatggt tgatggcacc     780
tttgttagct tcaacatatt tcaatgattc caaaaagttt ttacgggcaa cttcttcctc     840
ttcaacggtg gcatagtttt tgttgaaggc ttttttgaat tcttcaaaag ttttgattga     900
agccggacg                                                              909

<210> SEQ ID NO 37
<211> LENGTH: 909
<212> TYPE: DNA
<213> ORGANISM: Dermatophagoides farinae
<220> FEATURE:
<221> NAME/KEY: CDS
<222> LOCATION: (1)..(909)

<400> SEQUENCE: 37
```

```
aga cca gct tca atc aaa act ttt gaa gaa ttc aaa aaa gcc ttc aac      48
Arg Pro Ala Ser Ile Lys Thr Phe Glu Glu Phe Lys Lys Ala Phe Asn
 1               5                  10                  15 aaa aac tat gcc acc gtt gaa gag gaa gaa gtt gcc cgt aaa aac ttt      96
Lys Asn Tyr Ala Thr Val Glu Glu Glu Glu Val Ala Arg Lys Asn Phe
             20                  25                  30 ttg gaa tca ttg aaa tat gtt gaa gct aac aaa ggt gcc atc aac cat     144
Leu Glu Ser Leu Lys Tyr Val Glu Ala Asn Lys Gly Ala Ile Asn His
         35                  40                  45 ttg tcc gat ttg tca ttg gat gaa ttc aaa aac cgt tat ttg atg agt     192
Leu Ser Asp Leu Ser Leu Asp Glu Phe Lys Asn Arg Tyr Leu Met Ser
     50                  55                  60 gct gaa gct ttt gaa caa ctc aaa act caa ttc gat ttg aat gcc gaa     240
Ala Glu Ala Phe Glu Gln Leu Lys Thr Gln Phe Asp Leu Asn Ala Glu
 65              70                  75                  80 aca agc gct tgc cgt atc aat tcg gtt aac gtt cca tcg gaa ttg gat     288
Thr Ser Ala Cys Arg Ile Asn Ser Val Asn Val Pro Ser Glu Leu Asp
             85                  90                  95 tta cga tca ctg cga act gtc act cca atc cgt atg caa gga ggc tgt     336
Leu Arg Ser Leu Arg Thr Val Thr Pro Ile Arg Met Gln Gly Gly Cys
         100                 105                 110 ggt tca tgt tgg gct ttc tct ggt gtt gcc gca act gaa tca gct tat     384
Gly Ser Cys Trp Ala Phe Ser Gly Val Ala Ala Thr Glu Ser Ala Tyr
     115                 120                 125 ttg gcc tac cgt caa acg tct ttg gat ctt tct gaa cag gaa ctc gtc     432
Leu Ala Tyr Arg Gln Thr Ser Leu Asp Leu Ser Glu Gln Glu Leu Val
130                 135                 140 gat tgc gca tct caa cac gga tgt cac ggc gat aca ata cca aga ggc     480
Asp Cys Ala Ser Gln His Gly Cys His Gly Asp Thr Ile Pro Arg Gly
145                 150                 155                 160 atc gaa tac atc caa caa aat ggt gtc gtt gaa gaa aga agc tat cca     528
Ile Glu Tyr Ile Gln Gln Asn Gly Val Val Glu Glu Arg Ser Tyr Pro
             165                 170                 175 tac gtt gca aga gaa caa aga tgc aga aga cca aat tcg caa cat tac     576
Tyr Val Ala Arg Glu Gln Arg Cys Arg Arg Pro Asn Ser Gln His Tyr
         180                 185                 190 ggt atc tca aac tac tgc caa att tat cca cca gat gtg aaa caa atc     624
Gly Ile Ser Asn Tyr Cys Gln Ile Tyr Pro Pro Asp Val Lys Gln Ile
     195                 200                 205 cgt gaa gct ttg act caa aca cac aca gct att gcc gtc att att ggc     672
Arg Glu Ala Leu Thr Gln Thr His Thr Ala Ile Ala Val Ile Ile Gly
210                 215                 220 atc aaa gat ttg aga gct ttc caa cat tat gat gga cga aca atc att     720
Ile Lys Asp Leu Arg Ala Phe Gln His Tyr Asp Gly Arg Thr Ile Ile
225                 230                 235                 240 caa cat gac aat ggt tat caa cca aac tat cat gcc gtc aac att gtc     768
Gln His Asp Asn Gly Tyr Gln Pro Asn Tyr His Ala Val Asn Ile Val
             245                 250                 255 ggt tac gga agt aca caa ggc gac gat tat tgg atc gta cga aac agt     816
Gly Tyr Gly Ser Thr Gln Gly Asp Asp Tyr Trp Ile Val Arg Asn Ser
         260                 265                 270 tgg gat act acc tgg gga gat agc gga tac gga tat ttc caa gcc gga     864
Trp Asp Thr Thr Trp Gly Asp Ser Gly Tyr Gly Tyr Phe Gln Ala Gly
     275                 280                 285 aac aac ctc atg atg atc gaa caa tat cca tat gtt gta atc atg         909
Asn Asn Leu Met Met Ile Glu Gln Tyr Pro Tyr Val Val Ile Met
290                 295                 300

<210> SEQ ID NO 38
<211> LENGTH: 303
<212> TYPE: PRT
```

<213> ORGANISM: Dermatophagoides farinae

<400> SEQUENCE: 38

```
Arg Pro Ala Ser Ile Lys Thr Phe Glu Glu Phe Lys Ala Phe Asn
 1               5                  10                  15
Lys Asn Tyr Ala Thr Val Glu Glu Glu Val Ala Arg Lys Asn Phe
                20                  25                  30
Leu Glu Ser Leu Lys Tyr Val Glu Ala Asn Lys Gly Ala Ile Asn His
            35                  40                  45
Leu Ser Asp Leu Ser Leu Asp Glu Phe Lys Asn Arg Tyr Leu Met Ser
        50                  55                  60
Ala Glu Ala Phe Glu Gln Leu Lys Thr Gln Phe Asp Leu Asn Ala Glu
 65                 70                  75                  80
Thr Ser Ala Cys Arg Ile Asn Ser Val Asn Val Pro Ser Glu Leu Asp
                85                  90                  95
Leu Arg Ser Leu Arg Thr Val Thr Pro Ile Arg Met Gln Gly Gly Cys
            100                 105                 110
Gly Ser Cys Trp Ala Phe Ser Gly Val Ala Ala Thr Glu Ser Ala Tyr
        115                 120                 125
Leu Ala Tyr Arg Gln Thr Ser Leu Asp Leu Ser Glu Gln Glu Leu Val
    130                 135                 140
Asp Cys Ala Ser Gln His Gly Cys His Gly Asp Thr Ile Pro Arg Gly
145                 150                 155                 160
Ile Glu Tyr Ile Gln Gln Asn Gly Val Val Glu Glu Arg Ser Tyr Pro
                165                 170                 175
Tyr Val Ala Arg Glu Gln Arg Cys Arg Arg Pro Asn Ser Gln His Tyr
            180                 185                 190
Gly Ile Ser Asn Tyr Cys Gln Ile Tyr Pro Pro Asp Val Lys Gln Ile
        195                 200                 205
Arg Glu Ala Leu Thr Gln Thr His Thr Ala Ile Ala Val Ile Ile Gly
    210                 215                 220
Ile Lys Asp Leu Arg Ala Phe Gln His Tyr Asp Gly Arg Thr Ile Ile
225                 230                 235                 240
Gln His Asp Asn Gly Tyr Gln Pro Asn Tyr His Ala Val Asn Ile Val
                245                 250                 255
Gly Tyr Gly Ser Thr Gln Gly Asp Asp Tyr Trp Ile Val Arg Asn Ser
            260                 265                 270
Trp Asp Thr Thr Trp Gly Asp Ser Gly Tyr Gly Tyr Phe Gln Ala Gly
        275                 280                 285
Asn Asn Leu Met Met Ile Glu Gln Tyr Pro Tyr Val Val Ile Met
    290                 295                 300
```

<210> SEQ ID NO 39
<211> LENGTH: 909
<212> TYPE: DNA
<213> ORGANISM: Dermatophagoides farinae

<400> SEQUENCE: 39

| | | | | | |
|---|---|---|---|---|---|
| catgattaca | acatatggat | attgttcgat | catcatgagg | ttgtttccgg | cttggaaata | 60 |
| tccgtatccg | ctatctcccc | aggtagtatc | ccaactgttt | cgtacgatcc | aataatcgtc | 120 |
| gccttgtgta | cttccgtaac | cgacaatgtt | gacggcatga | tagtttggtt | gataaccatt | 180 |
| gtcatgttga | atgattgttc | gtccatcata | atgttggaaa | gctctcaaat | ctttgatgcc | 240 |
| aataatgacg | gcaatagctg | tgtgtgtttg | agtcaaagct | tcacggattt | gtttcacatc | 300 |
| tggtggataa | atttggcagt | agtttgagat | accgtaatgt | tgcgaatttg | gtcttctgca | 360 |

```
tctttgttct cttgcaacgt atggatagct tctttcttca acgacaccat tttgttggat      420
gtattcgatg cctcttggta ttgtatcgcc gtgacatccg tgttgagatg cgcaatcgac      480
gagttcctgt tcagaaagat ccaaagacgt tgacggtag gccaaataag ctgattcagt       540
tgcggcaaca ccagagaaag cccaacatga accacagcct ccttgcatac ggattggagt      600
gacagttcgc agtgatcgta aatccaattc cgatggaacg ttaaccgaat tgatacggca      660
agcgcttgtt tcggcattca aatcgaattg agttttgagt tgttcaaaag cttcagcact      720
catcaaataa cggttttga attcatccaa tgacaaatcg acaaatggt tgatggcacc        780 tttgttagct tcaacatatt tcaatgattc caaaaagttt ttacgggcaa cttcttcctc      840
ttcaacggtg gcatagtttt tgttgaaggc ttttttgaat tcttcaaaag ttttgattga      900
agctggtct                                                             909
```

```
<210> SEQ ID NO 40
<211> LENGTH: 669
<212> TYPE: DNA
<213> ORGANISM: Dermatophagoides farinae
<220> FEATURE:
<221> NAME/KEY: CDS
<222> LOCATION: (1)..(669)

<400> SEQUENCE: 40
```

```
aca agc gct tgc cgt atc aat tcg gtt aac gtt cca tcg gaa ttg gat        48
Thr Ser Ala Cys Arg Ile Asn Ser Val Asn Val Pro Ser Glu Leu Asp
 1               5                  10                  15 tta cga tca ctg cga act gtc act cca atc cgt atg caa gga ggc tgt        96
Leu Arg Ser Leu Arg Thr Val Thr Pro Ile Arg Met Gln Gly Gly Cys
             20                  25                  30 ggt tca tgt tgg gct ttc tct ggt gtt gcc gca act gaa tca gct tat       144
Gly Ser Cys Trp Ala Phe Ser Gly Val Ala Ala Thr Glu Ser Ala Tyr
         35                  40                  45 ttg gcc tac cgt caa acg tct ttg gat ctt tct gaa cag gaa ctc gtc       192
Leu Ala Tyr Arg Gln Thr Ser Leu Asp Leu Ser Glu Gln Glu Leu Val
     50                  55                  60 gat tgc gca tct caa cac gga tgt cac ggc gat aca ata cca aga ggc       240
Asp Cys Ala Ser Gln His Gly Cys His Gly Asp Thr Ile Pro Arg Gly
 65                  70                  75                  80 atc gaa tac atc caa caa aat ggt gtc gtt gaa gaa aga agc tat cca       288
Ile Glu Tyr Ile Gln Gln Asn Gly Val Val Glu Glu Arg Ser Tyr Pro
                 85                  90                  95 tac gtt gca aga gaa caa aga tgc aga aga cca aat tcg caa cat tac       336
Tyr Val Ala Arg Glu Gln Arg Cys Arg Arg Pro Asn Ser Gln His Tyr
            100                 105                 110 ggt atc tca aac tac tgc caa att tat cca cca gat gtg aaa caa atc       384
Gly Ile Ser Asn Tyr Cys Gln Ile Tyr Pro Pro Asp Val Lys Gln Ile
        115                 120                 125 cgt gaa gct ttg act caa aca cac aca gct att gcc gtc att att ggc       432
Arg Glu Ala Leu Thr Gln Thr His Thr Ala Ile Ala Val Ile Ile Gly
    130                 135                 140 atc aaa gat ttg aga gct ttc caa cat tat gat gga cga aca atc att       480
Ile Lys Asp Leu Arg Ala Phe Gln His Tyr Asp Gly Arg Thr Ile Ile
145                 150                 155                 160 caa cat gac aat ggt tat caa cca aac tat cat gcc gtc aac att gtc       528
Gln His Asp Asn Gly Tyr Gln Pro Asn Tyr His Ala Val Asn Ile Val
                165                 170                 175 ggt tac gga agt aca caa ggc gac gat tat tgg atc gta cga aac agt       576
Gly Tyr Gly Ser Thr Gln Gly Asp Asp Tyr Trp Ile Val Arg Asn Ser
            180                 185                 190
```

```
tgg gat act acc tgg gga gat agc gga tac gga tat ttc caa gcc gga    624
Trp Asp Thr Thr Trp Gly Asp Ser Gly Tyr Gly Tyr Phe Gln Ala Gly
        195                 200                 205 aac aac ctc atg atg atc gaa caa tat cca tat gtt gta atc atg        669
Asn Asn Leu Met Met Ile Glu Gln Tyr Pro Tyr Val Val Ile Met
    210                 215                 220

<210> SEQ ID NO 41
<211> LENGTH: 223
<212> TYPE: PRT
<213> ORGANISM: Dermatophagoides farinae

<400> SEQUENCE: 41

Thr Ser Ala Cys Arg Ile Asn Ser Val Asn Val Pro Ser Glu Leu Asp
  1               5                  10                  15

Leu Arg Ser Leu Arg Thr Val Thr Pro Ile Arg Met Gln Gly Gly Cys
             20                  25                  30

Gly Ser Cys Trp Ala Phe Ser Gly Val Ala Ala Thr Glu Ser Ala Tyr
         35                  40                  45

Leu Ala Tyr Arg Gln Thr Ser Leu Asp Leu Ser Glu Gln Glu Leu Val
     50                  55                  60

Asp Cys Ala Ser Gln His Gly Cys His Gly Asp Thr Ile Pro Arg Gly
 65                  70                  75                  80

Ile Glu Tyr Ile Gln Gln Asn Gly Val Val Glu Glu Arg Ser Tyr Pro
                 85                  90                  95

Tyr Val Ala Arg Glu Gln Arg Cys Arg Arg Pro Asn Ser Gln His Tyr
            100                 105                 110

Gly Ile Ser Asn Tyr Cys Gln Ile Tyr Pro Pro Asp Val Lys Gln Ile
        115                 120                 125

Arg Glu Ala Leu Thr Gln Thr His Thr Ala Ile Ala Val Ile Ile Gly
    130                 135                 140

Ile Lys Asp Leu Arg Ala Phe Gln His Tyr Asp Gly Arg Thr Ile Ile
145                 150                 155                 160

Gln His Asp Asn Gly Tyr Gln Pro Asn Tyr His Ala Val Asn Ile Val
                165                 170                 175

Gly Tyr Gly Ser Thr Gln Gly Asp Asp Tyr Trp Ile Val Arg Asn Ser
            180                 185                 190

Trp Asp Thr Thr Trp Gly Asp Ser Gly Tyr Gly Tyr Phe Gln Ala Gly
        195                 200                 205

Asn Asn Leu Met Met Ile Glu Gln Tyr Pro Tyr Val Val Ile Met
    210                 215                 220

<210> SEQ ID NO 42
<211> LENGTH: 669
<212> TYPE: DNA
<213> ORGANISM: Dermatophagoides farinae

<400> SEQUENCE: 42
catgattaca acatatggat attgttcgat catcatgagg ttgtttccgg cttggaaata     60
tccgtatccg ctatctcccc aggtagtatc ccaactgttt cgtacgatcc aataatcgtc    120
gccttgtgta cttccgtaac cgacaatgtt gacggcatga tagtttggtt gataaccatt    180
gtcatgttga atgattgttc gtccatcata atgttgaaaa gctctcaaat cttttgatgcc    240 aataatgacg gcaatagctg tgtgtgtttg agtcaaagct tcacggattt gtttcacatc    300
tggtggataa atttggcagt agtttgagat accgtaatgt tgcgaatttg gtcttctgca    360
tctttgttct cttgcaacgt atggatagct tctttcttca acgacaccat tttgttggat    420
```

```
gtattcgatg cctcttggta ttgtatcgcc gtgacatccg tgttgagatg cgcaatcgac      480
gagttcctgt tcagaaagat ccaaagacgt tgacggtag gccaaataag ctgattcagt       540
tgcggcaaca ccagagaaag cccaacatga accacagcct ccttgcatac ggattggagt      600
gacagttcgc agtgatcgta aatccaattc cgatggaacg ttaaccgaat tgatacggca      660
agcgcttgt                                                               669
```

```
<210> SEQ ID NO 43
<211> LENGTH: 669
<212> TYPE: DNA
<213> ORGANISM: Dermatophagoides farinae
<220> FEATURE:
<221> NAME/KEY: CDS
<222> LOCATION: (1)..(669)

<400> SEQUENCE: 43
```

| aca | agc | gct | tgc | cgt | atc | aat | tcg | gtt | aac | gtt | cca | tcg | gaa | ttg | gat | 48 |
|---|---|---|---|---|---|---|---|---|---|---|---|---|---|---|---|---|
| Thr | Ser | Ala | Cys | Arg | Ile | Asn | Ser | Val | Asn | Val | Pro | Ser | Glu | Leu | Asp | |
| 1 | | | 5 | | | | 10 | | | | 15 | | | | | |

| tta | cga | tca | ctg | cga | act | gtc | act | cca | atc | cgt | atg | caa | gga | ggc | tgt | 96 |
|---|---|---|---|---|---|---|---|---|---|---|---|---|---|---|---|---|
| Leu | Arg | Ser | Leu | Arg | Thr | Val | Thr | Pro | Ile | Arg | Met | Gln | Gly | Gly | Cys | |
| | | 20 | | | | 25 | | | | 30 | | | | | | |

| ggt | tca | tgt | tgg | gct | ttc | tct | ggt | gtc | gcc | gca | act | gaa | tca | gct | tat | 144 |
|---|---|---|---|---|---|---|---|---|---|---|---|---|---|---|---|---|
| Gly | Ser | Cys | Trp | Ala | Phe | Ser | Gly | Val | Ala | Ala | Thr | Glu | Ser | Ala | Tyr | |
| | 35 | | | | 40 | | | | 45 | | | | | | | |

| ttg | gcc | tac | cgt | aac | acg | tct | ttg | gat | ctt | tct | gaa | cag | gaa | ctc | gtc | 192 |
|---|---|---|---|---|---|---|---|---|---|---|---|---|---|---|---|---|
| Leu | Ala | Tyr | Arg | Asn | Thr | Ser | Leu | Asp | Leu | Ser | Glu | Gln | Glu | Leu | Val | |
| 50 | | | | 55 | | | | 60 | | | | | | | | |

| gat | tgc | gca | tct | caa | cac | gga | tgt | cac | ggc | gat | aca | ata | cca | aga | ggc | 240 |
|---|---|---|---|---|---|---|---|---|---|---|---|---|---|---|---|---|
| Asp | Cys | Ala | Ser | Gln | His | Gly | Cys | His | Gly | Asp | Thr | Ile | Pro | Arg | Gly | |
| 65 | | | | 70 | | | | 75 | | | | 80 | | | | |

| atc | gaa | tac | atc | caa | caa | aat | ggt | gtc | gtt | gaa | gaa | aga | agc | tat | cca | 288 |
|---|---|---|---|---|---|---|---|---|---|---|---|---|---|---|---|---|
| Ile | Glu | Tyr | Ile | Gln | Gln | Asn | Gly | Val | Val | Glu | Glu | Arg | Ser | Tyr | Pro | |
| | | | 85 | | | | 90 | | | | 95 | | | | | |

| tac | gtt | gca | cgt | gaa | caa | cgt | tgc | cgt | cgt | cca | aat | tcg | caa | cat | tac | 336 |
|---|---|---|---|---|---|---|---|---|---|---|---|---|---|---|---|---|
| Tyr | Val | Ala | Arg | Glu | Gln | Arg | Cys | Arg | Arg | Pro | Asn | Ser | Gln | His | Tyr | |
| | 100 | | | | 105 | | | | 110 | | | | | | | |

| ggt | atc | tca | aac | tac | tgc | caa | att | tat | cca | cca | gat | gtg | aaa | caa | atc | 384 |
|---|---|---|---|---|---|---|---|---|---|---|---|---|---|---|---|---|
| Gly | Ile | Ser | Asn | Tyr | Cys | Gln | Ile | Tyr | Pro | Pro | Asp | Val | Lys | Gln | Ile | |
| 115 | | | | 120 | | | | 125 | | | | | | | | |

| cgt | gaa | gct | ttg | act | caa | aca | cac | aca | gct | att | gcc | gtc | att | att | ggc | 432 |
|---|---|---|---|---|---|---|---|---|---|---|---|---|---|---|---|---|
| Arg | Glu | Ala | Leu | Thr | Gln | Thr | His | Thr | Ala | Ile | Ala | Val | Ile | Ile | Gly | |
| | 130 | | | | 135 | | | | 140 | | | | | | | |

| att | aaa | gat | ttg | aga | gct | ttt | caa | cat | tat | gat | gga | cga | aca | atc | att | 480 |
|---|---|---|---|---|---|---|---|---|---|---|---|---|---|---|---|---|
| Ile | Lys | Asp | Leu | Arg | Ala | Phe | Gln | His | Tyr | Asp | Gly | Arg | Thr | Ile | Ile | |
| 145 | | | | 150 | | | | 155 | | | | 160 | | | | |

| caa | cat | gac | aat | ggt | tat | caa | cca | aac | tat | cat | gcc | gtc | aac | att | gtc | 528 |
|---|---|---|---|---|---|---|---|---|---|---|---|---|---|---|---|---|
| Gln | His | Asp | Asn | Gly | Tyr | Gln | Pro | Asn | Tyr | His | Ala | Val | Asn | Ile | Val | |
| | | | 165 | | | | 170 | | | | 175 | | | | | |

| ggt | tac | gga | agt | aca | caa | ggc | gtc | gat | tat | tgg | atc | gtg | cga | aac | agt | 576 |
|---|---|---|---|---|---|---|---|---|---|---|---|---|---|---|---|---|
| Gly | Tyr | Gly | Ser | Thr | Gln | Gly | Val | Asp | Tyr | Trp | Ile | Val | Arg | Asn | Ser | |
| | | 180 | | | | 185 | | | | 190 | | | | | | |

| tgg | gat | act | acc | tgg | ggt | gat | agc | gga | tac | gga | tat | ttc | caa | gcc | gga | 624 |
|---|---|---|---|---|---|---|---|---|---|---|---|---|---|---|---|---|
| Trp | Asp | Thr | Thr | Trp | Gly | Asp | Ser | Gly | Tyr | Gly | Tyr | Phe | Gln | Ala | Gly | |
| | 195 | | | | 200 | | | | 205 | | | | | | | |

| aac | aac | ctc | atg | atg | atc | gaa | caa | tat | cca | tac | gtt | gta | atc | atg | | 669 |
|---|---|---|---|---|---|---|---|---|---|---|---|---|---|---|---|---|
| Asn | Asn | Leu | Met | Met | Ile | Glu | Gln | Tyr | Pro | Tyr | Val | Val | Ile | Met | | |
| 210 | | | | 215 | | | | 220 | | | | | | | | |

```
<210> SEQ ID NO 44
<211> LENGTH: 223
```

<212> TYPE: PRT
<213> ORGANISM: Dermatophagoides farinae

<400> SEQUENCE: 44

```
Thr Ser Ala Cys Arg Ile Asn Ser Val Asn Val Pro Ser Glu Leu Asp
 1               5                  10                  15

Leu Arg Ser Leu Arg Thr Val Thr Pro Ile Arg Met Gln Gly Gly Cys
             20                  25                  30

Gly Ser Cys Trp Ala Phe Ser Gly Val Ala Ala Thr Glu Ser Ala Tyr
         35                  40                  45

Leu Ala Tyr Arg Asn Thr Ser Leu Asp Leu Ser Glu Gln Glu Leu Val
 50                  55                  60

Asp Cys Ala Ser Gln His Gly Cys His Gly Asp Thr Ile Pro Arg Gly
 65                  70                  75                  80

Ile Glu Tyr Ile Gln Gln Asn Gly Val Val Glu Arg Ser Tyr Pro
                 85                  90                  95

Tyr Val Ala Arg Glu Gln Arg Cys Arg Arg Pro Asn Ser Gln His Tyr
                100                 105                 110

Gly Ile Ser Asn Tyr Cys Gln Ile Tyr Pro Pro Asp Val Lys Gln Ile
                115                 120                 125

Arg Glu Ala Leu Thr Gln Thr His Thr Ala Ile Ala Val Ile Ile Gly
130                 135                 140

Ile Lys Asp Leu Arg Ala Phe Gln His Tyr Asp Gly Arg Thr Ile Ile
145                 150                 155                 160

Gln His Asp Asn Gly Tyr Gln Pro Asn Tyr His Ala Val Asn Ile Val
                165                 170                 175

Gly Tyr Gly Ser Thr Gln Gly Val Asp Tyr Trp Ile Val Arg Asn Ser
                180                 185                 190

Trp Asp Thr Thr Trp Gly Asp Ser Gly Tyr Gly Tyr Phe Gln Ala Gly
            195                 200                 205

Asn Asn Leu Met Met Ile Glu Gln Tyr Pro Tyr Val Val Ile Met
        210                 215                 220
```

<210> SEQ ID NO 45
<211> LENGTH: 669
<212> TYPE: DNA
<213> ORGANISM: Dermatophagoides farinae

<400> SEQUENCE: 45

```
catgattaca acgtatggat attgttcgat catcatgagg ttgtttccgg cttggaaata    60
tccgtatccg ctatcacccc aggtagtatc ccaactgttt cgcacgatcc aataatcgac   120
gccttgtgta cttccgtaac cgacaatgtt gacggcatga tagtttggtt gataaccatt   180
gtcatgttga atgattgttc gtccatcata atgttgaaaa gctctcaaat ctttaatgcc   240
aataatgacg gcaatagctg tgtgtgtttg agtcaaagct tcacggattt gtttcacatc   300
tggtggataa atttggcagt agtttgagat accgtaatgt tgcgaatttg acgacggca    360
acgttgttca cgtgcaacgt atggatagct tctttcttca acgacaccat tttgttggat   420
gtattcgatg cctcttggta ttgtatcgcc gtgacatccg tgttgagatg cgcaatcgac   480
gagttcctgt tcagaaagat ccaaagacgt gttacggtag ccaataagc tgattcagt    540
tgcggcgaca ccagagaaag cccaacatga accacagcct ccttgcatac ggattggagt   600
gacagttcgc agtgatcgta aatccaattc cgatggaacg ttaaccgaat tgatacggca   660
agcgcttgt                                                           669
```

```
<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
cgcgtccctc tcgagaaaag agaggctaga ccagcttcaa tcaaa            45

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
gggctttcct tttgcggccg ctcacatgat tacaacatat gg               42

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
gcaagagaac aaagatgcag aagaccaaat tcg                         33

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
gcgaatttgg tcttctgcat ctttgttctc ttgc                        34

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
gggagctcca tatgcgtccg gcttcaatca aaaactt                     37

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
gcgaatttgg acgacggcaa cgttgttcac                             30

<210> SEQ ID NO 52
<211> LENGTH: 36
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 52
ccctcgcgga tcctcacatg attacaacgt atggat                                    36

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 53
gtgaacaacg ttgccgtcgt ccaaattcgc                                           30

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 54
cgcatagtcc ctctcgagaa aagaacaagc gcttgccgta tc                             42

<210> SEQ ID NO 55
<211> LENGTH: 23
<212> TYPE: PRT
<213> ORGANISM: Dermatophagoides farinae

<400> SEQUENCE: 55

Ala Glu Thr Ser Ala Cys Arg Ile Asn Ser Val Asn Val Pro Ser Glu
 1               5                  10                  15

Leu Asp Leu Arg Ser Leu Arg
            20

<210> SEQ ID NO 56
<211> LENGTH: 21
<212> TYPE: PRT
<213> ORGANISM: Dermatophagoides farinae

<400> SEQUENCE: 56

Thr Ser Ala Cys Arg Ile Asn Ser Val Asn Val Pro Ser Glu Leu Asp
 1               5                  10                  15

Leu Arg Ser Leu Arg
            20

<210> SEQ ID NO 57
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 57
gccgcaactg aatcagctta tttggcctac cgtcaaacgt ctttgg                         46

<210> SEQ ID NO 58
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 58
gacaccagag aaagcccaac atgaaccaca gcctccttgc atacg                45

<210> SEQ ID NO 59
<211> LENGTH: 23
<212> TYPE: PRT
<213> ORGANISM: Dermatophagoides farinae

<400> SEQUENCE: 59

Met Arg Pro Ala Ser Ile Lys Thr Phe Glu Glu Phe Lys Lys Ala Phe
 1               5                  10                  15

Asn Lys Asn Tyr Ala Thr Val
            20

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 60
aggagacata tgcgtccatc ctcgatcaaa acttttg                         37

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 61
ttgtgcattt ggacgacggc atgattgttc tc                              32

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 62
tcaccctgga tccctacagg atgacaacgt atggatattc                      40

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 63
gagaacaatc atgccgtcgt ccaaatgcac aa                              32

<210> SEQ ID NO 64
<211> LENGTH: 909
<212> TYPE: DNA
```

<213> ORGANISM: Dermatophagoides pteronyssinus
<220> FEATURE:
<221> NAME/KEY: CDS
<222> LOCATION: (1)..(909)

<400> SEQUENCE: 64

| | | | | | | | | | | | | | | | | |
|---|---|---|---|---|---|---|---|---|---|---|---|---|---|---|---|---|
| atg | cgt | cca | tcc | tcg | atc | aaa | act | ttt | gaa | gaa | tac | aaa | aaa | gcc | ttc | 48 |
| Met | Arg | Pro | Ser | Ser | Ile | Lys | Thr | Phe | Glu | Glu | Tyr | Lys | Lys | Ala | Phe | |
| 1 | | | | 5 | | | | | 10 | | | | | 15 | | |
| aac | aaa | agt | tat | gct | acc | ttc | gaa | gat | gaa | gaa | gct | gcc | cgt | aaa | aac | 96 |
| Asn | Lys | Ser | Tyr | Ala | Thr | Phe | Glu | Asp | Glu | Glu | Ala | Ala | Arg | Lys | Asn | |
| | | | 20 | | | | | 25 | | | | | 30 | | | |
| ttt | ttg | gaa | tca | gta | aaa | tat | gtt | caa | tca | aat | gga | ggt | gcc | atc | aac | 144 |
| Phe | Leu | Glu | Ser | Val | Lys | Tyr | Val | Gln | Ser | Asn | Gly | Gly | Ala | Ile | Asn | |
| | | 35 | | | | | 40 | | | | | 45 | | | | |
| cat | ttg | tcc | gat | ttg | tcg | ttg | gat | gaa | ttc | aaa | aac | cga | ttt | ttg | atg | 192 |
| His | Leu | Ser | Asp | Leu | Ser | Leu | Asp | Glu | Phe | Lys | Asn | Arg | Phe | Leu | Met | |
| 50 | | | | | 55 | | | | | 60 | | | | | | |
| agt | gca | gaa | gct | ttt | gaa | cac | ctc | aaa | act | caa | ttc | gat | ttg | aat | gct | 240 |
| Ser | Ala | Glu | Ala | Phe | Glu | His | Leu | Lys | Thr | Gln | Phe | Asp | Leu | Asn | Ala | |
| 65 | | | | | 70 | | | | | 75 | | | | | 80 | |
| gaa | act | aac | gcc | tgc | agt | atc | aat | gga | aat | gct | cca | gct | gaa | atc | gat | 288 |
| Glu | Thr | Asn | Ala | Cys | Ser | Ile | Asn | Gly | Asn | Ala | Pro | Ala | Glu | Ile | Asp | |
| | | | | 85 | | | | | 90 | | | | | 95 | | |
| ttg | cga | caa | atg | cga | act | gtc | act | ccc | att | cgt | atg | caa | gga | ggc | tgt | 336 |
| Leu | Arg | Gln | Met | Arg | Thr | Val | Thr | Pro | Ile | Arg | Met | Gln | Gly | Gly | Cys | |
| | | | 100 | | | | | 105 | | | | | 110 | | | |
| ggt | tca | tgt | tgg | gct | ttc | tct | ggt | gtt | gcc | gca | acc | gaa | tca | gct | tat | 384 |
| Gly | Ser | Cys | Trp | Ala | Phe | Ser | Gly | Val | Ala | Ala | Thr | Glu | Ser | Ala | Tyr | |
| | | 115 | | | | | 120 | | | | | 125 | | | | |
| ttg | gct | tac | cgt | aat | caa | tca | ttg | gat | ctt | gct | gaa | caa | gaa | tta | gtc | 432 |
| Leu | Ala | Tyr | Arg | Asn | Gln | Ser | Leu | Asp | Leu | Ala | Glu | Gln | Glu | Leu | Val | |
| 130 | | | | | 135 | | | | | 140 | | | | | | |
| gat | tgt | gct | tcc | caa | cac | ggt | tgt | cat | ggt | gat | acc | att | cca | cgt | ggt | 480 |
| Asp | Cys | Ala | Ser | Gln | His | Gly | Cys | His | Gly | Asp | Thr | Ile | Pro | Arg | Gly | |
| 145 | | | | | 150 | | | | | 155 | | | | | 160 | |
| att | gaa | tac | atc | caa | cat | aat | ggt | gtc | gtc | caa | gaa | agc | tac | tat | cga | 528 |
| Ile | Glu | Tyr | Ile | Gln | His | Asn | Gly | Val | Val | Gln | Glu | Ser | Tyr | Tyr | Arg | |
| | | | | 165 | | | | | 170 | | | | | 175 | | |
| tac | gtt | gca | cga | gaa | caa | tca | tgc | cgt | cgt | cca | aat | gca | caa | cgt | ttc | 576 |
| Tyr | Val | Ala | Arg | Glu | Gln | Ser | Cys | Arg | Arg | Pro | Asn | Ala | Gln | Arg | Phe | |
| | | | 180 | | | | | 185 | | | | | 190 | | | |
| ggt | atc | tca | aac | tat | tgc | caa | att | tac | cca | cca | aat | gta | aac | aaa | att | 624 |
| Gly | Ile | Ser | Asn | Tyr | Cys | Gln | Ile | Tyr | Pro | Pro | Asn | Val | Asn | Lys | Ile | |
| | | 195 | | | | | 200 | | | | | 205 | | | | |
| cgt | gaa | gct | ttg | gct | caa | acc | cac | agc | gct | att | gcc | gtc | att | att | ggc | 672 |
| Arg | Glu | Ala | Leu | Ala | Gln | Thr | His | Ser | Ala | Ile | Ala | Val | Ile | Ile | Gly | |
| | 210 | | | | | 215 | | | | | 220 | | | | | |
| atc | aaa | gat | tta | gac | gca | ttc | cgt | cat | tat | gat | ggc | cga | aca | atc | att | 720 |
| Ile | Lys | Asp | Leu | Asp | Ala | Phe | Arg | His | Tyr | Asp | Gly | Arg | Thr | Ile | Ile | |
| 225 | | | | | 230 | | | | | 235 | | | | | 240 | |
| caa | cgc | gat | aat | ggt | tac | caa | cca | aac | tat | cac | gct | gtc | aac | att | gtt | 768 |
| Gln | Arg | Asp | Asn | Gly | Tyr | Gln | Pro | Asn | Tyr | His | Ala | Val | Asn | Ile | Val | |
| | | | | 245 | | | | | 250 | | | | | 255 | | |
| ggt | tac | agt | aac | gca | caa | ggt | gtc | gat | tat | tgg | atc | gta | cga | aac | agt | 816 |
| Gly | Tyr | Ser | Asn | Ala | Gln | Gly | Val | Asp | Tyr | Trp | Ile | Val | Arg | Asn | Ser | |
| | | | 260 | | | | | 265 | | | | | 270 | | | |
| tgg | gat | acc | aat | tgg | ggt | gat | aat | ggt | tac | ggt | tat | ttt | gct | gcc | aac | 864 |
| Trp | Asp | Thr | Asn | Trp | Gly | Asp | Asn | Gly | Tyr | Gly | Tyr | Phe | Ala | Ala | Asn | |
| | | 275 | | | | | 280 | | | | | 285 | | | | |
| atc | gat | ttg | atg | atg | att | gaa | gaa | tat | cca | tac | gtt | gtc | atc | ctg | | 909 |

```
Ile Asp Leu Met Met Ile Glu Glu Tyr Pro Tyr Val Val Ile Leu
        290                 295                 300
```

<210> SEQ ID NO 65
<211> LENGTH: 303
<212> TYPE: PRT
<213> ORGANISM: Dermatophagoides pteronyssinus

<400> SEQUENCE: 65

```
Met Arg Pro Ser Ser Ile Lys Thr Phe Glu Glu Tyr Lys Lys Ala Phe
  1               5                  10                  15

Asn Lys Ser Tyr Ala Thr Phe Glu Asp Glu Glu Ala Ala Arg Lys Asn
             20                  25                  30

Phe Leu Glu Ser Val Lys Tyr Val Gln Ser Asn Gly Gly Ala Ile Asn
         35                  40                  45

His Leu Ser Asp Leu Ser Leu Asp Glu Phe Lys Asn Arg Phe Leu Met
     50                  55                  60

Ser Ala Glu Ala Phe Glu His Leu Lys Thr Gln Phe Asp Leu Asn Ala
 65                  70                  75                  80

Glu Thr Asn Ala Cys Ser Ile Asn Gly Asn Ala Pro Ala Glu Ile Asp
                 85                  90                  95

Leu Arg Gln Met Arg Thr Val Thr Pro Ile Arg Met Gln Gly Gly Cys
            100                 105                 110

Gly Ser Cys Trp Ala Phe Ser Gly Val Ala Ala Thr Glu Ser Ala Tyr
        115                 120                 125

Leu Ala Tyr Arg Asn Gln Ser Leu Asp Leu Ala Glu Gln Glu Leu Val
    130                 135                 140

Asp Cys Ala Ser Gln His Gly Cys His Gly Asp Thr Ile Pro Arg Gly
145                 150                 155                 160

Ile Glu Tyr Ile Gln His Asn Gly Val Val Gln Glu Ser Tyr Tyr Arg
                165                 170                 175

Tyr Val Ala Arg Glu Gln Ser Cys Arg Arg Pro Asn Ala Gln Arg Phe
            180                 185                 190

Gly Ile Ser Asn Tyr Cys Gln Ile Tyr Pro Pro Asn Val Asn Lys Ile
        195                 200                 205

Arg Glu Ala Leu Ala Gln Thr His Ser Ala Ile Ala Val Ile Ile Gly
    210                 215                 220

Ile Lys Asp Leu Asp Ala Phe Arg His Tyr Asp Gly Arg Thr Ile Ile
225                 230                 235                 240

Gln Arg Asp Asn Gly Tyr Gln Pro Asn Tyr His Ala Val Asn Ile Val
                245                 250                 255

Gly Tyr Ser Asn Ala Gln Gly Val Asp Tyr Trp Ile Val Arg Asn Ser
            260                 265                 270

Trp Asp Thr Asn Trp Gly Asp Asn Gly Tyr Gly Tyr Phe Ala Ala Asn
        275                 280                 285

Ile Asp Leu Met Met Ile Glu Glu Tyr Pro Tyr Val Val Ile Leu
        290                 295                 300
```

<210> SEQ ID NO 66
<211> LENGTH: 909
<212> TYPE: DNA
<213> ORGANISM: Dermatophagoides pteronyssinus

<400> SEQUENCE: 66

```
caggatgaca acgtatggat attcttcaat catcatcaaa tcgatgttgg cagcaaaata    60
accgtaacca ttatcacccc aattggtatc ccaactgttt cgtacgatcc aataatcgac   120
```

```
accttgtgcg ttactgtaac caacaatgtt gacagcgtga tagtttggtt ggtaaccatt    180
atcgcgttga atgattgttc ggccatcata atgacgaat gcgtctaaat ctttgatgcc    240
aataatgacg gcaatagcgc tgtgggtttg agccaaagct tcacgaattt tgtttacatt    300
tggtgggtaa atttggcaat agtttgagat accgaaacgt tgtgcatttg gacgacggca    360
tgattgttct cgtgcaacgt atcgatagta gctttcttgg acgacaccat tatgttggat    420
gtattcaata ccacgtggaa tggtatcacc atgacaaccg tgttgggaag cacaatcgac    480
taattcttgt tcagcaagat ccaatgattg attacggtaa gccaaataag ctgattcggt    540
tgcggcaaca ccagagaaag cccaacatga accagcct ccttgcatac gaatgggagt    600
gacagttcgc atttgtcgca aatcgatttc agctggagca tttccattga tactgcaggc    660
gttagtttca gcattcaaat cgaattgagt tttgaggtgt tcaaaagctt ctgcactcat    720
caaaaatcgg ttttgaatt catccaacga caaatcggac aaatggttga tggcacctcc    780
atttgattga acatatttta ctgattccaa aaagttttta cgggcagctt cttcatcttc    840
gaaggtagca taacttttgt tgaaggcttt tttgtattct tcaaaagttt tgatcgagga    900
tggacgcat                                                            909
```

```
<210> SEQ ID NO 67
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 67
aaaaaaaaac atatgactaa cgcctgcagt atcaatggaa atg                      43

<210> SEQ ID NO 68
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 68
aaaaaaaaac tcgagctaca ggatgacaac gtatggatat tc                       42

<210> SEQ ID NO 69
<211> LENGTH: 669
<212> TYPE: DNA
<213> ORGANISM: Dermatophagoides pteronyssinus
<220> FEATURE:
<221> NAME/KEY: CDS
<222> LOCATION: (1)..(669)

<400> SEQUENCE: 69
```

```
atg act aac gcc tgc agt atc aat gga aat gct cca gct gaa atc gat    48
Met Thr Asn Ala Cys Ser Ile Asn Gly Asn Ala Pro Ala Glu Ile Asp
 1               5                  10                  15 ttg cga caa atg cga act gtc act ccc att cgt atg caa gga ggc tgt    96
Leu Arg Gln Met Arg Thr Val Thr Pro Ile Arg Met Gln Gly Gly Cys
            20                  25                  30 ggt tca tgt tgg gct ttc tct ggt gtt gcc gca acc gaa tca gct tat   144
Gly Ser Cys Trp Ala Phe Ser Gly Val Ala Ala Thr Glu Ser Ala Tyr
        35                  40                  45 ttg gct tac cgt aat caa tca ttg gat ctt gct gaa caa gaa tta gtc   192
Leu Ala Tyr Arg Asn Gln Ser Leu Asp Leu Ala Glu Gln Glu Leu Val
    50                  55                  60
```

```
gat tgt gct tcc caa cac ggt tgt cat ggt gat acc att cca cgt ggt     240
Asp Cys Ala Ser Gln His Gly Cys His Gly Asp Thr Ile Pro Arg Gly
 65                  70                  75                  80 att gaa tac atc caa cat aat ggt gtc gtc caa gaa agc tac tat cga     288
Ile Glu Tyr Ile Gln His Asn Gly Val Val Gln Glu Ser Tyr Tyr Arg
                 85                  90                  95 tac gtt gca cga gaa caa tca tgc cgt cgt cca aat gca caa cgt ttc     336
Tyr Val Ala Arg Glu Gln Ser Cys Arg Arg Pro Asn Ala Gln Arg Phe
            100                 105                 110 ggt atc tca aac tat tgc caa att tac cca cca aat gta aac aaa att     384
Gly Ile Ser Asn Tyr Cys Gln Ile Tyr Pro Pro Asn Val Asn Lys Ile
        115                 120                 125 cgt gaa gct ttg gct caa acc cac agc gct att gcc gtc att att ggc     432
Arg Glu Ala Leu Ala Gln Thr His Ser Ala Ile Ala Val Ile Ile Gly
130                 135                 140 atc aaa gat tta gac gca ttc cgt cat tat gat ggc cga aca atc att     480
Ile Lys Asp Leu Asp Ala Phe Arg His Tyr Asp Gly Arg Thr Ile Ile
145                 150                 155                 160 caa cgc gat aat ggt tac caa cca aac tat cac gct gtc aac att gtt     528
Gln Arg Asp Asn Gly Tyr Gln Pro Asn Tyr His Ala Val Asn Ile Val
                165                 170                 175 ggt tac agt aac gca caa ggt gtc gat tat tgg atc gta cga aac agt     576
Gly Tyr Ser Asn Ala Gln Gly Val Asp Tyr Trp Ile Val Arg Asn Ser
            180                 185                 190 tgg gat acc aat tgg ggt gat aat ggt tac ggt tat ttt gct gcc aac     624
Trp Asp Thr Asn Trp Gly Asp Asn Gly Tyr Gly Tyr Phe Ala Ala Asn
        195                 200                 205 atc gat ttg atg atg att gaa gaa tat cca tac gtt gtc atc ctg         669
Ile Asp Leu Met Met Ile Glu Glu Tyr Pro Tyr Val Val Ile Leu
210                 215                 220

<210> SEQ ID NO 70
<211> LENGTH: 223
<212> TYPE: PRT
<213> ORGANISM: Dermatophagoides pteronyssinus

<400> SEQUENCE: 70

Met Thr Asn Ala Cys Ser Ile Asn Gly Asn Ala Pro Ala Glu Ile Asp
 1               5                  10                  15

Leu Arg Gln Met Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
        35                  40                  45

Leu Ala Tyr Arg Asn Gln Ser Leu Asp Leu Ala Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln His Asn Gly Val Val Gln Glu Ser Tyr Tyr Arg
                85                  90                  95

Tyr Val Ala Arg Glu Gln Ser Cys Arg Arg Pro Asn Ala Gln Arg Phe
            100                 105                 110

Gly Ile Ser Asn Tyr Cys Gln Ile Tyr Pro Pro Asn Val Asn Lys Ile
        115                 120                 125

Arg Glu Ala Leu Ala Gln Thr His Ser Ala Ile Ala Val Ile Ile Gly
130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
```

```
                    165                 170                 175
Gly Tyr Ser Asn Ala Gln Gly Val Asp Tyr Trp Ile Val Arg Asn Ser
            180                 185                 190

Trp Asp Thr Asn Trp Gly Asp Asn Gly Tyr Gly Tyr Phe Ala Ala Asn
        195                 200                 205

Ile Asp Leu Met Met Ile Glu Glu Tyr Pro Tyr Val Val Ile Leu
    210                 215                 220

<210> SEQ ID NO 71
<211> LENGTH: 669
<212> TYPE: DNA
<213> ORGANISM: Dermatophagoides pteronyssinus

<400> SEQUENCE: 71
caggatgaca acgtatggat attcttcaat catcatcaaa tcgatgttgg cagcaaaata      60
accgtaacca ttatcacccc aattggtatc ccaactgttt cgtacgatcc aataatcgac     120
accttgtgcg ttactgtaac caacaatgtt gacagcgtga tagtttggtt ggtaaccatt     180
atcgcgttga atgattgttc ggccatcata atgacggaat gcgtctaaat ctttgatgcc     240
aataatgacg gcaatagcgc tgtgggtttg agccaaagct tcacgaattt tgtttacatt     300
tggtgggtaa atttggcaat agtttgagat accgaaacgt tgtgcatttg gacgacggca     360
tgattgttct cgtgcaacgt atcgatagta gctttcttgg acgacaccat tatgttggat     420
gtattcaata ccacgtggaa tggtatcacc atgacaaccg tgttgggaag cacaatcgac     480
taattcttgt tcagcaagat ccaatgattg attacggtaa gccaaataag ctgattcggt     540
tgcggcaaca ccagagaaag cccaacatga accacagcct ccttgcatac gaatgggagt     600
gacagttcgc atttgtcgca aatcgatttc agctggagca tttccattga tactgcaggc     660
gttagtcat                                                            669

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 72
gtggctctcg agaagagaga ggctcgtcca tcttccatca aaact                     45

<210> SEQ ID NO 73
<211> LENGTH: 44
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 73
ccgaatcttt gtgcatttgg tcttctgcat gattgttctc gtgc                      44

<210> SEQ ID NO 74
<211> LENGTH: 44
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 74
```

-continued gcacgagaac aatcatgcag aagaccaaat gcacaaagat tcgg    44

<210> SEQ ID NO 75
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 75
gctcttgcgg ccgcttacaa aatgacaacg tatggata    38

<210> SEQ ID NO 76
<211> LENGTH: 906
<212> TYPE: DNA
<213> ORGANISM: Dermatophagoides pteronyssinus
<220> FEATURE:
<221> NAME/KEY: CDS
<222> LOCATION: (1)..(906)

<400> SEQUENCE: 76

```
cgt cca tct tcc atc aaa act ttt gaa gaa tac aaa aaa gcc ttc aac      48
Arg Pro Ser Ser Ile Lys Thr Phe Glu Glu Tyr Lys Lys Ala Phe Asn
 1               5                  10                  15 aaa agt tat gct acc ttc gaa gat gaa gaa gct gcc cgt aaa aac ttt      96
Lys Ser Tyr Ala Thr Phe Glu Asp Glu Glu Ala Ala Arg Lys Asn Phe
             20                  25                  30 ttg gaa tca gta aaa tat gtt caa tca aat gga ggt gcc atc aac cat     144
Leu Glu Ser Val Lys Tyr Val Gln Ser Asn Gly Gly Ala Ile Asn His
         35                  40                  45 ttg tcc gat ttg tcg ttg gat gaa ttc aaa aac cga ttt ttg atg agt     192
Leu Ser Asp Leu Ser Leu Asp Glu Phe Lys Asn Arg Phe Leu Met Ser
     50                  55                  60 gca gaa gct ttt gaa cac ctc aaa act caa ttc gat ttg aat gct gaa     240
Ala Glu Ala Phe Glu His Leu Lys Thr Gln Phe Asp Leu Asn Ala Glu
 65                  70                  75                  80 act aac gcc tgc agt atc aat gga aat gct cca gct gaa atc gat ttg     288
Thr Asn Ala Cys Ser Ile Asn Gly Asn Ala Pro Ala Glu Ile Asp Leu
                 85                  90                  95 cga caa atg cga act gtc act ccc att cgt atg caa gga ggc tgt ggt     336
Arg Gln Met Arg Thr Val Thr Pro Ile Arg Met Gln Gly Gly Cys Gly
            100                 105                 110 tca tgt tgg gct ttc tct ggt gtt gcc gca act gaa tca gct tat ttg     384
Ser Cys Trp Ala Phe Ser Gly Val Ala Ala Thr Glu Ser Ala Tyr Leu
        115                 120                 125 gct tac cgt aat caa tca ttg gat ctt gct gaa caa gaa tta gtc gat     432
Ala Tyr Arg Asn Gln Ser Leu Asp Leu Ala Glu Gln Glu Leu Val Asp
    130                 135                 140 tgt gct tcc caa cac ggt tgt cat ggt gat acc att cca cgt ggt att     480
Cys Ala Ser Gln His Gly Cys His Gly Asp Thr Ile Pro Arg Gly Ile
145                 150                 155                 160 gaa tac atc caa cat aat ggt gtc gtc caa gaa agc tac tat cga tac     528
Glu Tyr Ile Gln His Asn Gly Val Val Gln Glu Ser Tyr Tyr Arg Tyr
                165                 170                 175 gtt gca cga gaa caa tca tgc aga aga cca aat gca caa aga ttc ggt     576
Val Ala Arg Glu Gln Ser Cys Arg Arg Pro Asn Ala Gln Arg Phe Gly
            180                 185                 190 atc tca aac tat tgc caa att tac cca cca aat gcg aac aaa att cgt     624
Ile Ser Asn Tyr Cys Gln Ile Tyr Pro Pro Asn Ala Asn Lys Ile Arg
        195                 200                 205 gaa gct ttg gct caa acc cac agc gct att gcc gtc att att ggc atc     672
Glu Ala Leu Ala Gln Thr His Ser Ala Ile Ala Val Ile Ile Gly Ile
```

```
                    210                 215                 220
aaa gat tta gac gca ttc cgt cat tat gat ggc cga aca atc att caa        720
Lys Asp Leu Asp Ala Phe Arg His Tyr Asp Gly Arg Thr Ile Ile Gln
225                 230                 235                 240 cgc gat aat ggt tac caa cca aac tat cac gct gtc aac att gtt ggt        768
Arg Asp Asn Gly Tyr Gln Pro Asn Tyr His Ala Val Asn Ile Val Gly
                    245                 250                 255 tac agt aac gca caa ggt gtc gat tat tgg atc gta cga aac agt tgg        816
Tyr Ser Asn Ala Gln Gly Val Asp Tyr Trp Ile Val Arg Asn Ser Trp
                260                 265                 270 gat acc aat tgg ggt gat aat ggt tac ggt tat ttt gct gcc aac atc        864
Asp Thr Asn Trp Gly Asp Asn Gly Tyr Gly Tyr Phe Ala Ala Asn Ile
            275                 280                 285 gat tta atg atg att gaa gaa tat cca tac gtt gtc att ttg                906
Asp Leu Met Met Ile Glu Glu Tyr Pro Tyr Val Val Ile Leu
            290                 295                 300

<210> SEQ ID NO 77
<211> LENGTH: 302
<212> TYPE: PRT
<213> ORGANISM: Dermatophagoides pteronyssinus

<400> SEQUENCE: 77

Arg Pro Ser Ser Ile Lys Thr Phe Glu Glu Tyr Lys Lys Ala Phe Asn
 1               5                  10                  15

Lys Ser Tyr Ala Thr Phe Glu Asp Glu Glu Ala Ala Arg Lys Asn Phe
                20                  25                  30

Leu Glu Ser Val Lys Tyr Val Gln Ser Asn Gly Gly Ala Ile Asn His
            35                  40                  45

Leu Ser Asp Leu Ser Leu Asp Glu Phe Lys Asn Arg Phe Leu Met Ser
        50                  55                  60

Ala Glu Ala Phe Glu His Leu Lys Thr Gln Phe Asp Leu Asn Ala Glu
65                  70                  75                  80

Thr Asn Ala Cys Ser Ile Asn Gly Asn Ala Pro Ala Glu Ile Asp Leu
                85                  90                  95

Arg Gln Met Arg Thr Val Thr Pro Ile Arg Met Gln Gly Gly Cys Gly
            100                 105                 110

Ser Cys Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
130                 135                 140

Cys Ala Ser Gln His Gly Cys His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Cys Arg Arg Pro Asn Ala Gln Arg Phe Gly
            180                 185                 190

Ile Ser Asn Tyr Cys Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270
```

```
Asp Thr Asn Trp Gly Asp Asn Gly Tyr Gly Tyr Phe Ala Ala Asn Ile
            275                 280                 285

Asp Leu Met Met Ile Glu Glu Tyr Pro Tyr Val Val Ile Leu
            290                 295                 300

<210> SEQ ID NO 78
<211> LENGTH: 906
<212> TYPE: DNA
<213> ORGANISM: Dermatophagoides pteronyssinus

<400> SEQUENCE: 78
caaaatgaca acgtatggat attcttcaat catcattaaa tcgatgttgg cagcaaaata      60
accgtaacca ttatcacccc aattggtatc ccaactgttt cgtacgatcc aataatcgac     120
accttgtgcg ttactgtaac caacaatgtt gacagcgtga tagtttggtt ggtaaccatt     180
atcgcgttga atgattgttc ggccatcata atgacggaat gcgtctaaat ctttgatgcc     240
aataatgacg gcaatagcgc tgtgggtttg agccaaagct tcacgaattt tgttcgcatt     300
tggtgggtaa atttggcaat agtttgagat accgaatctt tgtgcatttg gtcttctgca     360
tgattgttct cgtgcaacgt atcgatagta gctttcttgg acgacaccat tatgttggat     420
gtattcaata ccacgtggaa tggtatcacc atgacaaccg tgttgggaag cacaatcgac     480
taattcttgt tcagcaagat ccaatgattg attacgttaa gccaaataag ctgattcagt     540
tgcggcaaca ccagagaaag cccaacatga accacagcct ccttgcatac gaatgggagt     600
gacagttcgc atttgtcgca aatcgatttc agctggagca tttccattga tactgcaggc     660
gttagtttca gcattcaaat cgaattgagt tttgaggtgt caaaagcttt ctgcactcat     720
caaaaatcgg tttttgaatt catccaacga caaatcggac aaatggttga tgcacctcc      780 atttgattga acatatttta ctgattccaa aaagttttta cgggcagctt cttcatcttc     840
gaaggtagca taacttttgt tgaaggcttt tttgtattct tcaaaagttt tgatggaaga     900
tggacg                                                               906

<210> SEQ ID NO 79
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 79
ggggtatctc tcgagaagag aactaacgcc tgcagtatca atg                       43

<210> SEQ ID NO 80
<211> LENGTH: 41
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 80
aagctggcgg ccgcttacaa aatgacaacg tatggatatt c                         41

<210> SEQ ID NO 81
<211> LENGTH: 666
<212> TYPE: DNA
<213> ORGANISM: Dermatophagoides pteronyssinus
<220> FEATURE:
<221> NAME/KEY: CDS
```

```
<222> LOCATION: (1)..(666)

<400> SEQUENCE: 81 act aac gcc tgc agt atc aat gga aat gct cca gct gaa atc gat ttg      48
Thr Asn Ala Cys Ser Ile Asn Gly Asn Ala Pro Ala Glu Ile Asp Leu
  1               5                  10                  15 cga caa atg cga act gtc act ccc att cgt atg caa gga ggc tgt ggt      96
Arg Gln Met Arg Thr Val Thr Pro Ile Arg Met Gln Gly Gly Cys Gly
             20                  25                  30 tca tgt tgg gct ttc tct ggt gtt gcc gca act gaa tca gct tat ttg     144
Ser Cys Trp Ala Phe Ser Gly Val Ala Ala Thr Glu Ser Ala Tyr Leu
         35                  40                  45 gct tac cgt aat caa tca ttg gat ctt gct gaa caa gaa tta gtc gat     192
Ala Tyr Arg Asn Gln Ser Leu Asp Leu Ala Glu Gln Glu Leu Val Asp
     50                  55                  60 tgt gct tcc caa cac ggt tgt cat ggt gat acc att cca cgt ggt att     240
Cys Ala Ser Gln His Gly Cys His Gly Asp Thr Ile Pro Arg Gly Ile
 65                  70                  75                  80 gaa tac atc caa cat aat ggt gtc gtc caa gaa agc tac tat cga tac     288
Glu Tyr Ile Gln His Asn Gly Val Val Gln Glu Ser Tyr Tyr Arg Tyr
                 85                  90                  95 gtt gca cga gaa caa tca tgc aga aga cca aat gca caa aga ttc ggt     336
Val Ala Arg Glu Gln Ser Cys Arg Arg Pro Asn Ala Gln Arg Phe Gly
            100                 105                 110 atc tca aac tat tgc caa att tac cca cca aat gcg aac aaa att cgt     384
Ile Ser Asn Tyr Cys Gln Ile Tyr Pro Pro Asn Ala Asn Lys Ile Arg
        115                 120                 125 gaa gct ttg gct caa acc cac agc gct att gcc gtc att att ggc atc     432
Glu Ala Leu Ala Gln Thr His Ser Ala Ile Ala Val Ile Ile Gly Ile
    130                 135                 140 aaa gat tta gac gca ttc cgt cat tat gat ggc cga aca atc att caa     480
Lys Asp Leu Asp Ala Phe Arg His Tyr Asp Gly Arg Thr Ile Ile Gln
145                 150                 155                 160 cgc gat aat ggt tac caa cca aac tat cac gct gtc aac att gtt ggt     528
Arg Asp Asn Gly Tyr Gln Pro Asn Tyr His Ala Val Asn Ile Val Gly
                165                 170                 175 tac agt aac gca caa ggt gtc gat tat tgg atc gta cga aac agt tgg     576
Tyr Ser Asn Ala Gln Gly Val Asp Tyr Trp Ile Val Arg Asn Ser Trp
            180                 185                 190 gat acc aat tgg ggt gat aat ggt tac ggt tat ttt gct gcc aac atc     624
Asp Thr Asn Trp Gly Asp Asn Gly Tyr Gly Tyr Phe Ala Ala Asn Ile
        195                 200                 205 gat tta atg atg att gaa gaa tat cca tac gtt gtc att ttg             666
Asp Leu Met Met Ile Glu Glu Tyr Pro Tyr Val Val Ile Leu
    210                 215                 220

<210> SEQ ID NO 82
<211> LENGTH: 222
<212> TYPE: PRT
<213> ORGANISM: Dermatophagoides pteronyssinus

<400> SEQUENCE: 82

Thr Asn Ala Cys Ser Ile Asn Gly Asn Ala Pro Ala Glu Ile Asp Leu
  1               5                  10                  15

Arg Gln Met Arg Thr Val Thr Pro Ile Arg Met Gln Gly Gly Cys Gly
             20                  25                  30

Ser Cys Trp Ala Phe Ser Gly Val Ala Ala Thr Glu Ser Ala Tyr Leu
         35                  40                  45

Ala Tyr Arg Asn Gln Ser Leu Asp Leu Ala Glu Gln Glu Leu Val Asp
     50                  55                  60
```

```
Cys Ala Ser Gln His Gly Cys His Gly Asp Thr Ile Pro Arg Gly Ile
 65                  70                  75                  80

Glu Tyr Ile Gln His Asn Gly Val Val Gln Ser Tyr Tyr Arg Tyr
             85                  90                  95

Val Ala Arg Glu Gln Ser Cys Arg Pro Asn Ala Gln Arg Phe Gly
            100                 105                 110

Ile Ser Asn Tyr Cys Gln Ile Tyr Pro Pro Asn Ala Asn Lys Ile Arg
            115                 120                 125

Glu Ala Leu Ala Gln Thr His Ser Ala Ile Ala Val Ile Ile Gly Ile
130                 135                 140

Lys Asp Leu Asp Ala Phe Arg His Tyr Asp Gly Arg Thr Ile Ile Gln
145                 150                 155                 160

Arg Asp Asn Gly Tyr Gln Pro Asn Tyr His Ala Val Asn Ile Val Gly
                165                 170                 175

Tyr Ser Asn Ala Gln Gly Val Asp Tyr Trp Ile Val Arg Asn Ser Trp
            180                 185                 190

Asp Thr Asn Trp Gly Asp Asn Gly Tyr Gly Tyr Phe Ala Ala Asn Ile
            195                 200                 205

Asp Leu Met Met Ile Glu Glu Tyr Pro Tyr Val Val Ile Leu
    210                 215                 220
```

<210> SEQ ID NO 83
<211> LENGTH: 666
<212> TYPE: DNA
<213> ORGANISM: Dermatophagoides pteronyssinus

<400> SEQUENCE: 83

```
caaaatgaca acgtatggat attcttcaat catcattaaa tcgatgttgg cagcaaaata      60
accgtaacca ttatcacccc aattggtatc ccaactgttt cgtacgatcc aataatcgac     120
accttgtgcg ttactgtaac caacaatgtt gacagcgtga tagtttggtt ggtaaccatt     180
atcgcgttga tgattgttc ggccatcata atgacggaat gcgtctaaat ctttgatgcc     240
aataatgacg gcaatagcgc tgtgggtttg agccaaagct tcacgaattt tgttcgcatt     300
tggtgggtaa atttggcaat agtttgagat accgaatctt tgtgcatttg gtcttctgca     360
tgattgttct cgtgcaacgt atcgatagta gctttcttgg acgacaccat tatgttggat     420
gtattcaata ccacgtggaa tggtatcacc atgacaaccg tgttgggaag cacaatcgac     480
taattcttgt tcagcaagat ccaatgattg attacggtaa gccaaataag ctgattcagt     540
tgcggcaaca ccagagaaag cccaacatga accacagcct ccttgcatac gaatgggagt     600
gacagttcgc atttgtcgca aatcgatttc agctggagca tttccattga tactgcaggc     660
gttagt                                                               666
```

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 84

```
aaataagctg attcagttgc ggcaacacca gag                                   33
```

<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 85
ggcttaccgt aatcaaggtt tggatcttgc tg                                    32

<210> SEQ ID NO 86
<211> LENGTH: 906
<212> TYPE: DNA
<213> ORGANISM: Dermatophagoides pteronyssinus
<220> FEATURE:
<221> NAME/KEY: CDS
<222> LOCATION: (1)..(906)

<400> SEQUENCE: 86

```
cgt cca tct tcc atc aaa act ttt gaa gaa tac aaa aaa gcc ttc aac        48
Arg Pro Ser Ser Ile Lys Thr Phe Glu Glu Tyr Lys Lys Ala Phe Asn
  1               5                  10                  15 aaa agt tat gct acc ttc gaa gat gaa gaa gct gcc cgt aaa aac ttt        96
Lys Ser Tyr Ala Thr Phe Glu Asp Glu Glu Ala Ala Arg Lys Asn Phe
             20                  25                  30 ttg gaa tca gta aaa tat gtt caa tca aat gga ggt gcc atc aac cat       144
Leu Glu Ser Val Lys Tyr Val Gln Ser Asn Gly Gly Ala Ile Asn His
         35                  40                  45 ttg tcc gat ttg tcg ttg gat gaa ttc aaa aac cga ttt ttg atg agt       192
Leu Ser Asp Leu Ser Leu Asp Glu Phe Lys Asn Arg Phe Leu Met Ser
     50                  55                  60 gca gaa gct ttt gaa cac ctc aaa act caa ttc gat ttg aat gct gaa       240
Ala Glu Ala Phe Glu His Leu Lys Thr Gln Phe Asp Leu Asn Ala Glu
 65                  70                  75                  80 act aac gcc tgc agt atc aat gga aat gct cca gct gaa atc gat ttg       288
Thr Asn Ala Cys Ser Ile Asn Gly Asn Ala Pro Ala Glu Ile Asp Leu
                 85                  90                  95 cga caa atg cga act gtc act ccc att cgt atg caa gga ggc tgt ggt       336
Arg Gln Met Arg Thr Val Thr Pro Ile Arg Met Gln Gly Gly Cys Gly
            100                 105                 110 tca tgt tgg gct ttc tct ggt gtt gcc gca act gaa tca gct tat ttg       384
Ser Cys Trp Ala Phe Ser Gly Val Ala Ala Thr Glu Ser Ala Tyr Leu
        115                 120                 125 gct tac cgt aat caa ggt ttg gat ctt gct gaa caa gaa tta gtc gat       432
Ala Tyr Arg Asn Gln Gly Leu Asp Leu Ala Glu Gln Glu Leu Val Asp
    130                 135                 140 tgt gct tcc caa cac ggt tgt cat ggt gat acc att cca cgt ggt att       480
Cys Ala Ser Gln His Gly Cys His Gly Asp Thr Ile Pro Arg Gly Ile
145                 150                 155                 160 gaa tac atc caa cat aat ggt gtc gtc caa gaa agc tac tat cga tac       528
Glu Tyr Ile Gln His Asn Gly Val Val Gln Glu Ser Tyr Tyr Arg Tyr
                165                 170                 175 gtt gca cga gaa caa tca tgc aga aga cca aat gca caa aga ttc ggt       576
Val Ala Arg Glu Gln Ser Cys Arg Arg Pro Asn Ala Gln Arg Phe Gly
            180                 185                 190 atc tca aac tat tgc caa att tac cca cca aat gcg aac aaa att cgt       624
Ile Ser Asn Tyr Cys Gln Ile Tyr Pro Pro Asn Ala Asn Lys Ile Arg
        195                 200                 205 gaa gct ttg gct caa acc cac agc gct att gcc gtc att att ggc atc       672
Glu Ala Leu Ala Gln Thr His Ser Ala Ile Ala Val Ile Ile Gly Ile
    210                 215                 220 aaa gat tta gac gca ttc cgt cat tat gat ggc cga aca atc att caa       720
Lys Asp Leu Asp Ala Phe Arg His Tyr Asp Gly Arg Thr Ile Ile Gln
225                 230                 235                 240 cgc gat aat ggt tac caa cca aac tat cac gct gtc aac att gtt ggt       768
```

| | | | | | | | | | | | | |
|---|---|---|---|---|---|---|---|---|---|---|---|---|
|Arg|Asp|Asn|Gly|Tyr|Gln|Pro|Asn|Tyr|His|Ala|Val|Asn|Ile|Val|Gly|
| | | |245| | | |250| | | |255| |

| | | | | | | | | | | | | |
|---|---|---|---|---|---|---|---|---|---|---|---|---|
|tac|agt|aac|gca|caa|ggt|gtc|gat|tat|tgg|atc|gta|cga|aac|agt|tgg| |816|
|Tyr|Ser|Asn|Ala|Gln|Gly|Val|Asp|Tyr|Trp|Ile|Val|Arg|Asn|Ser|Trp|
| | | |260| | | |265| | | |270| |

| | | | | | | | | | | | | |
|---|---|---|---|---|---|---|---|---|---|---|---|---|
|gat|acc|aat|tgg|ggt|gat|aat|ggt|tac|ggt|tat|ttt|gct|gcc|aac|atc| |864|
|Asp|Thr|Asn|Trp|Gly|Asp|Asn|Gly|Tyr|Gly|Tyr|Phe|Ala|Ala|Asn|Ile|
| | | |275| | | |280| | | |285| |

| | | | | | | | | | | | |
|---|---|---|---|---|---|---|---|---|---|---|---|
|gat|tta|atg|atg|att|gaa|gaa|tat|cca|tac|gtt|gtc|att|ttg| |906|
|Asp|Leu|Met|Met|Ile|Glu|Glu|Tyr|Pro|Tyr|Val|Val|Ile|Leu|
| | | |290| | | |295| | | |300| |

<210> SEQ ID NO 87
<211> LENGTH: 302
<212> TYPE: PRT
<213> ORGANISM: Dermatophagoides pteronyssinus

<400> SEQUENCE: 87

Arg Pro Ser Ser Ile Lys Thr Phe Glu Glu Tyr Lys Lys Ala Phe Asn
 1               5                  10                  15

Lys Ser Tyr Ala Thr Phe Glu Asp Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
 50                  55                  60

Ala Glu Ala Phe Glu His Leu Lys Thr Gln Phe Asp Leu Asn Ala Glu
 65                  70                  75                  80

Thr Asn Ala Cys Ser Ile Asn Gly Asn Ala Pro Ala Glu Ile Asp Leu
                85                  90                  95

Arg Gln Met Arg Thr Val Thr Pro Ile Arg Met Gln Gly Gly Cys Gly
            100                 105                 110

Ser Cys Trp Ala Phe Ser Gly Val Ala Ala Thr Glu Ser Ala Tyr Leu
        115                 120                 125

Ala Tyr Arg Asn Gln Gly Leu Asp Leu Ala Glu Gln Glu Leu Val Asp
130                 135                 140

Cys Ala Ser Gln His Gly Cys His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Cys Arg Arg Pro Asn Ala Gln Arg Phe Gly
            180                 185                 190

Ile Ser Asn Tyr Cys Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
290                 295                 300

<210> SEQ ID NO 88
<211> LENGTH: 906
<212> TYPE: DNA
<213> ORGANISM: Dermatophagoides pteronyssinus

<400> SEQUENCE: 88

```
caaaatgaca acgtatggat attcttcaat catcattaaa tcgatgttgg cagcaaaata      60
accgtaacca ttatcacccc aattggtatc ccaactgttt cgtacgatcc aataatcgac     120
accttgtgcg ttactgtaac caacaatgtt gacagcgtga tagtttggtt ggtaaccatt     180
atcgcgttga atgattgttc ggccatcata atgacgaatg cgtctaaat ctttgatgcc      240
aataatgacg gcaatagcgc tgtgggtttg agccaaagct tcacgaattt tgttcgcatt     300
tggtgggtaa atttggcaat agtttgagat accgaatctt tgtgcatttg gtcttctgca     360
tgattgttct cgtgcaacgt atcgatagta gctttcttgg acgacaccat tatgttggat     420
gtattcaata ccacgtggaa tggtatcacc atgacaaccg tgttgggaag cacaatcgac     480
taattcttgt tcagcaagat ccaaaccttg attacggtaa gccaaataag ctgattcagt     540
tgcggcaaca ccagagaaag cccaacatga accacagcct ccttgcatac gaatgggagt     600
gacagttcgc atttgtcgca aatcgatttc agctggagca tttccattga tactgcaggc     660
gttagtttca gcattcaaat cgaattgagt tttgaggtgt tcaaaagctt ctgcactcat     720
caaaaatcgg tttttgaatt catccaacga caaatcggac aaatggttga tggcacctcc     780
atttgattga acatatttta ctgattccaa aaagttttta cgggcagctt cttcatcttc     840
gaaggtagca taacttttgt tgaaggcttt tttgtattct tcaaaagttt tgatggaaga     900
tggacg                                                               906
```

<210> SEQ ID NO 89
<211> LENGTH: 32
<212> TYPE: DNA
<213> ORGANISM: Artificial Sequence
<220> FEATURE:
<223> OTHER INFORMATION: Description of Artificial Sequence: Synthetic Primer

<400> SEQUENCE: 89

```
gctgtggttc atcttgggct ttctctggtg tt                                    32
```

<210> SEQ ID NO 90
<211> LENGTH: 32
<212> TYPE: DNA
<213> ORGANISM: Artificial Sequence
<220> FEATURE:
<223> OTHER INFORMATION: Description of Artificial Sequence: Synthetic Primer

<400> SEQUENCE: 90

```
ctccttgcat acggattgga gtgacagttc gc                                    32
```

<210> SEQ ID NO 91
<211> LENGTH: 909
<212> TYPE: DNA
<213> ORGANISM: Dermatophagoides farinae
<220> FEATURE:
<221> NAME/KEY: CDS
<222> LOCATION: (1)..(909)

<400> SEQUENCE: 91

```
aga cca gct tca atc aaa act ttt gaa gaa ttc aaa aaa gcc ttc aac       48
Arg Pro Ala Ser Ile Lys Thr Phe Glu Glu Phe Lys Lys Ala Phe Asn
 1               5                  10                  15
```

|     |     |     |     |     |     |     |     |     |     |     |     |     |     |     |     |     |
|---|---|---|---|---|---|---|---|---|---|---|---|---|---|---|---|---|
| aaa | aac | tat | gcc | acc | gtt | gaa | gag | gaa | gaa | gtt | gcc | cgt | aaa | aac | ttt | 96 |
| Lys | Asn | Tyr | Ala | Thr | Val | Glu | Glu | Glu | Val | Ala | Arg | Lys | Asn | Phe | | |
| | | 20 | | | | | 25 | | | | | 30 | | | | |
| ttg | gaa | tca | ttg | aaa | tat | gtt | gaa | gct | aac | aaa | ggt | gcc | atc | aac | cat | 144 |
| Leu | Glu | Ser | Leu | Lys | Tyr | Val | Glu | Ala | Asn | Lys | Gly | Ala | Ile | Asn | His | |
| | 35 | | | | | 40 | | | | | 45 | | | | | |
| ttg | tcc | gat | ttg | tca | ttg | gat | gaa | ttc | aaa | aac | cgt | tat | ttg | atg | agt | 192 |
| Leu | Ser | Asp | Leu | Ser | Leu | Asp | Glu | Phe | Lys | Asn | Arg | Tyr | Leu | Met | Ser | |
| 50 | | | | | 55 | | | | | 60 | | | | | | |
| gct | gaa | gct | ttt | gaa | caa | ctc | aaa | act | caa | ttc | gat | ttg | aat | gcc | gaa | 240 |
| Ala | Glu | Ala | Phe | Glu | Gln | Leu | Lys | Thr | Gln | Phe | Asp | Leu | Asn | Ala | Glu | |
| 65 | | | | 70 | | | | | 75 | | | | | 80 | | |
| aca | agc | gct | tgc | cgt | atc | aat | tcg | gtt | aac | gtt | cca | tcg | gaa | ttg | gat | 288 |
| Thr | Ser | Ala | Cys | Arg | Ile | Asn | Ser | Val | Asn | Val | Pro | Ser | Glu | Leu | Asp | |
| | | | 85 | | | | | 90 | | | | | 95 | | | |
| tta | cga | tca | ctg | cga | act | gtc | act | cca | atc | cgt | atg | caa | gga | ggc | tgt | 336 |
| Leu | Arg | Ser | Leu | Arg | Thr | Val | Thr | Pro | Ile | Arg | Met | Gln | Gly | Gly | Cys | |
| | | 100 | | | | | 105 | | | | | 110 | | | | |
| ggt | tca | tct | tgg | gct | ttc | tct | ggt | gtc | gcc | gca | act | gaa | tca | gct | tat | 384 |
| Gly | Ser | Ser | Trp | Ala | Phe | Ser | Gly | Val | Ala | Ala | Thr | Glu | Ser | Ala | Tyr | |
| | 115 | | | | | 120 | | | | | 125 | | | | | |
| ttg | gcc | tac | cgt | aac | acg | tct | ttg | gat | ctt | tct | gaa | cag | gaa | ctc | gtc | 432 |
| Leu | Ala | Tyr | Arg | Asn | Thr | Ser | Leu | Asp | Leu | Ser | Glu | Gln | Glu | Leu | Val | |
| 130 | | | | | 135 | | | | | 140 | | | | | | |
| gat | tgc | gca | tct | caa | cac | gga | tgt | cac | ggc | gat | aca | ata | cca | aga | ggc | 480 |
| Asp | Cys | Ala | Ser | Gln | His | Gly | Cys | His | Gly | Asp | Thr | Ile | Pro | Arg | Gly | |
| 145 | | | | 150 | | | | | 155 | | | | | 160 | | |
| atc | gaa | tac | atc | caa | caa | aat | ggt | gtc | gtt | gaa | gaa | aga | agc | tat | cca | 528 |
| Ile | Glu | Tyr | Ile | Gln | Gln | Asn | Gly | Val | Val | Glu | Glu | Arg | Ser | Tyr | Pro | |
| | | | 165 | | | | | 170 | | | | | 175 | | | |
| tac | gtt | gca | aga | gaa | caa | aga | tgc | aga | aga | cca | aat | tcg | caa | cat | tac | 576 |
| Tyr | Val | Ala | Arg | Glu | Gln | Arg | Cys | Arg | Arg | Pro | Asn | Ser | Gln | His | Tyr | |
| | | 180 | | | | | 185 | | | | | 190 | | | | |
| ggt | atc | tca | aac | tac | tgc | caa | att | tat | cca | cca | gat | gtg | aaa | caa | atc | 624 |
| Gly | Ile | Ser | Asn | Tyr | Cys | Gln | Ile | Tyr | Pro | Pro | Asp | Val | Lys | Gln | Ile | |
| | 195 | | | | | 200 | | | | | 205 | | | | | |
| cgt | gaa | gct | ttg | act | caa | aca | cac | aca | gct | att | gcc | gtc | att | att | ggc | 672 |
| Arg | Glu | Ala | Leu | Thr | Gln | Thr | His | Thr | Ala | Ile | Ala | Val | Ile | Ile | Gly | |
| 210 | | | | | 215 | | | | | 220 | | | | | | |
| att | aaa | gat | ttg | aga | gct | ttt | caa | cat | tat | gat | gga | cga | aca | atc | att | 720 |
| Ile | Lys | Asp | Leu | Arg | Ala | Phe | Gln | His | Tyr | Asp | Gly | Arg | Thr | Ile | Ile | |
| 225 | | | | 230 | | | | | 235 | | | | | 240 | | |
| caa | cat | gac | aat | ggt | tat | caa | cca | aac | tat | cat | gcc | gtc | aac | att | gtc | 768 |
| Gln | His | Asp | Asn | Gly | Tyr | Gln | Pro | Asn | Tyr | His | Ala | Val | Asn | Ile | Val | |
| | | | 245 | | | | | 250 | | | | | 255 | | | |
| ggt | tac | gga | agt | aca | caa | ggc | gtc | gat | tat | tgg | atc | gta | cga | aac | agt | 816 |
| Gly | Tyr | Gly | Ser | Thr | Gln | Gly | Val | Asp | Tyr | Trp | Ile | Val | Arg | Asn | Ser | |
| | | 260 | | | | | 265 | | | | | 270 | | | | |
| tgg | gat | act | acc | tgg | ggt | gat | agc | gga | tac | gga | tat | ttc | caa | gcc | gga | 864 |
| Trp | Asp | Thr | Thr | Trp | Gly | Asp | Ser | Gly | Tyr | Gly | Tyr | Phe | Gln | Ala | Gly | |
| | 275 | | | | | 280 | | | | | 285 | | | | | |
| aac | aac | ctc | atg | atg | atc | gaa | caa | tat | cca | tat | gtt | gta | atc | atg | | 909 |
| Asn | Asn | Leu | Met | Met | Ile | Glu | Gln | Tyr | Pro | Tyr | Val | Val | Ile | Met | | |
| 290 | | | | | 295 | | | | | 300 | | | | | | |

<210> SEQ ID NO 92
<211> LENGTH: 303
<212> TYPE: PRT
<213> ORGANISM: Dermatophagoides farinae

<400> SEQUENCE: 92

| | | | | | | | | | | | | | | |
|---|---|---|---|---|---|---|---|---|---|---|---|---|---|---|
| Arg | Pro | Ala | Ser | Ile | Lys | Thr | Phe | Glu | Glu | Phe | Lys | Lys | Ala | Phe | Asn |
| 1 | | | | 5 | | | | | 10 | | | | | 15 | |

Arg Pro Ala Ser Ile Lys Thr Phe Glu Glu Phe Lys Lys Ala Phe Asn
 1               5               10                  15

Lys Asn Tyr Ala Thr Val Glu Glu Glu Val Ala Arg Lys Asn Phe
             20              25                  30

Leu Glu Ser Leu Lys Tyr Val Glu Ala Asn Lys Gly Ala Ile Asn His
         35              40              45

Leu Ser Asp Leu Ser Leu Asp Glu Phe Lys Asn Arg Tyr Leu Met Ser
     50              55              60

Ala Glu Ala Phe Glu Gln Leu Lys Thr Gln Phe Asp Leu Asn Ala Glu
 65              70              75              80

Thr Ser Ala Cys Arg Ile Asn Ser Val Asn Val Pro Ser Glu Leu Asp
             85              90              95

Leu Arg Ser Leu Arg Thr Val Thr Pro Ile Arg Met Gln Gly Gly Cys
         100             105             110

Gly Ser Ser Trp Ala Phe Ser Gly Val Ala Thr Glu Ser Ala Tyr
         115             120             125

Leu Ala Tyr Arg Asn Thr Ser Leu Asp Leu Ser Glu Gln Glu Leu Val
 130             135             140

Asp Cys Ala Ser Gln His Gly Cys His Gly Asp Thr Ile Pro Arg Gly
145             150             155             160

Ile Glu Tyr Ile Gln Gln Asn Gly Val Val Glu Glu Arg Ser Tyr Pro
             165             170             175

Tyr Val Ala Arg Glu Gln Arg Cys Arg Arg Pro Asn Ser Gln His Tyr
         180             185             190

Gly Ile Ser Asn Tyr Cys Gln Ile Tyr Pro Pro Asp Val Lys Gln Ile
         195             200             205

Arg Glu Ala Leu Thr Gln Thr His Thr Ala Ile Ala Val Ile Ile Gly
 210             215             220

Ile Lys Asp Leu Arg Ala Phe Gln His Tyr Asp Gly Arg Thr Ile Ile
225             230             235             240

Gln His Asp Asn Gly Tyr Gln Pro Asn Tyr His Ala Val Asn Ile Val
             245             250             255

Gly Tyr Gly Ser Thr Gln Gly Val Asp Tyr Trp Ile Val Arg Asn Ser
         260             265             270

Trp Asp Thr Thr Trp Gly Asp Ser Gly Tyr Gly Tyr Phe Gln Ala Gly
 275             280             285

Asn Asn Leu Met Met Ile Glu Gln Tyr Pro Tyr Val Val Ile Met
 290             295             300

<210> SEQ ID NO 93
<211> LENGTH: 909
<212> TYPE: DNA
<213> ORGANISM: Dermatophagoides farinae

<400> SEQUENCE: 93

| | | |
|---|---|---|
| catgattaca acatatggat attgttcgat catcatgagg ttgtttccgg cttggaaata | 60 | |
| tccgtatccg ctatcacccc aggtagtatc ccaactgttt cgtacgatcc aataatcgac | 120 | |
| gccttgtgta cttccgtaac cgacaatgtt gacggcatga tagtttggtt gataaccatt | 180 | |
| gtcatgttga atgattgttc gtccatcata atgttgaaaa gctctcaaat ctttaatgcc | 240 | |
| aataatgacg gcaatagctg tgtgtgtttg agtcaaagct tcacggattt gtttcacatc | 300 | |
| tggtggataa atttggcagt agtttgagat accgtaatgt tgcgaatttg gtcttctgca | 360 | |
| tctttgttct cttgcaacgt atggatagct tctttcttca acgacaccat tttgttggat | 420 |

```
gtattcgatg cctcttggta ttgtatcgcc gtgacatccg tgttgagatg cgcaatcgac    480
gagttcctgt tcagaaagat ccaaagacgt gttacggtag gccaaataag ctgattcagt    540
tgcggcgaca ccagagaaag cccaagatga accacagcct ccttgcatac ggattggagt    600
gacagttcgc agtgatcgta aatccaattc cgatggaacg ttaaccgaat tgatacggca    660
agcgcttgtt tcggcattca aatcgaattg agttttgagt tgttcaaaag cttcagcact    720
catcaaataa cggtttttga attcatccaa tgacaaatcg gacaaatggt tgatggcacc    780
tttgttagct tcaacatatt tcaatgattc caaaaagttt ttacgggcaa cttcttcctc    840
ttcaacggtg gcatagtttt tgttgaaggc tttttttgaat tcttcaaaag ttttgattga    900
agctggtct                                                            909
```